(12) United States Patent
Matsuoka et al.

(10) Patent No.: US 10,709,335 B2
(45) Date of Patent: Jul. 14, 2020

(54) INFANT MONITORING SYSTEM WITH OBSERVATION-BASED SYSTEM CONTROL AND FEEDBACK LOOPS

(71) Applicant: Google LLC, Mountain View, CA (US)

(72) Inventors: Yoky Matsuoka, Los Altos Hills, CA (US); Shwetak Patel, Seattle, WA (US); Michael Dixon, Sunnyvale, CA (US); William Greene, San Bruno, CA (US)

(73) Assignee: Google LLC, Mountain View, CA (US)

( * ) Notice: Subject to any disclaimer, the term of this patent is extended or adjusted under 35 U.S.C. 154(b) by 0 days.

(21) Appl. No.: 15/859,654

(22) Filed: Dec. 31, 2017

(65) Prior Publication Data

US 2019/0200872 A1    Jul. 4, 2019

(51) Int. Cl.
*A61B 5/00* (2006.01)
*G06K 9/00* (2006.01)
*A61B 5/01* (2006.01)
*H04N 5/33* (2006.01)
(Continued)

(52) U.S. Cl.
CPC .......... *A61B 5/0077* (2013.01); *A61B 5/0013* (2013.01); *A61B 5/0082* (2013.01); *A61B 5/01* (2013.01); *A61B 5/1128* (2013.01); *A61B 5/4812* (2013.01); *A61B 5/6889* (2013.01); *G06K 9/00342* (2013.01); *G06K 9/00771* (2013.01); *G08B 21/0202* (2013.01); *H04N 5/33* (2013.01); *A61B 5/4815* (2013.01); *A61B 5/7267* (2013.01); *A61B 5/746* (2013.01);
(Continued)

(58) Field of Classification Search
CPC ........................... A61B 5/0077; A61B 5/4812
See application file for complete search history.

(56) References Cited

U.S. PATENT DOCUMENTS

| 5,555,577 A | 9/1996 | Volpe |
| 5,778,892 A | 7/1998 | Goldsmith |
| 5,993,397 A | 11/1999 | Branson |

(Continued)

OTHER PUBLICATIONS

Non-Final Office action dated Jun. 24, 2019 in U.S. Appl. No. 15/859,640, all pages.
(Continued)

*Primary Examiner* — William C Vaughn, Jr.
*Assistant Examiner* — Jerry T Jean Baptiste
(74) *Attorney, Agent, or Firm* — Kilpatrick Townsend & Stockton LLP

(57) ABSTRACT

A method of optimizing sleep of a subject using smart-home devices may include operating a smart-home system that is configured to operate in a normal mode and a sleep mode. The method may also include determining that the smart-home system should transition into the sleep mode. The smart-home devices may use a set of default parameters when operating in the sleep mode. The method may additionally include monitoring, while in the sleep mode, a sleep cycle of the subject using the smart-home devices. The method may further include detecting behavior of the subject that indicates that the sleep cycle of the subject is being interrupted or about to be interrupted, determining an environmental control that corresponds with the behavior of the subject, and adjusting the environmental control using the smart-home devices to prevent or stop the sleep cycle of the subject from being interrupted.

19 Claims, 24 Drawing Sheets

(51) Int. Cl.
*A61B 5/11* (2006.01)
*G08B 21/02* (2006.01)

(52) U.S. Cl.
CPC ......... *A61B 5/7475* (2013.01); *A61B 2503/04* (2013.01); *A61B 2562/0242* (2013.01)

(56) References Cited

U.S. PATENT DOCUMENTS

| | | | |
|---|---|---|---|
| 5,996,152 | A | 12/1999 | Wilson |
| 6,054,926 | A | 4/2000 | Deleo |
| 6,058,939 | A | 5/2000 | Goldsmith |
| 6,150,941 | A | 11/2000 | Geiger et al. |
| 6,450,168 | B1 | 9/2002 | Nguyen |
| 6,812,822 | B1 | 11/2004 | Spector |
| 6,912,743 | B1 | 7/2005 | Weil |
| 7,035,432 | B2 | 4/2006 | Szuba |
| 7,037,272 | B2 | 5/2006 | Silpachai et al. |
| 7,111,344 | B2 | 9/2006 | French |
| 7,264,586 | B2 | 9/2007 | Mackin et al. |
| 7,364,539 | B2 | 4/2008 | Mackin et al. |
| 7,810,181 | B2 | 10/2010 | Brewin et al. |
| 7,886,384 | B2 | 2/2011 | Lord |
| 8,001,630 | B2 | 8/2011 | Burkholder et al. |
| 8,291,530 | B2 | 12/2012 | Burkholder et al. |
| 8,864,665 | B2 | 10/2014 | Rotondo et al. |
| 8,893,325 | B2 | 11/2014 | Arnold, IV et al. |
| 8,943,615 | B2 | 2/2015 | Howard et al. |
| 9,364,099 | B2 | 6/2016 | Zarate |
| 9,554,958 | B2 | 1/2017 | Richards et al. |
| 9,572,528 | B1 | 2/2017 | Chang |
| 9,693,589 | B2 | 7/2017 | Howard et al. |
| 9,839,302 | B2 | 12/2017 | Frost |
| 2006/0116555 | A1* | 6/2006 | Pavlidis ............... A61B 5/01 600/300 |
| 2010/0087701 | A1* | 4/2010 | Berka ............... A61M 21/02 600/27 |
| 2010/0125949 | A1 | 5/2010 | Stebbing |
| 2013/0047336 | A1 | 2/2013 | Burkholder et al. |
| 2013/0072767 | A1 | 3/2013 | Imamura et al. |
| 2013/0201313 | A1 | 8/2013 | Khalil |
| 2013/0342691 | A1 | 12/2013 | Lewis et al. |
| 2014/0091945 | A1 | 4/2014 | Rivas et al. |
| 2014/0140368 | A1 | 5/2014 | Yildizyan et al. |
| 2014/0296661 | A1 | 10/2014 | Zwartkruis-pelgrim et al. |
| 2015/0105608 | A1 | 4/2015 | Lipoma et al. |
| 2015/0195494 | A1 | 7/2015 | Alvarez |
| 2015/0288877 | A1 | 10/2015 | Glazer |
| 2016/0035205 | A1 | 2/2016 | Messenger et al. |
| 2016/0058429 | A1* | 3/2016 | Shinar ............... A61B 10/0012 600/551 |
| 2016/0287075 | A1 | 10/2016 | Pradeep et al. |
| 2016/0364617 | A1* | 12/2016 | Silberschatz ...... G06K 9/00771 |
| 2017/0108236 | A1* | 4/2017 | Guan .................... H05B 47/19 |
| 2017/0258398 | A1* | 9/2017 | Jackson ............... A61B 5/4812 |
| 2017/0374296 | A1 | 12/2017 | Schmidt |
| 2018/0064369 | A1 | 3/2018 | Gunther et al. |
| 2018/0330169 | A1 | 11/2018 | Van Hoof et al. |

OTHER PUBLICATIONS

Non-Final Office Action dated Aug. 13, 2019 in U.S. Appl. No. 15/859,650, all pages.

Notice of Allowance dated Dec. 2, 2019 in U.S. Appl. No. 15/859,640, all pages.

\* cited by examiner

INFANT MONITORING SYSTEM WITH OBSERVATION-BASED SYSTEM CONTROL AND FEEDBACK LOOPS

CROSS REFERENCE TO RELATED APPLICATIONS

This patent application is related to U.S. patent application Ser. No. 15/859,640, entitled "ENHANCED VISUALIZATION OF BREATHING OR HEARTBEAT OF AN INFANT OR OTHER MONITORED SUBJECT" filed concurrently with the present application on Dec. 31, 2017, which is hereby incorporated by reference in its entirety for all purposes.

This patent application is also related to U.S. patent application Ser. No. 15/859,650, entitled "INFANT MONITORING SYSTEM WITH VIDEO-BASED TEMPERATURE BASELINING AND ELEVATED TEMPERATURE DETECTION" filed concurrently with the present application on Dec. 31, 2017, which is hereby incorporated by reference in its entirety for all purposes.

TECHNICAL FIELD

This patent specification relates generally to a smart-home environment for monitoring subject. More particularly, this patent specification describes automatic control of smart-home devices, such as video camera assemblies, keypads, security system sensors, thermostats, hazard detectors, doorbells, and/or the like, to create an optimal sleep environment for a monitored subject.

BACKGROUND

Smart-home devices are rapidly becoming part of the modern home experience. These devices may include thermostats, keypads, touch screens, and/or other control devices for controlling environmental systems, such as HVAC systems or lighting systems. The smart-home environment may also include smart appliances, such as washing machines, dishwashers, refrigerators, garbage cans, and so forth, that interface with control and/or monitoring devices to increase the level of functionality and control provided to an occupant. Security systems, including cameras, keypads, sensors, motion detectors, glass-break sensors, microphones, and so forth, may also be installed as part of the smart-home architecture. Other smart-the home devices may include doorbells, monitoring systems, hazard detectors, smart lightbulbs, and virtually any other electronic device that can be controlled via a wired/wireless network.

Many modern smart-home environments may include video cameras. These video cameras may be used for security systems, monitoring systems, hazard detection systems, and so forth. In general, video cameras provide a live video feed that can be played at a local console or on a computing system of the user, allowing them to remotely monitor a portion of the smart-home environment or its surroundings.

BRIEF SUMMARY

In some embodiments, a method of monitoring and optimizing the sleep of a subject using a plurality of smart-home devices may include operating a smart-home system comprising the plurality of smart-home devices. The smart-home system may be configured to operate in a plurality of modes including a normal operating mode and a sleep mode. The method may also include determining that the smart-home system should transition into the sleep mode from the normal operating mode. The plurality of smart-home devices may use a set of default parameters when operating in the sleep mode. The method may additionally include monitoring, while in the sleep mode, a sleep cycle of the subject using the plurality of smart-home devices. The method may further include detecting, by the plurality of smart-home devices, behavior of the subject that indicates that the sleep cycle of the subject is being interrupted or about to be interrupted, and determining an environmental control that corresponds with the behavior of the subject. The method may also include adjusting the environmental control using the plurality of smart-home devices. The adjusting may be configured to prevent or stop the sleep cycle of the subject from being interrupted.

In some embodiments, a smart-home system for monitoring and optimizing the sleep of a subject using a plurality of smart-home devices may include a plurality of smart-home devices that are configured to operate in a plurality of modes including a normal operating mode and a sleep mode. The system may also include one or more processors and one or more memory devices comprising instructions that, when executed by the one or more processors, cause the one or more processors to perform operations that may include determining that the smart-home system should transition into the sleep mode from the normal operating mode. The plurality of smart-home devices may use a set of default parameters when operating in the sleep mode. The operations may additionally include monitoring, while in the sleep mode, a sleep cycle of the subject using the plurality of smart-home devices. The operations may further include detecting, by the plurality of smart-home devices, behavior of the subject that indicates that the sleep cycle of the subject is being interrupted or about to be interrupted, and determining an environmental control that corresponds with the behavior of the subject. The operations may also include adjusting the environmental control using the plurality of smart-home devices. The adjusting may be configured to prevent or stop the sleep cycle of the subject from being interrupted.

A further understanding of the nature and advantages of the present invention may be realized by reference to the remaining portions of the specification and the drawings. Also note that other embodiments may be described in the following disclosure and claims.

DETAILED DESCRIPTION

In the following detailed description, for purposes of explanation, numerous specific details are set forth to provide a thorough understanding of the various embodiments of the present invention. Those of ordinary skill in the art will realize that these various embodiments of the present invention are illustrative only and are not intended to be limiting in any way. Other embodiments of the present invention will readily suggest themselves to such skilled persons having the benefit of this disclosure. It will be apparent to one skilled in the art that the present invention may be practiced without some or all of these specific details. In other instances, well known details have not been described in detail in order not to unnecessarily obscure the present invention.

In addition, for clarity purposes, not all of the routine features of the embodiments described herein are shown or described. One of ordinary skill in the art would readily appreciate that in the development of any such actual embodiment, numerous embodiment-specific decisions may be required to achieve specific design objectives. These design objectives will vary from one embodiment to another and from one developer to another. Moreover, it will be appreciated that such a development effort might be complex and time-consuming but would nevertheless be a routine engineering undertaking for those of ordinary skill in the art having the benefit of this disclosure.

Figure 1:
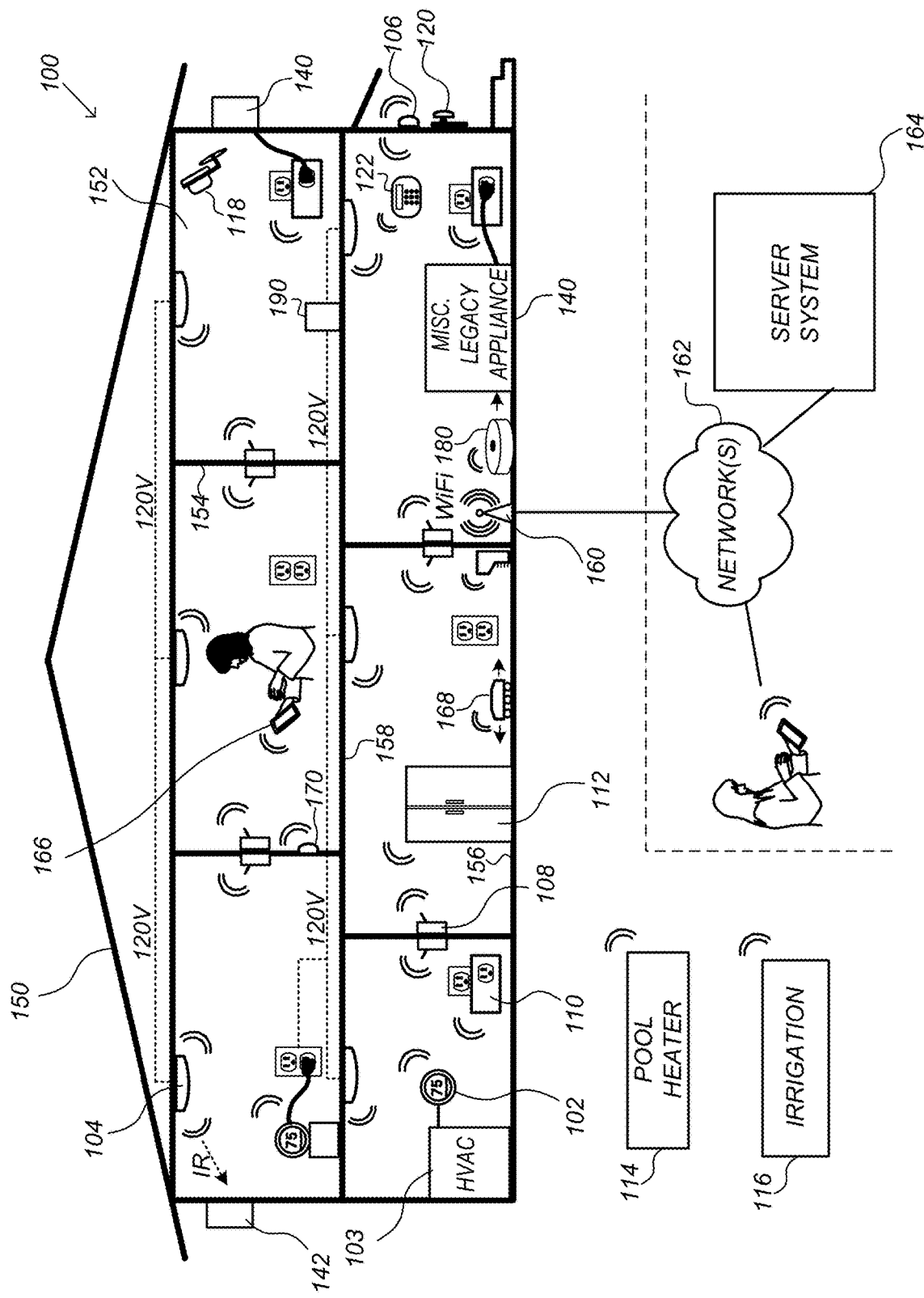
FIG. 1 is an example of a smart-home environment within which one or more of the devices, methods, systems, services, and/or computer program products described further herein will be applicable, according to some embodiments.

FIG. 1 illustrates an example smart-home environment 100, according to some embodiments. The smart-home environment 100 includes a structure 150 (e.g., a house, office building, garage, or mobile home) with various integrated devices. It will be appreciated that devices may also be integrated into a smart-home environment 100 that does not include an entire structure 150, such as an apartment, condominium, or office space. Further, the smart-home environment 100 may control and/or be coupled to devices outside of the actual structure 150. Indeed, several devices in the smart-home environment 100 need not be physically within the structure 150. For example, a device controlling a pool heater 114 or irrigation system 116 may be located outside of the structure 150.

The term "smart-home environment" may refer to smart environments for homes such as a single-family house, but the scope of the present teachings is not so limited. The present teachings are also applicable, without limitation, to duplexes, townhomes, multi-unit apartment buildings, hotels, retail stores, office buildings, industrial buildings, and more generally any living space or work space. Similarly, while the terms user, customer, installer, homeowner, occupant, guest, tenant, landlord, repair person, etc., may be used to refer to a person or persons acting in the context of some particular situations described herein, these references do not limit the scope of the present teachings with respect to the person or persons who are performing such actions. Thus, for example, the terms user, customer, purchaser, installer, subscriber, and homeowner may often refer to the same person in the case of a single-family residential dwelling, because the head of the household is often the person who makes the purchasing decision, buys the unit, and installs and configures the unit, as well as being one of the users of the unit. However, in other scenarios, such as a landlord-tenant environment, the customer may be the landlord with respect to purchasing the unit, the installer may be a local apartment supervisor, a first user may be the tenant, and a second user may again be the landlord with respect to remote control functionality. While the identity of the person performing the action may be germane to a particular advantage provided by one or more of the implementations, such an identity should not be construed in the descriptions that follow as necessarily limiting the scope of the present teachings to those particular individuals having those particular identities.

The depicted structure 150 includes a plurality of rooms 152, separated at least partly from each other via walls 154. The walls 154 may include interior walls or exterior walls. Each room may further include a floor 156 and a ceiling 158. Devices may be mounted on, integrated with and/or supported by a wall 154, floor 156, or ceiling 158.

In some implementations, the integrated devices of the smart-home environment 100 include intelligent, multi-sensing, network-connected devices that integrate seamlessly with each other in a smart-home network and/or with a central server or a cloud-computing system to provide a variety of useful smart-home functions. The smart-home environment 100 may include one or more intelligent, multi-sensing, network-connected thermostats 102 (hereinafter referred to as "smart thermostats 102"), one or more intelligent, network-connected, multi-sensing hazard detection units 104 (hereinafter referred to as "smart hazard detectors 104"), one or more intelligent, multi-sensing, network-connected entryway interface devices 106 and 120 (hereinafter referred to as "smart doorbells 106" and "smart door locks 120"), and one or more intelligent, multi-sensing, network-connected alarm systems 122 (hereinafter referred to as "smart alarm systems 122"). Although not depicted explicitly in FIG. 1, the smart-home environment 100 may also include other monitoring systems, such as baby monitoring systems, elderly monitoring systems, handicapped monitoring systems, and so forth.

In some implementations, the one or more smart thermostats 102 detect ambient climate characteristics (e.g., temperature and/or humidity) and control a HVAC system 103 accordingly. For example, a respective smart thermostat 102 includes an ambient temperature sensor.

The one or more smart hazard detectors 104 may include thermal radiation sensors directed at respective heat sources (e.g., a stove, oven, other appliances, a fireplace, etc.). For example, a smart hazard detector 104 in a kitchen 153 may include a thermal radiation sensor directed at a stove/oven 112. A thermal radiation sensor may determine the temperature of the respective heat source (or a portion thereof) at which it is directed and may provide corresponding blackbody radiation data as output.

The smart doorbell 106 and/or the smart door lock 120 may detect a person's approach to or departure from a location (e.g., an outer door), control doorbell/door locking functionality (e.g., receive user inputs from a portable electronic device 166-1 to actuate bolt of the smart door lock 120), announce a person's approach or departure via audio or visual devices, and/or control settings on a security system (e.g., to activate or deactivate the security system when occupants go and come). In some implementations, the smart doorbell 106 may include some or all of the components and features of the camera 118. In some implementations, the smart doorbell 106 includes a camera 118.

The smart alarm system 122 may detect the presence of an individual within close proximity (e.g., using built-in IR sensors), sound an alarm (e.g., through a built-in speaker, or by sending commands to one or more external speakers), and send notifications to entities or users within/outside of the smart-home network 100. In some implementations, the smart alarm system 122 also includes one or more input devices or sensors (e.g., keypad, biometric scanner, NFC transceiver, microphone) for verifying the identity of a user, and one or more output devices (e.g., display, speaker) for providing notifications. In some implementations, the smart alarm system 122 may also be set to an "armed" mode, such that detection of a trigger condition or event causes the alarm to be sounded unless a disarming action is performed.

In some implementations, the smart-home environment 100 may include one or more intelligent, multi-sensing, network-connected wall switches 108 (hereinafter referred to as "smart wall switches 108"), along with one or more intelligent, multi-sensing, network-connected wall plug interfaces 110 (hereinafter referred to as "smart wall plugs 110"). The smart wall switches 108 may detect ambient lighting conditions, detect room-occupancy states, and control a power and/or dim state of one or more lights. In some instances, smart wall switches 108 may also control a power state or speed of a fan, such as a ceiling fan. The smart wall plugs 110 may detect occupancy of a room or enclosure and control supply of power to one or more wall plugs (e.g., such that power is not supplied to the plug if nobody is at home).

In some implementations, the smart-home environment 100 of FIG. 1 may include a plurality of intelligent, multi-sensing, network-connected appliances 112 (hereinafter referred to as "smart appliances 112"), such as refrigerators, stoves, ovens, televisions, washers, dryers, lights, stereos, intercom systems, garage-door openers, floor fans, ceiling fans, wall air conditioners, pool heaters, irrigation systems, security systems, space heaters, window AC units, motorized duct vents, and so forth. In some implementations, when plugged in, an appliance may announce itself to the smart home network, such as by indicating what type of appliance it is, and it may automatically integrate with the controls of the smart home. Such communication by the appliance to the smart home may be facilitated by either a wired or wireless communication protocol. The smart home may also include a variety of non-communicating legacy appliances 140, such as older-model conventional washers/dryers, refrigerators, and/or the like, which may be controlled by smart wall plugs 110. The smart-home environment 100 may further include a variety of partially communicating legacy appliances 142, such as infrared ("IR") controlled wall air conditioners or other IR-controlled devices, which may be controlled by IR signals provided by the smart hazard detectors 104, hand-held remote controls, key FOBs, or the smart wall switches 108.

In some implementations, the smart-home environment 100 may include one or more network-connected cameras 118 that are configured to provide video monitoring and security in the smart-home environment 100. The cameras 118 may be used to determine the occupancy of the structure 150 and/or particular rooms 152 in the structure 150, and thus may act as occupancy sensors. For example, video captured by the cameras 118 may be processed to identify the presence of an occupant in the structure 150 (e.g., in a particular room 152). Specific individuals may be identified based, for example, on their appearance (e.g., height, face) and/or movement (e.g., their walk/gait). Cameras 118 may additionally include one or more sensors (e.g., IR sensors, motion detectors), input devices (e.g., microphone for capturing audio), and output devices (e.g., speaker for outputting audio). In some implementations, the cameras 118 may each be configured to operate in a day mode and in a low-light mode (e.g., a night mode). In some implementations, the cameras 118 each include one or more IR illuminators for providing illumination while the camera is operating in the low-light mode. In some implementations, the cameras 118 include one or more outdoor cameras. In some implementations, the outdoor cameras include additional features and/or components such as weatherproofing and/or solar ray compensation.

The smart-home environment 100 may additionally or alternatively include one or more other occupancy sensors (e.g., the smart doorbell 106, smart door locks 120, touch screens, IR sensors, microphones, ambient light sensors, motion detectors, smart nightlights 170, etc.). In some implementations, the smart-home environment 100 may include radio-frequency identification (RFID) readers (e.g., in each room 152 or a portion thereof) that determine occupancy based on RFID tags located on or embedded in occupants. For example, RFID readers may be integrated into the smart hazard detectors 104, and RFID tags may be worn in users clothing for integrated in hand-held devices such as a smart phone.

The smart-home environment 100 may also include communication with devices outside of the physical home but within a proximate geographical range of the home. For example, the smart-home environment 100 may include a pool heater monitor 114 that communicates a current pool temperature to other devices within the smart-home environment 100 and/or receives commands for controlling the pool temperature. Similarly, the smart-home environment 100 may include an irrigation monitor 116 that communicates information regarding irrigation systems within the smart-home environment 100 and/or receives control information for controlling such irrigation systems.

By virtue of network connectivity, one or more of the smart home devices of FIG. 1 may further allow a user to interact with the device even if the user is not proximate to the device. For example, a user may communicate with a device using a computer (e.g., a desktop computer, laptop computer, or tablet) or other portable electronic device 166 (e.g., a mobile phone, such as a smart phone). A webpage or application may be configured to receive communications from the user and control the device based on the communications and/or to present information about the device's operation to the user. For example, the user may view a current set point temperature for a device (e.g., a stove) and adjust it using a computer. The user may be in the structure during this remote communication or outside the structure.

As discussed above, users may control smart devices in the smart-home environment 100 using a network-connected computer or portable electronic device 166. In some examples, some or all of the occupants (e.g., individuals who live in the home) may register their device 166 with the smart-home environment 100. Such registration may be made at a central server to authenticate the occupant and/or the device as being associated with the home and to give permission to the occupant to use the device to control the smart devices in the home. An occupant may use their registered device 166 to remotely control the smart devices of the home, such as when the occupant is at work or on vacation. The occupant may also use their registered device to control the smart devices when the occupant is actually located inside the home, such as when the occupant is sitting on a couch inside the home. It should be appreciated that instead of or in addition to registering devices 166, the smart-home environment 100 may make inferences about (1) which individuals live in the home and are therefore occupants, and (2) which devices 166 are associated with those individuals. As such, the smart-home environment may "learn" who is an occupant and permit the devices 166 associated with those individuals to control the smart devices of the home.

In some implementations, in addition to containing processing and sensing capabilities, devices 102, 104, 106, 108, 110, 112, 114, 116, 118, 120, and/or 122 (collectively referred to as "the smart devices" or "the smart-home devices") are capable of data communications and information sharing with other smart devices, a central server or cloud-computing system, and/or other devices that are network-connected. Data communications may be carried out using any of a variety of custom or standard wireless protocols (e.g., IEEE 802.15.4, Wi-Fi, ZigBee, 6LoWPAN, Thread, Z-Wave, Bluetooth Smart, ISA100.5A, WirelessHART, MiWi, etc.) and/or any of a variety of custom or standard wired protocols (e.g., Ethernet, HomePlug, etc.), or any other suitable communication protocol, including communication protocols not yet developed as of the filing date of this document.

In some implementations, the smart devices may serve as wireless or wired repeaters. In some implementations, a first one of the smart devices communicates with a second one of the smart devices via a wireless router. The smart devices may further communicate with each other via a connection (e.g., network interface 160) to a network, such as the Internet 162. Through the Internet 162, the smart devices may communicate with a server system 164 (also called a central server system and/or a cloud-computing system herein). The server system 164 may be associated with a manufacturer, support entity, or service provider associated with the smart device(s). In some implementations, a user is able to contact customer support using a smart device itself rather than needing to use other communication means, such as a telephone or Internet-connected computer. In some implementations, software updates are automatically sent from the server system 164 to smart devices (e.g., when available, when purchased, or at routine intervals).

In some implementations, the network interface 160 includes a conventional network device (e.g., a router), and the smart-home environment 100 of FIG. 1 includes a hub device 180 that is communicatively coupled to the network (s) 162 directly or via the network interface 160. The hub device 180 may be further communicatively coupled to one or more of the above intelligent, multi-sensing, network-connected devices (e.g., smart devices of the smart-home environment 100). Each of these smart devices optionally communicates with the hub device 180 using one or more radio communication networks available at least in the smart-home environment 100 (e.g., ZigBee, Z-Wave, Insteon, Bluetooth, Wi-Fi and other radio communication networks). In some implementations, the hub device 180 and devices coupled with/to the hub device can be controlled and/or interacted with via an application running on a smart phone, household controller, laptop, tablet computer, game console or similar electronic device. In some implementations, a user of such controller application can view status of the hub device or coupled smart devices, configure the hub device to interoperate with smart devices newly introduced to the home network, commission new smart devices, and adjust or view settings of connected smart devices, etc. In some implementations the hub device extends the capabilities of low-capability smart devices to match the capabilities of the highly capable smart devices of the same type, integrates functionality of multiple different device types— even across different communication protocols, and is configured to streamline adding of new devices and commissioning of the hub device. In some implementations, hub device 180 further comprises a local storage device for storing data related to, or output by, smart devices of smart-home environment 100. In some implementations, the data includes one or more of: video data output by a camera device, metadata output by a smart device, settings information for a smart device, usage logs for a smart device, and the like.

In some implementations, smart-home environment 100 includes a local storage device 190 for storing data related to, or output by, smart devices of smart-home environment 100. In some implementations, the data includes one or more of: video data output by a camera device (e.g., camera 118), metadata output by a smart device, settings information for a smart device, usage logs for a smart device, and the like. In some implementations, local storage device 190 is communicatively coupled to one or more smart devices via a smart home network. In some implementations, local storage device 190 is selectively coupled to one or more smart devices via a wired and/or wireless communication network. In some implementations, local storage device 190 is used to store video data when external network conditions are poor. For example, local storage device 190 is used when an encoding bitrate of camera 118 exceeds the available bandwidth of the external network (e.g., network(s) 162). In some implementations, local storage device 190 temporarily stores video data from one or more cameras (e.g., camera 118) prior to transferring the video data to a server system (e.g., server system 164).

In some implementations, the smart-home environment 100 includes service robots 168 that are configured to carry out, in an autonomous manner, any of a variety of household tasks.

Figure 2A:
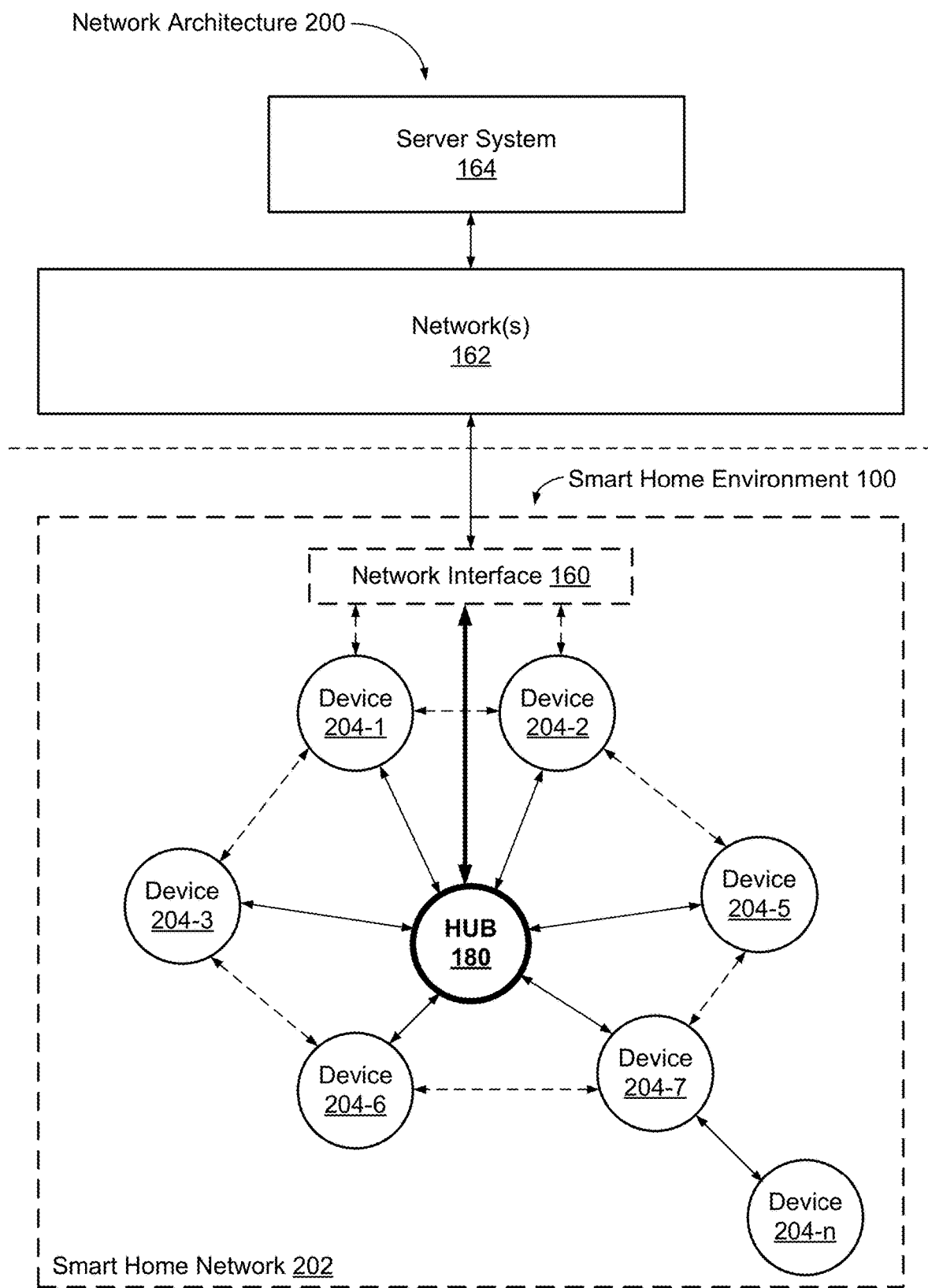
FIG. 2A illustrates a simplified block diagram of a representative network architecture that includes a smart-home network in accordance, according to some embodiments.

FIG. 2A illustrates a simplified block diagram of a representative network architecture 200 that includes a smart home network 202 in accordance with some implementations. In some implementations, the smart devices 204 in the smart-home environment 100 (e.g., devices 102, 104, 106, 108, 110, 112, 114, 116, 118, 120, and/or 122) combine with the hub device 180 to create a mesh network in smart home network 202. In some implementations, one or more smart devices 204 in the smart home network 202 operate as a smart home controller. Additionally and/or alternatively, hub device 180 operates as the smart home controller. In some implementations, a smart home controller has more computing power than other smart devices. In some implementations, a smart home controller processes inputs (e.g., from smart devices 204, electronic device 166, and/or server system 164) and sends commands (e.g., to smart devices 204 in the smart home network 202) to control operation of the smart-home environment 100. In some implementations, some of the smart devices 204 in the smart home network 202 (e.g., in the mesh network) are "spokesman" nodes (e.g., 204-1) and others are "low-powered" nodes (e.g., 204-9). Some of the smart devices in the smart-home environment 100 are battery powered, while others have a regular and reliable power source, such as by connecting to wiring (e.g., to 120V line voltage wires) behind the walls 154 of the smart-home environment. The smart devices that have a regular and reliable power source are referred to as "spokesman" nodes. These nodes are typically equipped with the capability of using a wireless protocol to facilitate bidirectional communication with a variety of other devices in the smart-home environment 100, as well as with the server system 164. In some implementations, one or more "spokesman" nodes operate as a smart home controller. On the other hand, the devices that are battery powered are the "low-power" nodes. These nodes tend to be smaller than spokesman nodes and typically only communicate using wireless protocols that require very little power, such as Zigbee, ZWave, 6LoWPAN, Thread, Bluetooth, etc.

In some implementations, some low-power nodes may be incapable of bidirectional communication. These low-power nodes may send messages, but they are unable to "listen." Thus, other devices in the smart-home environment 100, such as the spokesman nodes, need not send information to these low-power nodes. In some implementations, some low-power nodes are capable of only a limited bidirectional communication. For example, other devices are able to communicate with the low-power nodes only during a certain time period.

In some implementations, the smart devices may serve as low-power and spokesman nodes to create a mesh network in the smart-home environment 100. In some implementations, individual low-power nodes in the smart-home environment may regularly send out messages regarding what they are sensing, and the other low-powered nodes in the smart-home environment—in addition to sending out their own messages—may forward these messages, thereby causing the messages to travel from node to node (i.e., device to device) throughout the smart home network 202. In some implementations, the spokesman nodes in the smart home network 202, which are able to communicate using a relatively high-power communication protocol, such as IEEE 802.11, are able to switch to a relatively low-power communication protocol, such as IEEE 802.15.4, to receive these messages, translate the messages to other communication protocols, and send the translated messages to other spokesman nodes and/or the server system 164 (using, e.g., the relatively high-power communication protocol). Thus, the low-powered nodes using low-power communication protocols are able to send and/or receive messages across the entire smart home network 202, as well as over the Internet 162 to the server system 164. In some implementations, the mesh network enables the server system 164 to regularly receive data from most or all of the smart devices in the home, make inferences based on the data, facilitate state synchronization across devices within and outside of the smart home network 202, and send commands to one or more of the smart devices to perform tasks in the smart-home environment.

The spokesman nodes and some of the low-powered nodes are capable of "listening." Accordingly, users, other devices, and/or the server system 164 may communicate control commands to the low-powered nodes. For example, a user may use the electronic device 166 (e.g., a smart phone) to send commands over the Internet to the server system 164, which then relays the commands to one or more spokesman nodes in the smart home network 202. The spokesman nodes may use a low-power protocol to communicate the commands to the low-power nodes throughout the smart home network 202, as well as to other spokesman nodes that did not receive the commands directly from the server system 164.

In some implementations, a smart nightlight 170, which is an example of a smart device 204, is a low-power node. In addition to housing a light source, the smart nightlight 170 houses an occupancy sensor, such as an ultrasonic or passive IR sensor, and an ambient light sensor, such as a photo resistor or a single-pixel sensor that measures light in the room. In some implementations, the smart nightlight 170 is configured to activate the light source when its ambient light sensor detects that the room is dark and when its occupancy sensor detects that someone is in the room. In other implementations, the smart nightlight 170 is simply configured to activate the light source when its ambient light sensor detects that the room is dark. Further, in some implementations, the smart nightlight 170 includes a low-power wireless communication chip (e.g., a ZigBee chip) that regularly sends out messages regarding the occupancy of the room and the amount of light in the room, including instantaneous messages coincident with the occupancy sensor detecting the presence of a person in the room. As described above, these messages may be sent wirelessly (e.g., using the mesh network) from node to node (i.e., smart device to smart device) within the smart home network 202 as well as over the Internet 162 to the server system 164.

Other examples of low-power nodes include battery-operated versions of the smart hazard detectors 104. These smart hazard detectors 104 are often located in an area without access to constant and reliable power and may include any number and type of sensors, such as smoke/fire/heat sensors (e.g., thermal radiation sensors), carbon monoxide/dioxide sensors, occupancy/motion sensors, ambient light sensors, ambient temperature sensors, humidity sensors, and the like. Furthermore, smart hazard detectors 104 may send messages that correspond to each of the respective sensors to the other devices and/or the server system 164, such as by using the mesh network as described above.

Examples of spokesman nodes include smart doorbells 106, smart thermostats 102, smart wall switches 108, and smart wall plugs 110. These devices are often located near and connected to a reliable power source, and therefore may include more power-consuming components, such as one or more communication chips capable of bidirectional communication in a variety of protocols.

As explained above with reference to FIG. 1, in some implementations, the smart-home environment 100 of FIG. 1 includes a hub device 180 that is communicatively coupled to the network(s) 162 directly or via the network interface 160. The hub device 180 is further communicatively coupled to one or more of the smart devices using a radio communication network that is available at least in the smart-home environment 100. Communication protocols used by the radio communication network include, but are not limited to, ZigBee, Z-Wave, Insteon, EuOcean, Thread, OSIAN, Bluetooth Low Energy and the like. In some implementations, the hub device 180 not only converts the data received from each smart device to meet the data format requirements of the network interface 160 or the network(s) 162, but also converts information received from the network interface 160 or the network(s) 162 to meet the data format requirements of the respective communication protocol associated with a targeted smart device. In some implementations, in addition to data format conversion, the hub device 180 further processes the data received from the smart devices or information received from the network interface 160 or the network(s) 162 preliminary. For example, the hub device 180 can integrate inputs from multiple sensors/connected devices (including sensors/devices of the same and/or different types), perform higher level processing on those inputs—e.g., to assess the overall environment and coordinate operation among the different sensors/devices—and/or provide instructions to the different devices based on the collection of inputs and programmed processing. It is also noted that in some implementations, the network interface 160 and the hub device 180 are integrated to one network device. Functionality described herein is representative of particular implementations of smart devices, control application(s) running on representative electronic device(s) (such as a smart phone), hub device(s) 180, and server(s) coupled to hub device(s) via the Internet or other Wide Area Network (WAN). All or a portion of this functionality and associated operations can be performed by any elements of the described system—for example, all or a portion of the functionality described herein as being performed by an implementation of the hub device can be performed, in different system implementations, in whole or in part on the server, one or more connected smart devices and/or the control application, or different combinations thereof.

Figure 2B:
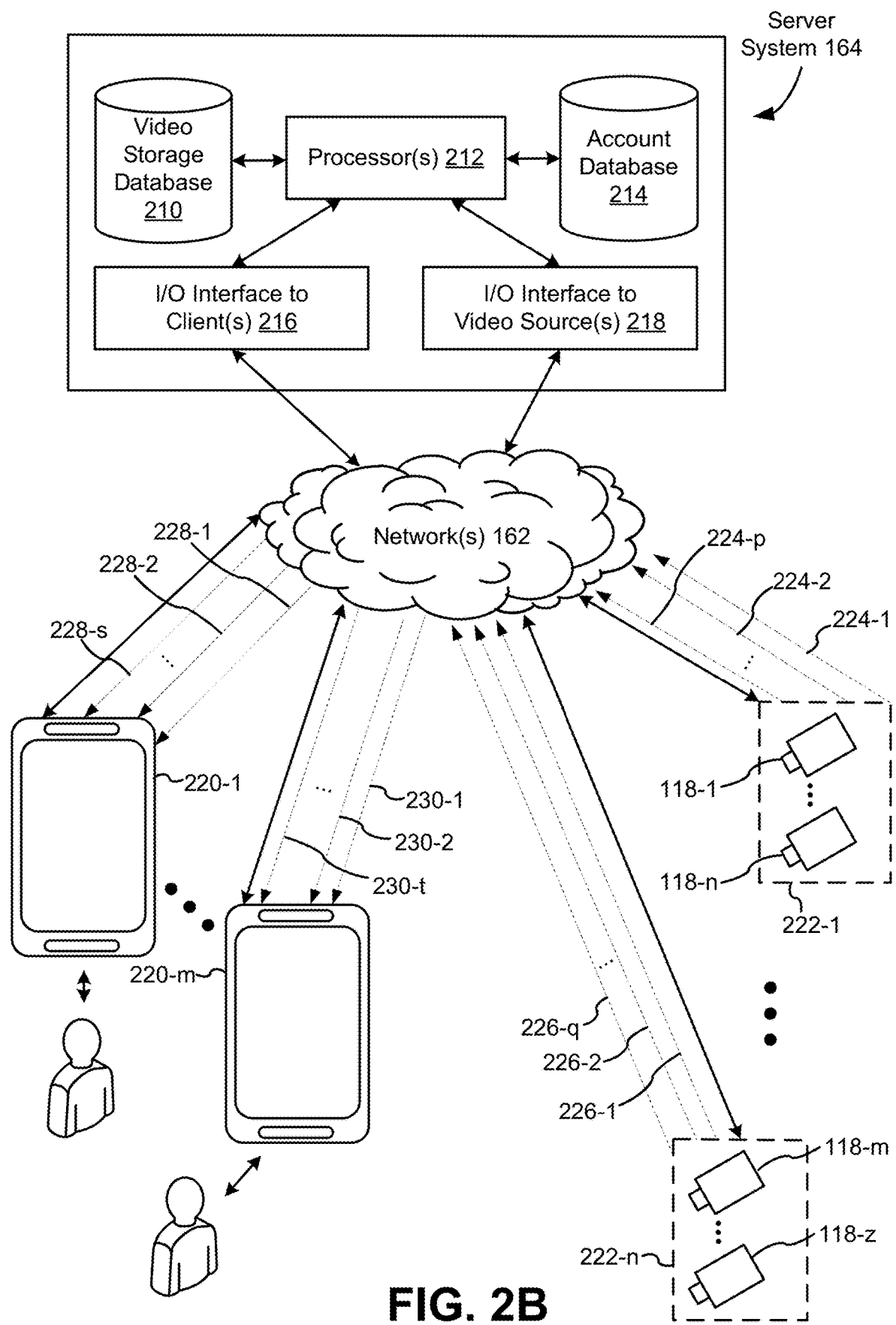
FIG. 2B illustrates a simplified operating environment in which a server system interacts with client devices and smart devices, according to some embodiments.

FIG. 2B illustrates a representative operating environment in which a server system 164 provides data processing for monitoring and facilitating review of events (e.g., motion, audio, security, etc.) in video streams captured by video cameras 118. As shown in FIG. 2B, the server system 164 receives video data from video sources 222 (including cameras 118) located at various physical locations (e.g., inside homes, restaurants, stores, streets, parking lots, and/or the smart-home environments 100 of FIG. 1). Each video source 222 may be bound to one or more reviewer accounts, and the server system 164 provides video monitoring data for the video source 222 to client devices 220 associated with the reviewer accounts. For example, the portable electronic device 166 is an example of the client device 220. In some implementations, the server system 164 is a video processing server that provides video processing services to video sources and client devices 220.

In some implementations, each of the video sources 222 includes one or more video cameras 118 that capture video and send the captured video to the server system 164 substantially in real-time. In some implementations, each of the video sources 222 includes a controller device (not shown) that serves as an intermediary between the one or more cameras 118 and the server system 164. The controller device receives the video data from the one or more cameras 118, optionally performs some preliminary processing on the video data, and sends the video data to the server system 164 on behalf of the one or more cameras 118 substantially in real-time. In some implementations, each camera has its own on-board processing capabilities to perform some preliminary processing on the captured video data before sending the processed video data (along with metadata obtained through the preliminary processing) to the controller device and/or the server system 164.

In accordance with some implementations, each of the client devices 220 includes a client-side module. The client-side module communicates with a server-side module executed on the server system 164 through the one or more networks 162. The client-side module provides client-side functionality for the event monitoring and review processing and communications with the server-side module. The server-side module provides server-side functionality for event monitoring and review processing for any number of client-side modules each residing on a respective client device 220. The server-side module also provides server-side functionality for video processing and camera control for any number of the video sources 222, including any number of control devices and the cameras 118.

In some implementations, the server system 164 includes one or more processors 212, a video storage database 210, an account database 214, an I/O interface to one or more client devices 216, and an I/O interface to one or more video sources 218. The I/O interface to one or more clients 216 facilitates the client-facing input and output processing. The account database 214 stores a plurality of profiles for reviewer accounts registered with the video processing server, where a respective user profile includes account credentials for a respective reviewer account, and one or more video sources linked to the respective reviewer account. The I/O interface to one or more video sources 218 facilitates communications with one or more video sources 222 (e.g., groups of one or more cameras 118 and associated controller devices). The video storage database 210 stores raw video data received from the video sources 222, as well as various types of metadata, such as motion events, event categories, event category models, event filters, and event masks, for use in data processing for event monitoring and review for each reviewer account.

Examples of a representative client device 220 include a handheld computer, a wearable computing device, a personal digital assistant (PDA), a tablet computer, a laptop computer, a desktop computer, a cellular telephone, a smart phone, an enhanced general packet radio service (EGPRS) mobile phone, a media player, a navigation device, a game console, a television, a remote control, a point-of-sale (POS) terminal, a vehicle-mounted computer, an eBook reader, or a combination of any two or more of these data processing devices or other data processing devices.

Examples of the one or more networks 162 include local area networks (LAN) and wide area networks (WAN) such as the Internet. The one or more networks 162 are implemented using any known network protocol, including various wired or wireless protocols, such as Ethernet, Universal Serial Bus (USB), FIREWIRE, Long Term Evolution (LTE), Global System for Mobile Communications (GSM), Enhanced Data GSM Environment (EDGE), code division multiple access (CDMA), time division multiple access (TDMA), Bluetooth, Wi-Fi, voice over Internet Protocol (VoIP), Wi-MAX, or any other suitable communication protocol.

In some implementations, the server system 164 may be implemented on one or more standalone data processing apparatuses or a distributed network of computers. In some implementations, the server system 164 also employs various virtual devices and/or services of third party service providers (e.g., third-party cloud service providers) to provide the underlying computing resources and/or infrastructure resources of the server system 164. In some implementations, the server system 164 includes, but is not limited to, a server computer, a handheld computer, a tablet computer, a laptop computer, a desktop computer, or a combination of any two or more of these data processing devices or other data processing devices.

The server-client environment shown in FIG. 2B includes both a client-side portion (e.g., the client-side module) and a server-side portion (e.g., the server-side module). The division of functionality between the client and server portions of operating environment can vary in different implementations. Similarly, the division of functionality between a video source 222 and the server system 164 can vary in different implementations. For example, in some implementations, the client-side module is a thin-client that provides only user-facing input and output processing functions, and delegates all other data processing functionality to a backend server (e.g., the server system 164). Similarly, in some implementations, a respective one of the video sources 222 is a simple video capturing device that continuously captures and streams video data to the server system 164 with limited or no local preliminary processing on the video data. Although many aspects of the present technology are described from the perspective of the server system 164, the corresponding actions performed by a client device 220 and/or the video sources 222 would be apparent to one of skill in the art. Similarly, some aspects of the present technology may be described from the perspective of a client device or a video source, and the corresponding actions performed by the video server would be apparent to one of skill in the art. Furthermore, some aspects of the present technology may be performed by the server system 164, a client device 220, and a video source 222 cooperatively.

In some implementations, a video source 222 (e.g., a camera 118) transmits one or more streams of video data to the server system 164. In some implementations, the one or more streams may include multiple streams, of respective resolutions and/or frame rates, of the raw video captured by the camera 118. In some implementations, the multiple streams may include a "primary" stream with a certain resolution and frame rate, corresponding to the raw video captured by the camera 118, and one or more additional streams. An additional stream may be the same video stream as the "primary" stream but at a different resolution and/or frame rate, or a stream that captures a portion of the "primary" stream (e.g., cropped to include a portion of the field of view or pixels of the primary stream) at the same or different resolution and/or frame rate as the "primary" stream.

Figure 4:
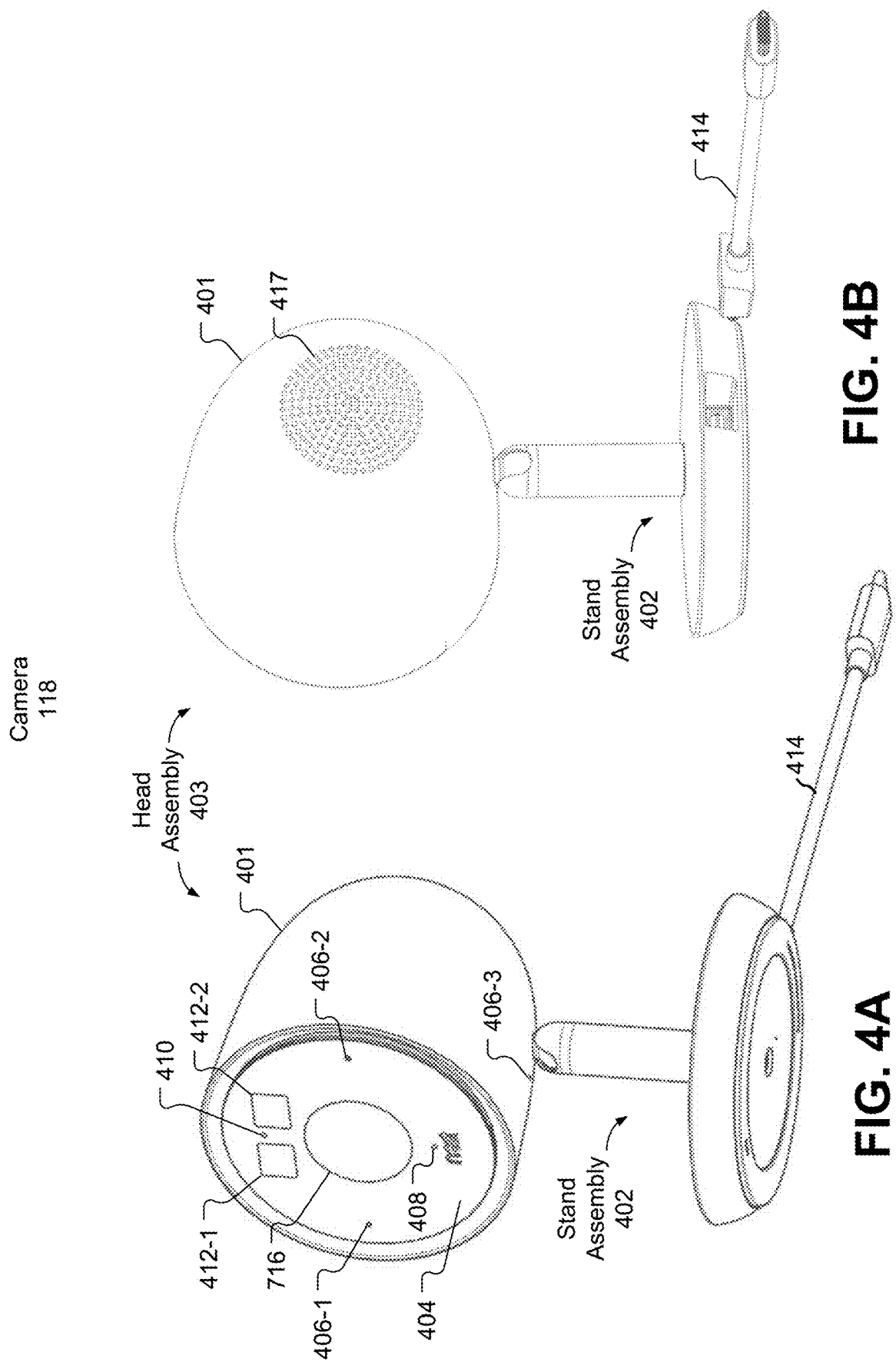
FIG. 4A illustrates a view of a representative camera assembly in accordance with some implementations.
FIG. 4B illustrates a view of a representative camera assembly in accordance with some implementations.

In some implementations, one or more of the streams are sent from the video source 222 directly to a client device 220 (e.g., without being routed to, or processed by, the server system 164). In some implementations, one or more of the streams is stored at the camera 118 (e.g., in memory 406, FIG. 4) and/or a local storage device (e.g., a dedicated recording device), such as a digital video recorder (DVR). For example, in accordance with some implementations, the camera 118 stores the most recent 24 hours of video footage recorded by the camera. In some implementations, portions of the one or more streams are stored at the camera 118 and/or the local storage device (e.g., portions corresponding to particular events or times of interest).

In some implementations, the server system 164 transmits one or more streams of video data to a client device 220 to facilitate event monitoring by a user. In some implementations, the one or more streams may include multiple streams, of respective resolutions and/or frame rates, of the same video feed. In some implementations, the multiple streams may include a "primary" stream with a certain resolution and frame rate, corresponding to the video feed, and one or more additional streams. An additional stream may be the same video stream as the "primary" stream but at a different resolution and/or frame rate, or a stream that shows a portion of the "primary" stream (e.g., cropped to include portion of the field of view or pixels of the primary stream) at the same or different resolution and/or frame rate as the "primary" stream, as described in greater detail in U.S. patent application Ser. No. 15/594,518, which is incorporated herein by reference.

Figure 3:
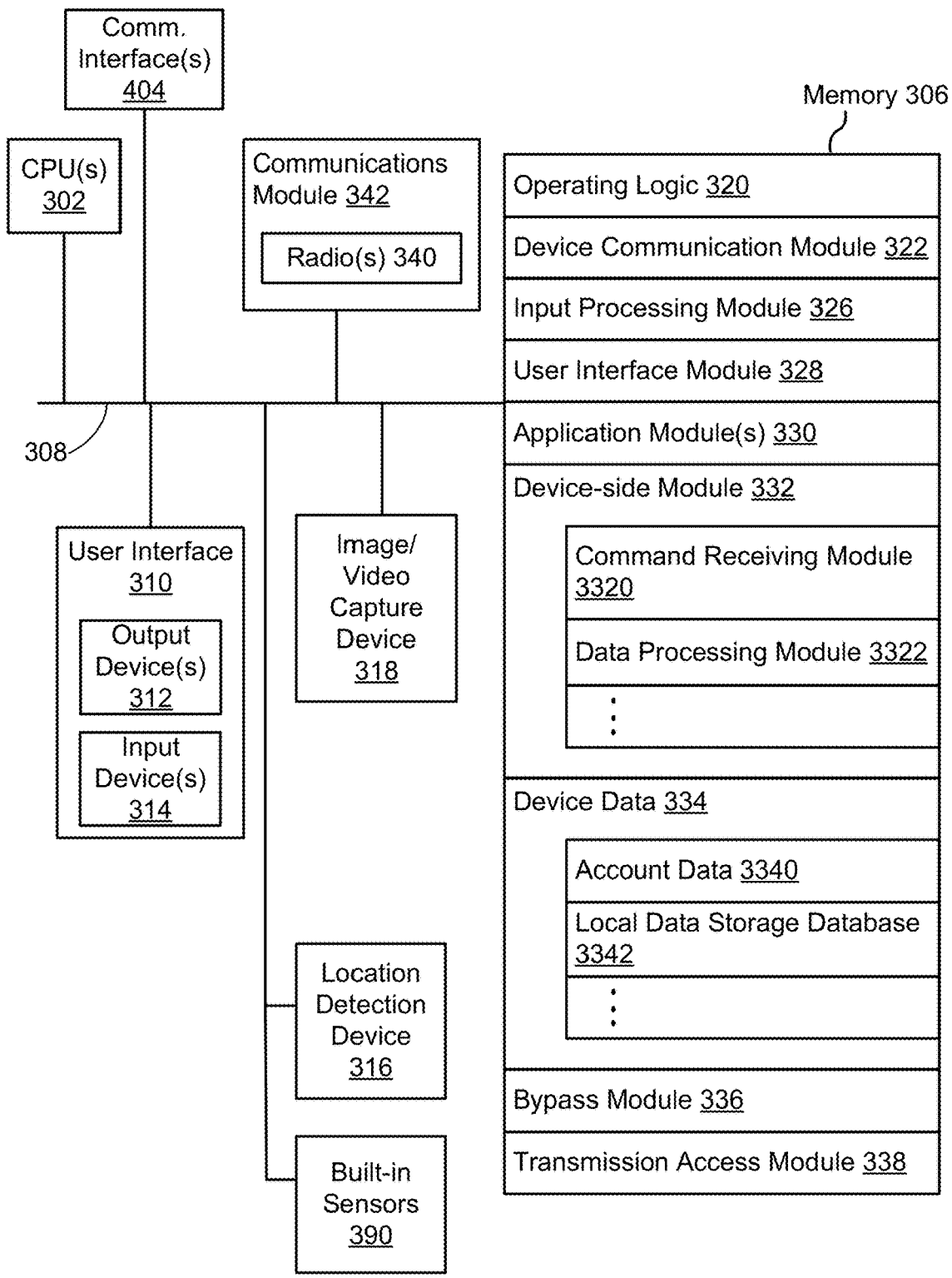
FIG. 3 illustrates a block diagram of a representative smart device in accordance with some implementations.

FIG. 3 illustrates a block diagram of a representative smart device 204 in accordance with some implementations. In some implementations, the smart device 204 (e.g., any devices of a smart-home environment 100, FIG. 1) includes one or more processing units (e.g., CPUs, ASICs, FPGAs, microprocessors, and the like) 302, one or more communication interfaces 304, memory 306, communications module 342 with radios 340, and one or more communication buses 308 for interconnecting these components (sometimes called a chipset). In some implementations, the user interface 310 includes one or more output devices 312 that enable presentation of media content, including one or more speakers and/or one or more visual displays. In some implementations, the user interface 310 also includes one or more input devices 314, including user interface components that facilitate user input such as a keyboard, a mouse, a voice-command input unit or microphone, a touch screen display, a touch-sensitive input pad, a gesture capturing camera, or other input buttons or controls. Furthermore, some smart devices 204 use a microphone and voice recognition or a camera and gesture recognition to supplement or replace the keyboard. In some implementations, the smart device 204 includes one or more image/video capture devices 318 (e.g., cameras, video cameras, scanners, photo sensor units). The built-in sensors 390 may include, for example, one or more thermal radiation sensors, ambient temperature sensors, humidity sensors, IR sensors, occupancy sensors (e.g., using RFID sensors), ambient light sensors, motion detectors, accelerometers, and/or gyroscopes.

The radios 340 enable one or more radio communication networks in the smart-home environments, and allow a smart device 204 to communicate with other devices. In some implementations, the radios 340 are capable of data communications using any of a variety of custom or standard wireless protocols (e.g., IEEE 802.15.4, Wi-Fi, ZigBee, 6LoWPAN, Thread, Z-Wave, Bluetooth Smart, ISA100.5A, WirelessHART, MiWi, etc.) custom or standard wired protocols (e.g., Ethernet, HomePlug, etc.), and/or any other suitable communication protocol, including communication protocols not yet developed as of the filing date of this document.

The communication interfaces 304 include, for example, hardware capable of data communications using any of a variety of custom or standard wireless protocols (e.g., IEEE 802.15.4, Wi-Fi, ZigBee, 6LoWPAN, Thread, Z-Wave, Bluetooth Smart, ISA100.5A, WirelessHART, MiWi, etc.) and/or any of a variety of custom or standard wired protocols (e.g., Ethernet, HomePlug, etc.), or any other suitable communication protocol, including communication protocols not yet developed as of the filing date of this document.

The memory 306 includes high-speed random access memory, such as DRAM, SRAM, DDR RAM, or other random access solid state memory devices; and, optionally, includes non-volatile memory, such as one or more magnetic disk storage devices, one or more optical disk storage devices, one or more flash memory devices, or one or more other non-volatile solid state storage devices. The memory 306, or alternatively the non-volatile memory within the memory 306, includes a non-transitory computer readable storage medium. In some implementations, the memory 306, or the non-transitory computer readable storage medium of the memory 306, stores the following programs, modules, and data structures, or a subset or superset thereof: operating logic 320 including procedures for handling various basic system services and for performing hardware dependent tasks; a device communication module 322 for connecting to and communicating with other network devices (e.g., network interface 160, such as a router that provides Internet connectivity, networked storage devices, network routing devices, server system 164, etc.) connected to one or more networks 162 via one or more communication interfaces 304 (wired or wireless); an input processing module 326 for detecting one or more user inputs or interactions from the one or more input devices 314 and interpreting the detected inputs or interactions; a user interface module 328 for providing and displaying a user interface in which settings, captured data, and/or other data for one or more devices (e.g., the smart device 204, and/or other devices in smart-home environment 100) can be configured and/or viewed; one or more applications 330 for execution by the smart device (e.g., games, social network applications, smart home applications, and/or other web or non-web based applications) for controlling devices (e.g., executing commands, sending commands, and/or configuring settings of the smart device 204 and/or other client/electronic devices), and for reviewing data captured by devices (e.g., device status and settings, captured data, or other information regarding the smart device 204 and/or other client/electronic devices); a device-side module 332, which provides device-side functionalities for device control, data processing and data review, including but not limited to: a command receiving module 3320 for receiving, forwarding, and/or executing instructions and control commands (e.g., from a client device 220, from a server system 164, from user inputs detected on the user interface 310, etc.) for operating the smart device 204; a data processing module 3322 for processing data captured or received by one or more inputs (e.g., input devices 314, image/video capture devices 318, location detection device 316), sensors (e.g., built-in sensors 390), interfaces (e.g., communication interfaces 304, radios 340), and/or other components of the smart device 204, and for preparing and sending processed data to a device for review (e.g., client devices 220 for review by a user); device data 334 storing data associated with devices (e.g., the smart device 204), including, but is not limited to: account data 3340 storing information related to user accounts loaded on the smart device 204, wherein such information includes cached login credentials, smart device identifiers (e.g., MAC addresses and UUIDs), user interface settings, display preferences, authentication tokens and tags, password keys, etc.; local data storage database 3342 for selectively storing raw or processed data associated with the smart device 204 (e.g., video surveillance footage captured by a camera 118); a bypass module 336 for detecting whether radio(s) 340 are transmitting signals via respective antennas coupled to the radio(s) 340 and to accordingly couple radio(s) 340 to their respective antennas either via a bypass line or an amplifier (e.g., a low noise amplifier); and a transmission access module 338 for granting or denying transmission access to one or more radio(s) 340 (e.g., based on detected control signals and transmission requests).

Each of the above identified elements may be stored in one or more of the previously mentioned memory devices, and corresponds to a set of instructions for performing a function described above. The above identified modules or programs (i.e., sets of instructions) need not be implemented as separate software programs, procedures, or modules, and thus various subsets of these modules may be combined or otherwise rearranged in various implementations. In some implementations, the memory 306, optionally, stores a subset of the modules and data structures identified above. Furthermore, the memory 306, optionally, stores additional modules and data structures not described above.

FIGS. 4A-4B are perspective views of a representative camera assembly in accordance with some implementations. FIG. 4A shows a first perspective view of a representative camera 118. As shown in FIG. 4A, the camera 118 includes a head assembly 403, a stand assembly 402, and a cable 414 (e.g., for powering the camera 118 and/or transferring data between the camera 118 and a second electronic device). The head assembly 403 includes a cover element 404 and a casing 401 (also sometimes called a housing). In accordance with some implementations, the cover element 404 has IR transparent portions 412 for IR illuminators, visible and IR transparent portion 416 for an image sensor, and semi-transparent portions 410 (corresponding to an ambient light sensor) and 408 (corresponding to a status LED). In accordance with some implementations, the cover element 404 also includes apertures 406 for microphones. In accordance with some implementations, the casing 401 includes an aperture 406-3 for a microphone.

In some implementations, the casing 401 has two or more layers. In some implementations, the inner layer is composed of a thermally conductive resin. In some implementations, the outer layer is a structural jacket configured to protect the camera 118 from environmental conditions such as moisture or electromagnetic charge (e.g., static electricity). In some implementations, the structural jacket is configured to protect the camera 118 from impacts, such as from a collision with another object or the ground.

FIG. 4B shows a back view of the camera 118. As shown in FIG. 4B the cable 414 is detachable from the stand assembly 402. For example, a user may store the cable 414 separately from the camera 118 when desired. In accordance with some implementations, the casing 401 includes a plurality of apertures 417 for a speaker.

Figure 5:
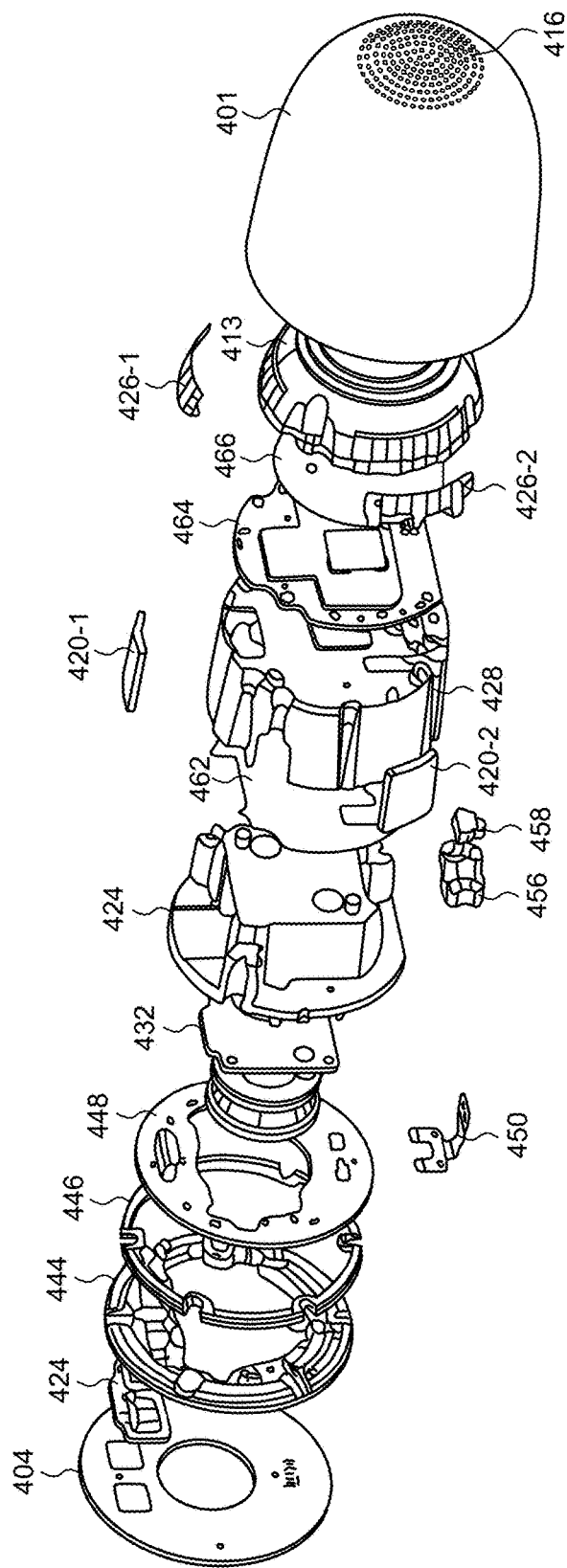
FIG. 5A is an expanded component view of a representative camera assembly in accordance with some implementations.
FIG. 5B is an expanded component view of a representative camera assembly in accordance with some implementations.

FIGS. 5A-5B are expanded component views of a representative camera assembly in accordance with some implementations. The camera 118 includes a cover element 404, an image sensor assembly 432, a speaker assembly 413, and a main circuit board 464. In some implementations, the speaker assembly 413 includes a speaker and a heat sink. In some implementations, the heat sink is configured to dissipate heat generated at the main board 464. In some implementations, the speaker assembly 413 acts as a heat sink for the camera's system-on-a-chip (SoC). In some implementations, the SoC is thermally coupled to the speaker assembly 413 with a thermal pad. In some implementations, the thermal pad's area is smaller than the speaker assembly's bottom surface 499. For optimal heat dissipation it is beneficial to spread the heat from the thermal pad over the entire bottom surface of the speaker assembly. In some implementations, a thermally graphite sheet (e.g., thermally conductive sheet 466) is used to achieve this spreading since graphite has very high in-plane thermal conductivity.

In some implementations, the camera 118 is a video streaming device with powerful computing capability embedded in the device. Therefore, in some instances, it will consume a lot of power and will also generate a lot of heat. In order to prevent the chipset and other components from being damaged by the heat, a thermal relief solution includes directing the heat from the CPU (e.g., a CPU of the SoC) to the speaker assembly 413. In some implementations, the speaker assembly 413 is composed of a thermally conductive plastic that is structurally suitable and has good heat spreading properties. In some implementations, a thermal pad on top of the shield can is used to direct the heat to the speaker assembly. To further distribute the heat onto the speaker, in some implementations, a graphite sheet is placed on the bottom surface of the speaker assembly. In some implementations, the size of the graphite sheet is maximized to achieve the best thermal relief function.

The camera 118 includes the cover element 404 having the IR transparent portions 412 for IR illuminators, the apertures 406 for microphones, the semi-transparent portion 408 corresponding to a status LED, and the semi-transparent portion 410 corresponding to an ambient light sensor. The camera 118 also includes a plurality of heat pads 420 for dissipating heat from the main board 464 and a thermal receiver structure 428 (e.g., having a shape like that of a fryer pot, hereinafter referred to as "fryer pot 428") to the casing 401, a plurality of antennas 426 for wirelessly communicating with other electronic devices, a thermal mount structure 424 (e.g., having a shape like that of a fryer basket, hereinafter referred to as "fryer basket 424") for dissipating and transferring heat from the image sensor assembly 432 to the cover element 404, and pads for thermally isolating the fryer basket 424 from the fryer pot 428.

In some implementations, the heat pads 420 are adapted to transfer heat from the fryer pot 428 to the casing 401. In some implementations, the heat pads 420 are adapted to thermally couple an inner layer of the casing 401 and the fryer pot 428. In some implementations, the heat pads are composed of a plastic. In some implementations, the heat pads are adapted to thermally de-couple the fryer basket 424 from the fryer pot 428. In some implementations, the fryer basket 424 is composed of magnesium. In some implementations, the fryer basket 424 is adapted to dissipate heat from the image sensor assembly 432. In some implementations, the fryer basket 424 is adapted to provide structural support to the camera 118. In some implementations, the fryer basket 424 is adapted to protect the image sensor assembly 432 from environmental forces such as moisture and/or impact from objects and/or the ground.

In some implementations, the antennas 426 are configured to operate concurrently using two distinct frequencies. In some implementations, the antennas 426 are configured to operate concurrently using two distinct communication protocols. In some implementations, one or more of the antennas 426 is configured for broadband communications (e.g., Wi-Fi) and/or point-to-point communications (e.g., Bluetooth). In some implementations, one or more of the antennas 426 is configured for mesh networking communications (e.g., ZWave). In some implementations, a first antenna 426 (e.g., antenna 426-1) is configured for 2.4 GHz Wi-Fi communication and a second antenna 426 (e.g., antenna 426-2) is configured for 5 GHz Wi-Fi communication. In some implementations, a first antenna 426 (e.g., antenna 426-1) is configured for 2.4 GHz Wi-Fi communication and point-to-point communication, a second antenna 426 (e.g., antenna 426-2) is configured for 5 GHz Wi-Fi communication and point-to-point communication, and a third antenna 426 (e.g., antenna 426-3) is configured for mesh networking communication. In some implementations, two or more of the antennas 426 are configured to transmit and/or receive data concurrently with others of the antennas 426. MIMO (multi input multi output) provides the benefit of greater throughput and better range for the wireless communication.

One of the parameters in the antenna system is the isolation between two antennas. Better isolation can ensure the data transmitted through two antennas are uncorrelated which is the key to the MIMO system. One way to achieve good isolation is to have large antenna separations. However, in modern consumer electronics the space left for antennas is very tight so having enough spacing between antennas is infeasible. While isolation is important, the antenna efficiency cannot be sacrificed. Isolation is directly related to how much energy is coupled from one antenna to another. The Friis equation defines the power received by another antenna as inversely proportional to $(1/R)^2$, where R is the distance between two antennas. So increasing antenna spacing is one effective way to achieve good isolation. Another means to achieve isolation is through use of a decoupling network. For example, an artificial coupling channel is generated in additional to its original coupling channel (e.g., which is through air). By properly managing the two coupling channels, the good isolation can be achieved.

In some implementations, the antennas 426 include at least one dual-band Inverted-F Antenna (IFA). In some implementations, the antennas are made by FPC, LDS, Stamping, or other state of art antenna manufacturing technology. In some implementations, the fryer pot 428 is a system ground for one or more of the antennas 426. In some implementations, the size of the antenna is about quarter-wavelength at 2.4 GHz. In some implementations, each antenna includes a radiating element, a feed line, and a ground stub. The ground stub presents an inductance to compensate for capacitance generated between the radiating element and the fryer pot 428. In some implementations, at least one of the antennas 426 includes a second ground stub.

The second ground stub is adapted to match the antenna to both 2.4 GHz and 5 GHz. In some implementations, the antenna feed is the feeding point for the 2.4 GHz and 5 GHz WiFi signal. In some implementations, the feed point is connected to the output of a WiFi chip. In some implementations, the antennas 426 include two identical IFA antennas. Both antennas are attached to the speaker assembly 413.

In some implementations, at least one of the antennas 426 includes a second type of antenna having first radiating element, a second radiating element, a first ground stub, and second ground stub. In some implementations, the size of the first radiating element is around quarter wavelength of 5 GHz. In some implementations, the resonance frequency at 2.4 GHz is determined by: (i) the size of the second radiating element, (ii) the position of the first ground stub, and (iii) the position of the second ground stub. In some implementations, the first ground stub is placed at a pistol end of the second radiating element. In some implementations, the second ground stub is between the first radiating element and the first ground stub. In some implementations, the position where second ground stub is attached to the second radiating element is adjusted to tune to the resonant frequency at 2.4 GHz. In some implementations, the first ground stub not only acts as part of the antenna, but also a shielding element that can reduce coupling coming from the left-handed side of the first ground stub. In some implementations, the second ground stub is also a shielding element to further reduce the coupling coming from the left handed side of the antenna. In some implementations, the second type of antenna includes more than 2 ground stubs. By using more ground stubs the antenna's physical size can be enlarged while maintaining the same resonant frequency (e.g., 2.4 GHz). In some implementations, the first and second ground stubs are on the right-handed side of the first radiating element to reduce coupling coming from the right-handed side. In some implementations, the antennas 426 include one or more antennas of a first type (e.g., IFAs) and one or more antennas of the second type.

By using a set of antennas including both a first type of antenna (e.g., an IFA) and the second type of antenna, two antennas can be positioned in a tight space while maintaining both good efficiency and good isolation between them. This enables the camera 118 to be compact without sacrificing the quality of wireless connectivity. In some implementations, both types of antennas are manufactured by conventional FPC technology with low cost. Unlike an antenna system relying on a decoupling system to achieve a similar isolation level, the IFA and second type antennas can be optimized and/or tuned independently.

The camera 118 may include the cover element 404, casing 401 with speaker holes 417, the image sensor assembly 432, and a speaker assembly 413. In some implementations, as shown, the speaker holes 417 extend directly outward from the speaker, which results in holes with an elliptical outer surface. In some implementations, the speaker holes 417 are parallel to one another. In some implementations, the speaker holes 417 extend outward at an angle consistent with the rear surface of the casing 401 such that the holes have a circular, rather than elliptical, outer surface (not shown). The camera 118 also includes a light guide 434 for directing light from a light assembly out the face of the camera 118.

The camera 118 includes an infrared (IR) reflector 442, a light diffuser 444, a light guide 446, a light ring 448, a microphone assembly 450, the image sensor assembly 432, the fryer basket 424, stand coupling elements 456 and 458, the fryer pot 428, a thermal insulator 462 adapted to thermally isolate the fryer pot 428 from the fryer basket 424, the main board 464, the thermally conductive sheet 466, the antennas 426, the speaker assembly 413, and the casing 401. In accordance with some implementations, the casing 401 has a lip 434 for reflecting and directing light from the light diffuser 444 outward from the face of the camera 118.

In some implementations, the cover element 404 comprises a chemically-strengthened glass. In some implementations, the cover element 404 comprises a soda-lime glass.

In some implementations, the image sensor assembly 432 includes a circuit board (e.g., a PCB board), an IR cut filter, a lens holder, and an image sensor. In some implementations, the image sensor comprises a 4 k image sensor. In some implementations, the image sensor comprises a 12 megapixel sensor. In some implementations, the image sensor comprises a wide-angle lens.

In some implementations, the thermally conductive sheet 466 is adapted to dissipate heat generated by the main board 464 and/or transfer heat from the main board 464 to the speaker assembly 413 for subsequent dissipation outside of the camera via the rear portion of the casing 401. In some implementations, the conductive sheet 466 is a graphite sheet. When a graphite sheet is placed near the antenna system with multiple antennas, it can create a coupling medium between antennas. The increased coupling caused by the graphite can decrease the isolation between two antennas, thus degrading antenna efficiency or causing permanent damage to the chipset.

In some implementations, the antennas 426 are configured to enable the camera 118 to wirelessly communication with one or more other electronic devices, such as a hub device 180, a smart device 204, and/or a server system 164.

In some implementations, the fryer pot 428 is composed of magnesium. In some implementations, the fryer pot 428 is adapted to provide structural support to the camera 118.

In some implementations, the fryer pot 428, the main board 464, the conductive sheet 466, the speaker assembly 413, and the antennas 426 comprise a rear sub-assembly. Thermally de-coupling the fryer basket 424 from the fryer pot 428 prevents heat generated by the main board 464 from interfering with the image sensor assembly 432. In accordance with some implementations, heat generated by the front of the main board 464 is transferred to the fryer pot 428 to the heat pads 420 and dissipated outside of the camera via the casing 401 (e.g., the sides of the casing). In accordance with some implementations, heat generated by the back of the main board 464 is transferred to the thermally conductive sheet 466 to the speaker assembly 413 and dissipated outside of the camera via the back portion of the casing 401.

In some implementations, the rear sub-assembly is affixed to the casing 401 via one or more fasteners (e.g., via 2-3 screws). In some implementations, the cover element 404, the infrared reflector 442, the light diffuser 444, the light guide 446, the light ring 448, and the image sensor assembly 432 comprise a front sub-assembly. In some implementations, the front sub-assembly is affixed to the casing 401 via one or more fasteners (e.g., 2-3 screws). In some implementations, the front sub-assembly is affixed to the rear sub-assembly via one or more fasteners.

In some implementations, the fryer basket 424 is adapted to dissipate heat generated by the image sensor assembly 432 and/or the light ring 448. In some implementations, the fryer basket 424 includes one or more forward-facing microphones. In some implementations, the downward-facing microphone 450 is operated in conjunction with the microphones on the fryer basket 424 to determine directionality and/or location of incoming sounds.

In some implementations, the IR reflector 442 is coated with an IR and/or visible light reflective coating. In some implementations, the IR reflector 442 is adapted to direct light from the IR illuminators 452 to a scene corresponding to a field of view of the image sensor assembly 432.

In some implementations, the light ring 448 comprises a plurality of visible light illuminators (e.g., RGB LEDs), a plurality of IR illuminators 452, and circuitry for powering and/or operating the visible light and/or IR illuminators. In some implementations, the light guide 446 is adapted to direct light from the visible light illuminators out the face of the camera 118. In some implementations, the light guide 446 is adapted to prevent light from the visible light illuminators from entering the image sensor assembly 432. In some implementations, the light guide 446 is adapted to spread the light from the visible light illuminators in a substantially even manner. In some implementations, the light guide 446 is composed of a clear material. In some implementations, the light guide 446 is composed of a poly-carbonite material. In some implementations, the light guide 446 has a plurality of dimples to refract the light from the illuminators and prevent the light from entering the image sensor assembly 432. In some implementations, the light guide 446 is adapted to provide more uniform color and light output to a user from the illuminators. In some implementations, the light guide 446 includes a plurality of segments, each segment corresponding to a visible light illuminator. In some implementations, the light guide 446 includes one or more light absorbing elements (e.g., black stickers) arranged between each segment to prevent light leakage from one illuminator segment to another illuminator segment.

In some implementations, the light diffuser 444 includes two or more sections (e.g., an inner section and an outer section). In some implementations, the light diffuser 444 is adapted to diffuse the light from the visible light illuminators. In some implementations, the light diffuser 444 is adapted to direct the light from the illuminators toward the lip 434 of the casing 401. In some implementations, the light ring 448 (and corresponding elements such as the light guide 446 and/or light diffuser 444) causes a circular colored (or white) light to be emitted from the front of the camera 118. In some implementations the components and corresponding light are circular and arranged around the periphery of the front of the camera 118. They may encircle all or substantially all elements of the camera 118, such as the image sensor assembly 432, the IR illuminators 452, the ambient light sensor 451, a status LED, and the microphone apertures 406. In other implementations, they are arranged not around the periphery but rather at an inner diameter, e.g., around only the image sensor assembly 432. In yet other implementations, they do not surround any front-facing element of the camera 118. In some implementations, they are arranged in a non-circular shape, such as a square, oval, or polygonal shape. In some implementations, they are not arranged on the front of the device but rather a different surface of the device, such as the bottom, top, sides, or back. In some implementations, multiple such light rings and components are arranged onto the same or different surfaces of the camera 118.

The light ring 448 (and corresponding elements) may operate to indicate a status of the camera 118, another device within or outside of the smart home environment 100 (e.g., another device communicatively coupled either directly or indirectly to the camera 118), and/or the entire connected smart home environment 100 (e.g., system status). The light ring 448 (and corresponding elements) may cause different colors and/or animations to be displayed to a user that indicate such different statuses.

For example, in the context of communicating camera 118 status, when the camera 118 is booting for the first time or after a factor reset, the ring may pulse blue once at a slow speed. When the camera 118 is ready to begin setup, the ring may breathe blue continually. When the camera 118 is connected to a remote cloud service and provisioning is complete (i.e., the camera is connected to a user's network and account), the ring may pulse green once. When there is a service connection and/or provisioning failure, the ring may blink yellow at a fast speed. When the camera 118 is being operated to facilitate two-way talk (i.e., audio is captured from the audio and communicated to a remote device for output by that remote device simultaneously with audio being captured from the remote device and communicated to the camera 118 for output by the camera 118), the ring may breathe blue continuously at a fast speed. When the camera 118 is counting down final seconds before a factory reset, the ring may close on itself at a rate equal to the time until reset (e.g., five seconds). When the camera 118 has been factory and while the setting are being erased the ring may rotate blue continuously. When there is insufficient power for the camera 118 the ring may blink red continuously at a slow speed. The visual indications are optionally communicated simultaneously, concurrently, or separately from audio indications that signal to the user a same or supplemental message. For example, when the camera 118 is connected to a remote cloud service and provisioning is complete (i.e., the camera is connected to a user's network and account), the ring may pulse green once and output an audio message that "remote cloud service and provisioning is complete."

Additionally or alternatively, the camera 118 may communicate the status of another device in communication with the camera 118. For example, when a hazard detector 104 detects smoke or fire sufficient to alarm, the camera 118 may output a light ring that pulses red continuously at a fast speed. When a hazard detector 104 detects smoke or fire sufficient to warn a user but not alarm, the camera 118 may output a light ring that pulses yellow a number of times. When a visitor engages a smart doorbell 106 the camera 118 may output a light ring depending on the engagement; e.g., if the smart doorbell 106 detects motion, the camera 118 may output a yellow light ring, if a user presses a call button on the smart doorbell 106, the camera 118 may output a green light ring. In some implementations, the camera 118 may be communicatively coupled to the doorbell 106 to enable audio communication therebetween, in which case an animation and/or color of the light ring may change depending on whether the user is speaking to the visitor or not through the camera 118 or another device.

Additionally or alternatively, the camera 118 may communicate the cumulative status of a number of network-connected devices in the smart home environment 100. For example, a smart alarm system 122 may include proximity sensors, window break sensors, door movement detectors, etc. A whole home state may be determined based on the status of such a plurality of sensors/detectors. For example, the whole home state may be secured (indicating the premises is secured and ready to alarm), alarming (indicating a determination that a break-in or emergency condition exists), or somewhere in between such as pre-alarming (indicating a determination that a break-in or emergency condition may exist soon or unless some condition is satisfied). For example, the camera 118 light ring may pulse red continuously when the whole home state is alarming, may pulse yellow when the whole home state is pre-alarming, and/or may be solid green when the whole home state is secured. In some implementations, such visual indications may be communicated simultaneously (or separately from) with audio indications that signal to the user the same or supplemental message. For example, when the whole home state is alarming, the ring may pulse red once and output an audio message that indicates the alarm "alarm". In some implementations, the audio message may provide supplemental information that cannot be conveyed via the light ring. For example, when the whole home state is alarming due to a basement window being broken, the audio message may be "alarm—your basement window has been broken." For another example, when a pre-alarm amount of smoke has been detected by a hazard detector 104 located in the kitchen, the audio message may be "warning—smoke is detected in your kitchen."

In some implementations, the camera 118 may also or alternatively have a status LED. Such a status LED may be used to less-instructively communicate camera 118, other device, or multiple device status information. For example, the status light may be solid green during initial setup, solid green when streaming video and/or audio data normally, breathing green when someone is watching remotely, solid green when someone is watching remotely and speaking through the camera 118, and off when the camera 118 is turned off or the status LED is disabled. It should be appreciated that the status LED may be displayed simultaneously with the light ring. For example, the status LED may be solid green during setup while the light ring breathes blue, until the end of setup when the device is connected to the service and provisioning is complete whereby the status LED may continue to be solid green while the light ring switches to a single pulse green.

Subject Monitoring Feedback Loop

The camera 118 described above in detail has many different uses in the smart-home environment. In the context of a security system, the camera 118 can detect human presence and/or motion, and can provide a real-time video feed of the monitored area to a user's smart phone or other mobile computing device. In a hazard-detection scenario, the camera 118 can provide a real-time video feed of a situation in which a hazard might exist. For example, if smoke is detected within the smart-home environment, the camera 118 can provide a view to show areas of the environment that may be affected by the fire or smoke. The camera 118 can be used to determine whether the alarm is a false alarm or an alarm situation to which a response may be required. A single camera 118 or set of cameras can be installed in a smart-home environment, and they can be put to many different simultaneous uses. For example, a single camera can be part of a home security system and part of a hazard detection system at the same time. One of the many uses to which the camera 118 can be simultaneously employed is that of monitoring any infant or other subject within the smart-home environment.

Many parents find comfort in being able to monitor their sleeping infant in real time. Video monitoring systems are available that provide a live video feed of an infant in their sleep environment. These live video feeds are traditionally sent through an RF frequency communication system to a dedicated video monitor or console that can be plugged in at different locations in the user's home. However, these traditional infant monitoring systems that employ live video feeds suffer from a number of drawbacks. First, these traditional systems typically employ a low resolution camera. The resultant video feed is typically grainy, and it is impossible to view details of the infant. Second, these cameras are typically unable to provide any additional information other than the live video feed itself. The live video feed provides very little information on the health and/or safety condition of the infant. Moreover, because there is no interactivity in these traditional video feeds, these baby monitors do not provide any meaningful emotional connection between the user and the infant.

In order to solve these and other technical problems, the embodiments described herein use the camera 118 with its high-resolution live video feed in conjunction with many other smart-home devices to not only monitor the sleep of a subject, such as an infant or child, but to also employ a feedback loop that optimizes the sleep conditions in the smart-home environment. The plurality of smart-home devices monitors a sleep environment to determine when the subject is in the sleep environment attempting to sleep. When the subject attempting to sleep is detected, the smart-home system can transition into a sleep mode. While in the sleep mode, the smart-home devices may be placed in a mode such that they do not interrupt the sleep of the subject. For example, doorbells can be silenced, intercom systems can be switched off in the sleep environment, and other systems can be silenced or otherwise made less likely to affect the sleep of the subject. While in the sleep mode, the smart-home devices can monitor the behavior of the subject to detect times when the sleep of the subject is interrupted. For example, the camera 118 described above can detect motions (e.g., tossing, turning, rolling over, etc.) that indicate restless sleep. The camera 118 can also detect temperatures of the subject that do not fit within a predefined thermal signature. The camera 118 in conjunction with other smart-home devices can listen for audible sounds, such as coughing, sneezing, and crying, that indicate interrupted sleep patterns.

After detecting the interrupted sleep patterns, the smart-home system can employ a number of different methods to optimize the sleep environment and help put the subject back to sleep. When initially entering the sleep mode, the smart-home system can download a set of default parameter values that govern the operation of the smart-home devices in and/or around the sleep environment. These parameters may include thermostat temperatures, thermal signatures of the subject, air filter operation, noise generation, lighting, music, and/or other environmental stimuli. When the subject's sleep patterns are interrupted, the behavior indicating the interrupted sleep can be matched to one or more of these environment or stimuli. For example, if the subject is coughing, the smart-home system can increase the operation of a humidifier and/or air filter. When the subject becomes too hot/cold, the smart-home system can decrease/increase the setpoint temperature of the thermostat in the sleep environment. In addition to linking interrupted sleep behavior to specific smart-home system control adjustments, additional sleep-aid methods can be employed, such as white-noise generation, low-level lighting, music, vibrations, and other smart-home actions that can help put the subject back to sleep. If the subject stays awake, the system can send an alert to a computing device of a parent or other monitoring individual and can transition out of the sleep state into a normal operating state.

The sleep behavior of the subject can be monitored over time and can affect the default parameter values of the smart-home devices while in the sleep state using a closed-loop feedback system. The default parameter values can initially be determined and downloaded from a server that monitors/interacts with the smart home devices. These default values can be based on a population of similar subjects, and can represent parameters that have produced an optimal sleep environment within the population of similar subjects. For the particular subject being monitored in the smart-home environment, these values may not be initially optimal. As interrupted sleep is detected and remedied by changing the parameters of the smart-home devices, these changes can be fed into a neural network comprised of machine learning algorithms that determine when the changed parameter should permanently affect the default parameters that are assigned to the smart-home devices in that particular smart-home environment when entering the sleep state. Furthermore, as the parameters for an individual subject/environment are changed, these changes may also be provided to the server. When a sufficient number of similar changes for a similar subject population are received, the default values provided by the server may also be changed for that population using neural network. Therefore, the close-loop feedback system can operate at an individual level and/or a population level for a plurality of smart-home environments.

Throughout this disclosure, the monitoring system may use the monitoring of an infant or child as an example. However, other embodiments are not limited to an infant in a sleep environment. Some embodiments may monitor other types of subjects, such as the elderly, the physically disabled, and/or other human subjects. These subjects may also be monitored in any environment aside from a sleep environment. For example, a subject could be monitored in a wheelchair, in a swimming pool, in a bed, in a recliner, on a couch, and/or any other environment. Although the camera 118 described above is also used as an example, other embodiments may use different home video cameras that are configured to capture a live and/or thermal video feed of the monitored subject. Any smart-home device may also be used as part of the smart-home system to monitor the sleep of the subject and/or provide environmental controls and/or stimuli to help improve/optimize the sleep environment. The hazard detector, home assistant, thermostat, air filter, camera, and/or lighting systems described herein are provided as examples, and are not meant to be limiting. Other smart-home systems may also be incorporated into the smart-home environment to monitor/aid the sleep of the subject.

Figure 6:
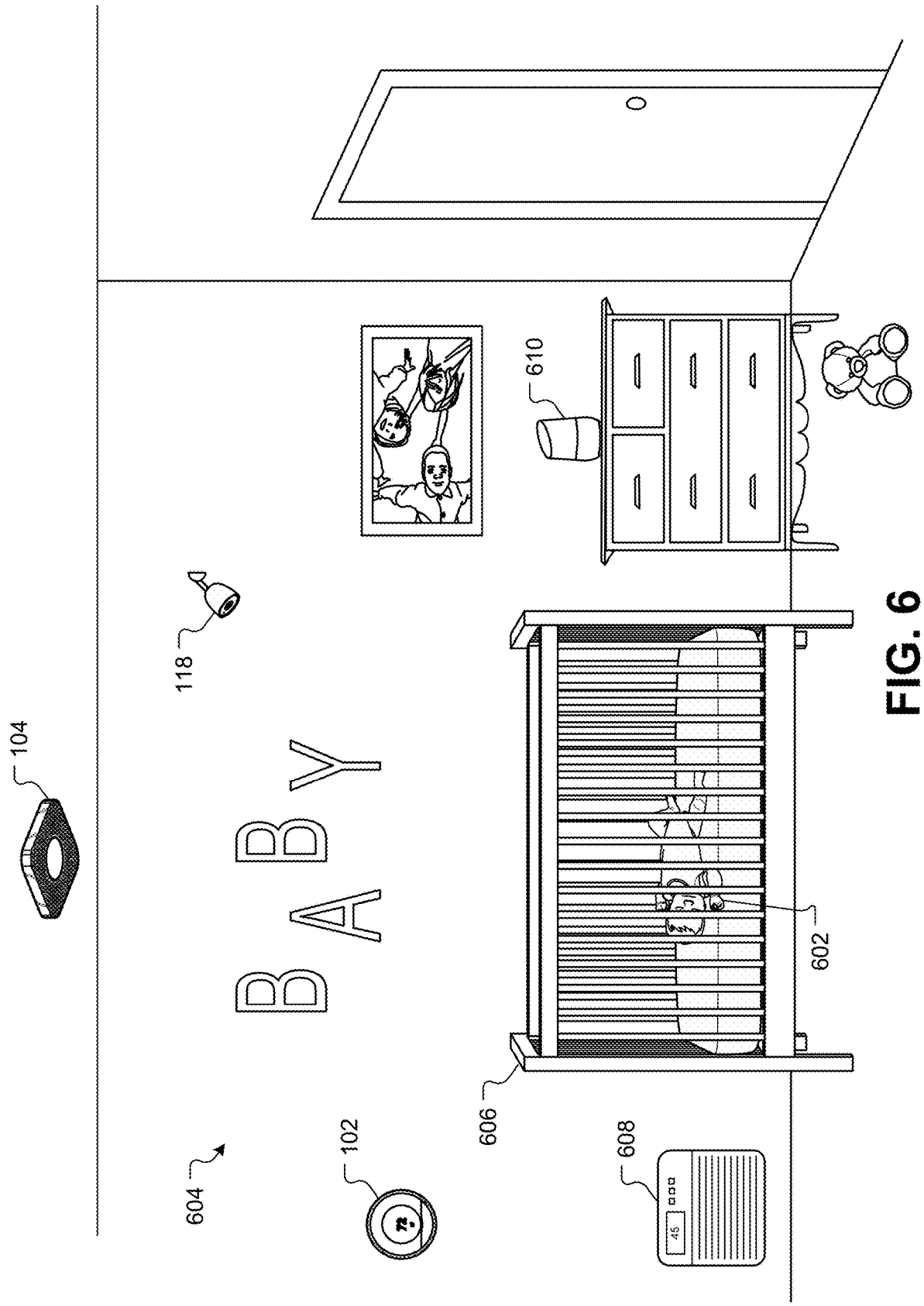
FIG. 6 illustrates an infant sleeping in a sleep environment and being monitored by a camera, according to some embodiments.

FIG. 6 illustrates an infant 602 sleeping in a sleep environment 604 and being monitored by a plurality of smart-home devices, according to some embodiments. The plurality of smart-home devices may include a camera 118. The camera 118 may be one of many video cameras that are distributed throughout the smart-home environment. Although not depicted explicitly in FIG. 6, the sleep environment 604 may also include additional cameras, some of which may also be positioned to observe the infant 602. Other cameras may be used for security purposes or may be configured to observe the infant 602 in other positions and/or other locations within the sleep environment 604. In some embodiments, the camera 118 may include both a regular, visible-light camera function along with a thermal imager. The thermal imager may include a non-contact temperature measurement device that records thermal energy at pixel locations. The thermal imager can detect infrared energy that is emitted and/or reflected by any object or subject within its field-of-view. The thermal imager can convert the thermal emissions into a thermogram, or thermal image, that can be displayed and/or analyzed by a computing device. The thermal imager need not be as high resolution as the camera 118. For example, some embodiments may use a thermal imager having a 100×100 pixel resolution. This low resolution may be sufficient for detecting thermal conditions sufficiently to diagnose various problems that may be associated with the subject being monitored. Using a low resolution thermal imager can also reduce the amount of memory, processing power, and/or bandwidth required for the analysis describe below. High-resolution thermal imagers can be used to detect smaller problems at greater distances, and the final resolution of the thermal imager on the camera 118 may be selected based on a distance of the camera 118 from the infant 602.

In this example, the camera 118 is positioned within the sleep environment 604 such that a live video feed of the infant 602 can be captured. Some embodiments may include automatic pan/tilt mounts that use computer vision algorithms to automatically train the camera 118 on the infant 602 such that the infant 602 can be located anywhere in the sleep environment 604 and still be monitored by the camera 118. In some embodiments, the pan/tilt mounts can be driven by motion detection algorithms in the camera, such that they focus on motion detected in their field-of-view. Some embodiments may use one or more cameras that are trained specifically on different locations within the sleep environment 604, such as the crib 606, the floor, a changing table, and/or the like. Each of these cameras may be activated when movement is detected within their field of view. Therefore, when the infant 602 is placed in the crib 606, the camera 118 can automatically detect the shape and/or movement of the infant 602 and determine that the infant 602 is within its field of view. Camera 118 can then automatically begin recording, analyzing, and/or transmitting a live video feed of the infant 602. Some embodiments may require a facial image of the infant 602 to detect fevers and other heat-related conditions. These embodiments may use known facial recognition algorithms to locate the face of the infant 602 within its field-of-view and pan/tilt/zoom the camera 118 accordingly to center its field-of-view on the face of the infant 602.

The sleep environment 604 may also include additional smart-home devices. Some embodiments may include a hazard detector 104. The hazard detector 104 may include a low-level light ring that can provide a small amount of light to the sleep environment 604. The hazard detector 104 may also include a speaker that can provide sound, such as white noise, music tracks, ocean sounds, and so forth. The hazard detector 104 may be connected via a smart-home network to the other smart-home devices. Some embodiments may also include a thermostat 102. The thermostat 102 may include an active electronic display that can provide a small amount of light to the sleep environment 604. The thermostat 102 can also manage the temperature of the sleep environment 604 by measuring the ambient temperature in the sleep environment 604 and comparing the measured ambient temperature to a target setpoint temperature. Some embodiments may also include a home assistant 610. The home assistant may be a voice-activated, network-connected speaker. The home assistant 610 can provide low-level lighting and can play a variety of sounds in the sleep environment 604. For example, the home assistant 610 can play music, white noise, prerecorded messages or songs from a parent, and/or the like. The home assistant 610 may also include a microphone that can record and/or transmit any sound that is generated in the sleep environment 604. In some embodiments, the home assistant 610 may be capable of processing sounds made by the infant 602 and generating audio outputs based on those sounds and/or sending an alert to a monitoring device outside the sleep environment 604. Some embodiments may additionally include an air purifier

608. The air purifier 608 can provide a low-level noise in the sleep environment 604 and can filter and/or circulate air around the sleep environment 604. The smart-home devices described above are only provided by way of example and are not meant to be limiting. Additional smart-home devices may be present in the sleep environment 604, such as motion detectors, smart outlets, controlled lighting, intercoms, video monitors, and so forth.

The sleep environment 604 may include a bedroom, a closet, a nook, and/or any other location within the smart-home environment. The sleep environment may be characterized in that it includes a bed, a crib 606, a couch, a sofa, a porta-crib, a mattress, a sleeping pad, an air mattress, a covered section of the floor, and/or any other sleep-suitable location. Although the infant 602 is depicted in FIG. 6, any other monitored subject may also be monitored by the camera 118 and used in conjunction with the algorithms described in detail below. Other subjects may be monitored in sleep environments and/or any other type of monitored environment within the smart-home environment.

Figure 7:
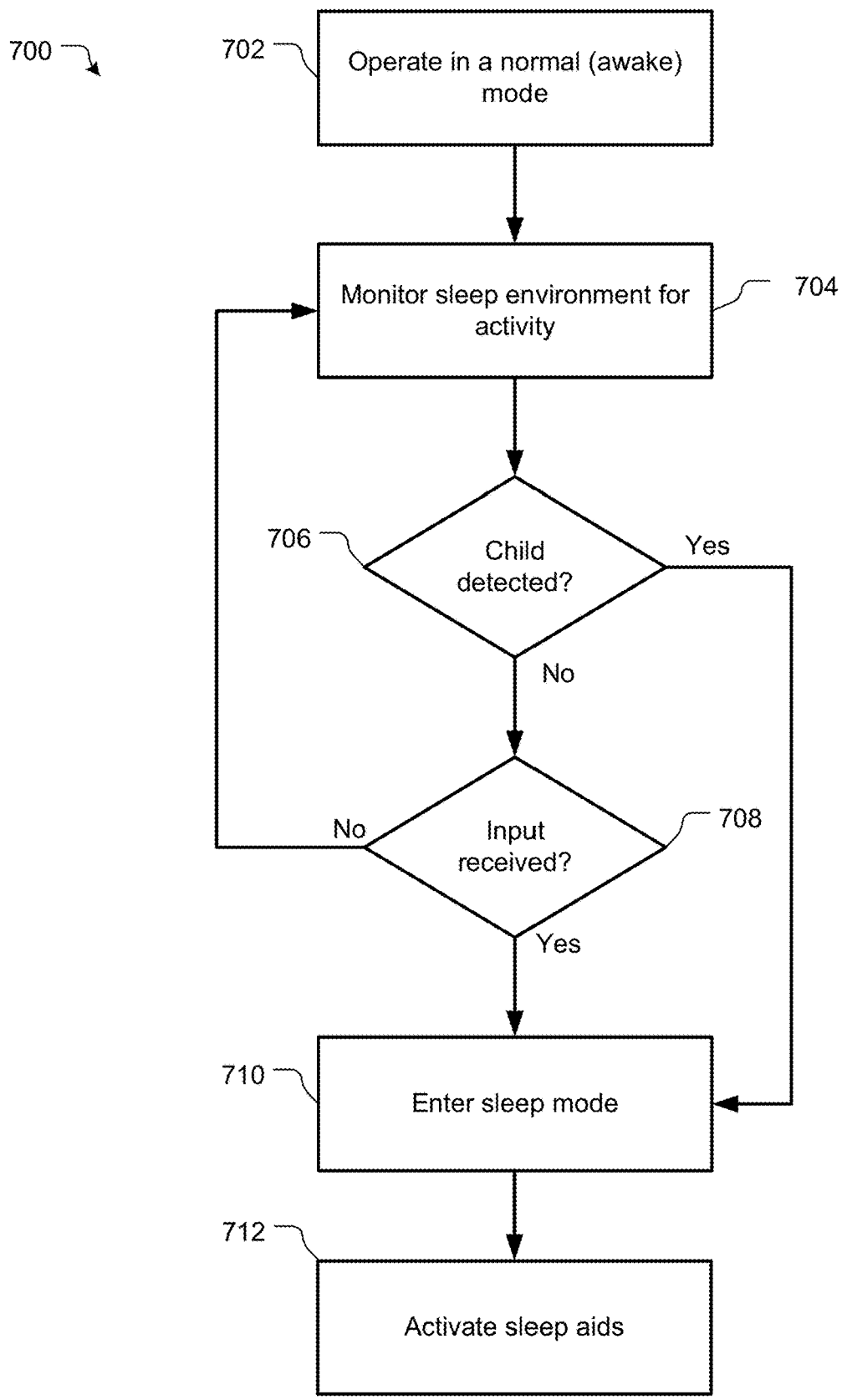
FIG. 7 illustrates a flowchart of a method for determining when the smart-home devices in the home should enter into a sleep mode, according to some embodiments.

The smart-home devices depicted in FIG. 6 can work together in conjunction with other smart-home devices in the home to monitor and control the sleep environment of the monitored subject, such as the infant 602. FIG. 7 illustrates a flowchart 700 of a method for determining when the smart-home devices in the home should enter into a sleep mode, according to some embodiments. The method may include operating in a normal/awake mode (702). The normal mode of operation may allow the smart home devices within the home to operate according to their normal schedules and/or inputs. For example, a stored setpoint schedule may be used by the thermostat 102 to regulate a temperature throughout the home and in the sleep environment 604. An alarm system may be free to trigger an audible alert when it detects an unauthorized presence. An intercom system may allow users to communicate with any room in the home. The hazard detector 104 may be free to sound an alarm when smoke is detected, and so forth. The normal mode of operation may describe operations where no changes are made to the operation of any smart-home devices based on optimizing the conditions of the sleep environment 604.

The method may also include monitoring the sleep environment for activity (704). In some embodiments, the sleep environment can be monitored for activity that indicates the presence of the subject in the location performing actions that indicate that the subject should be asleep. For example, the camera 118 can use computer vision algorithms to recognize that a human subject has entered the sleep environment 604 and is in the crib 606. Motion detectors in the sleep environment 604 that are part of a security system can detect a motion pattern that indicates someone placing the infant 602 in the crib 606. Each of these systems can individually and/or collectively detect the presence of the infant 602 in the correct sleep location, such as the crib 606.

As the sleep environment 604 is monitored by the smart-home devices, a determination can be made as to whether or not a child is detected (706). Some embodiments may detect more than simply the presence of the infant 602. For example, these embodiments may determine the presence of an infant 602 that is asleep based on motion detection algorithms executed by the camera 118. These embodiments may also determine the presence of an infant 602 with a facial signature that is consistent with a predetermined facial signature of the infant 602 when it is asleep. Some embodiments may recognize the presence of the infant using the camera 118 and/or other motion/presence sensors to determine that the infant 602 is present in the crib 606 and not making any noise using the microphone of the home assistant 610 and/or any of the other smart-home devices. Therefore, one or more of the smart-home devices, acting individually or collectively, can process inputs in the sleep environment 604 to determine that the infant 602 is present in the sleep environment 604 for the purpose of sleeping. When such a determination is made, the smart-home system can enter into a sleep mode (710) as described in detail below.

Some embodiments may additionally or alternatively make a second determination based on user inputs (708). In some embodiments, users can provide an input to one or more smart-the home devices indicating that the system should enter the sleep mode. For example, a user can tell the home assistant 610 that the infant 602 is asleep and ask the home assistant 610 to place the smart-home system into the sleep mode for a specified time interval. In some embodiments, users may provide a sleep schedule to the smart-home system indicating that the infant 602 will sleep between 2:00 PM and 4:00 PM each day. This input can cause the system to automatically enter the sleep mode during the specified time interval. In some embodiments, users may provide a sleep schedule that indicates a start time for a scheduled nap/bedtime, and allow the smart-home system to monitor the sleep pattern of the infant 602 and automatically transition out of the sleep mode when the sleep of the infant 602 is interrupted for a predetermined time interval. Some embodiments may automatically learn a sleep schedule of the infant 602 over time using inputs received by the camera 118 and other smart-home devices in the sleep environment 604. The smart-home system can then automatically generate a sleep schedule that is learned based on the behavior of the infant 602 and/or the parents of the infant 602. The smart-home system can then implement a sleep schedule based on the observed behavior of these human occupants. Some embodiments may use a combination of user inputs, learned or provided sleep schedules, and/or immediate smart-home device sensor inputs. For example, the smart-home devices may use thresholds to determine when the infant 602 is present and sleeping. These thresholds may be lowered during time intervals that coincide with a predetermined and/or learned sleep schedule. User inputs indicating that the system should enter the sleep mode may override any automatic determinations made by the smart-home system based on sensor inputs and/or stored schedules.

When the situations described above determine that the system should enter the sleep mode (710), certain smart-home device parameters can be altered throughout the home. The sleep mode may be intended to prevent the smart-home system from interrupting the sleep of the infant 602 without sufficient cause, such as an emergency situation. Therefore, operating parameters of smart-home devices inside and/or outside the sleep environment 604 can be changed temporarily during the sleep mode. For example, the hazard detector 104 may be prevented from broadcasting audible warnings in the sleep environment 604 for a short time interval when smoke is detected in other parts of the home away from the sleep environment, such as the kitchen. An intercom system may be prevented from generating sound in the sleep environment 604 without a specific command indicating a user intends to broadcast into the sleep environment 604. Any noise-generating smart-home devices can have their sound outputs lowered and/or disabled when in the sleep mode. For example, a doorbell system can be lowered in volume, disabled, and/or only allowed to generate noise on a level/floor of the home that is different from the sleep environment 604. It will be understood that any parameter change in the sleep mode need not disable or lessen the effectiveness of any emergency systems. Hazard detectors throughout the home can still detect smoke and warn occupants of danger. Security systems may still detect intruders and unauthorized entry. Generally, users may provide preferences that define alert methods that can still be effective while in the sleep mode without generating loud noises in the sleep environment 604.

In addition to applying the default sleep mode parameters for the smart-home devices when entering the sleep mode (710), some embodiments may also activate one or more sleep aids (712). Activating the sleep aids will be described in detail below in relation to FIG. 12. Generally, activating sleep aids may include turning on low-level lighting, playing white noise, lullabies, voice recordings, and/or other comforting sounds that may help induce sleep, activating moving devices such as crib-mounted mobiles or crib-vibration devices, and so forth. The sleep aids can be activated automatically when entering the sleep mode to help the infant 602 quickly go to sleep. The system can monitor the behavior of the infant 602 using the camera 118 and other smart-home devices to determine when the infant 602 is asleep. Once the infant 602 is asleep, the sleep aids can be deactivated. The sleep aids can be deactivated one-at-a-time and/or may be gradually turned down or turned off such that deactivating the sleep aids is not abrupt. In some embodiments, the sleep aids can be turned on when entering the sleep mode for a predetermined time interval, such as 15 minutes, then turn off automatically at the end of the predetermined time interval.

Figure 8:
FIG. 8 illustrates a view of the infant that may be received by the camera, according to some embodiments.

FIG. 8 illustrates a view of the infant 602 that may be received by the camera 118, according to some embodiments. In many situations, the infant 602 may be relatively immobile while sleeping. For example, the infant 602 may be confined to the crib 606 while sleeping. Therefore, the field of view of the camera 118 may be adjusted or shrunk to capture in high resolution only the area in which the infant 602 may occupy in the sleep environment. This may include automatically panning/tilting the camera to center its field of view on the infant 602. Additionally and/or alternatively, a zoom of the camera 118 can be adjusted such that the infant 602 substantially fills the field-of-view of the camera 118. For example, the zoom of the camera may be adjusted until the infant 602 fills approximately 50% of the field of view of the camera 118. In some embodiments, the automatic pan/tilt of the camera 118 can be influenced by a facial recognition algorithm that recognizes the face of the infant 702 in its field-of-view and causes the camera to center its field-of-view on the face of the infant 602. The camera 118 described in detail above includes, for example, a 4 k resolution. In some embodiments, the live video feed of the camera 118 may be one of the primary ways of monitoring the sleep of the infant 602.

Figure 9:
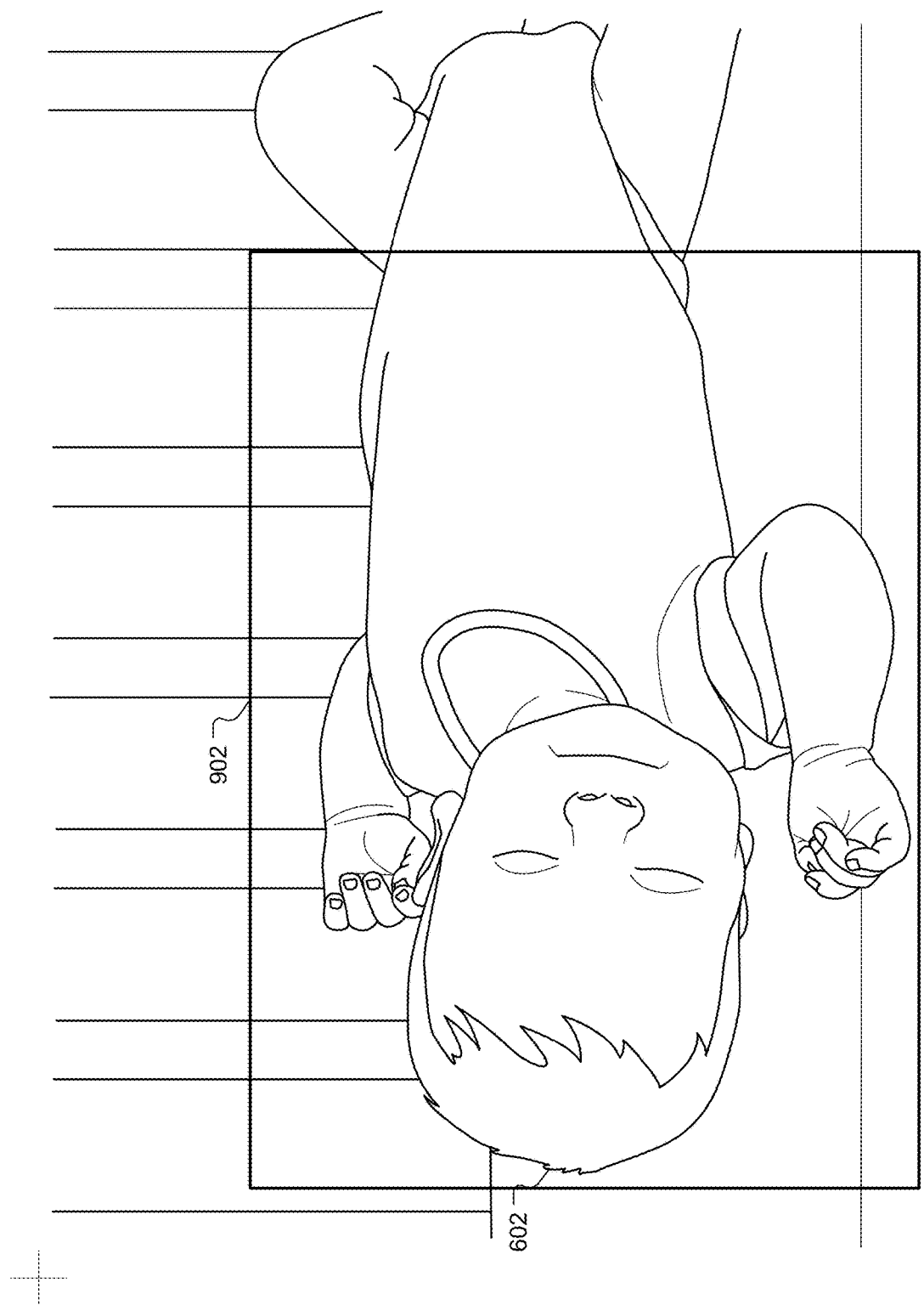
FIG. 9 illustrates a camera view and of the infant with a bounding box that reduces the processing power, memory, and/or bandwidth required by the system, according to some embodiments.

FIG. 9 illustrates a camera view and of the infant 602 with a bounding box 902 that reduces the processing power, memory, and/or bandwidth required by the system, according to some embodiments. Some embodiments may analyze the real-time video feed of the infant 602 at the camera 118. In these embodiments, it may be advantageous to decrease the number of pixels that need to be analyzed in the full field-of-view of the camera 118. By reducing the analyzed portion of the field-of-view of the camera 118, algorithms can run faster and less memory can be used on the camera 118. This may be particularly advantageous for cameras that have relatively small processing capabilities and/or relatively limited memory storage available.

In some embodiments, the video feed of the camera can be analyzed in real time to identify a portion of each image frame that includes the face of the infant 602. A bounding box 902 can be selected that includes the face, along with a predetermined amount of each surrounding image. For example, a bounding boxing 902 can include the face at the center of the bounding box 902, and can also expand to include an additional two feet of image extending outward from the face. In other embodiments, the bounding box 902 can include the face, as well as a surrounding area that can be visually identified as a subject (e.g. the infant 602). In the example of FIG. 9, the bounding box 902 includes the face as well as the rest of the upper body of the infant 602. Computer vision algorithms can be used to identify objects, and these computer vision algorithms can be modified based on this particular environment to identify the shape of the infant 602 in each frame. The bounding boxing 902 can be sized such that the entire infant 602 is captured within the analyzed area for the camera 118.

In some embodiments, the resolution of the captured video feed can be altered based on the bounding box 902. For example, the camera can record and transmit a lower resolution video image for portions of the image outside of the bounding box 902, while preserving a high-resolution digital image for portions of the video feed that are inside the bounding box 902. This can simplify the video processing of a thermal-signature-matching algorithm, decrease the bandwidth required to transmit the live video feed in real time, reduce the amount of processing power required to detect the small motions 702 in the live video feed, and/or reduce the amount of memory required to store images and information associated with the live/thermal video feeds.

As described above, the live video feed of the camera 118 can be one of the primary inputs used to determine that the infant 602 is present in the sleep environment 604 and in a sleep situation such that the sleep mode of the smart-home system should be entered. As described above, the camera 118 can capture a view of the infant 602 and use computer vision algorithms, motion detection algorithms, thermal signatures, noise detection, object/facial recognition algorithms, and so forth to determine the presence of the infant 602 in a sleep situation. In some embodiments, the camera 118 can distinguish between situations where a human other than the infant 602 is present in the sleep environment 604. For example, when a parent is cleaning the sleep environment 604, the smart-home system may distinguish between the parent and the infant 602 based on the size of the parent, the thermal signature of the parent, the facial recognition of the parent, the motion patterns of the parent, and so forth. Additionally, the camera 118 can distinguish between situations where the infant 602 is present in the sleep environment 604 for the purpose of sleeping and situations where the infant 602 is merely present in the sleep environment 604. For example, if the infant 602 is crawling on the floor of the sleep environment 604 and not in the crib 606, it is unlikely that the infant 602 is in the sleep environment 604 for the purpose of sleeping. In another example, if the infant 602 is standing in the crib 606, then it is possible that the infant 602 is in the crib 606 to play, for a timeout, to be kept off the floor of the sleep environment 604 while the parent cleans, and so forth. Generally, a parent can set preferences in the smart-home system that define the situations in which the infant 602 is present in the sleep environment 604 for the purpose of sleeping. In some embodiments, these preferences can be set automatically as the smart-home system learns the behavior of the infant 602. For example, if the camera 118 observes the infant 602 lying in the crib 606 every day from 2:00 PM to 4:00 PM, the smart-home system can use these characteristics (i.e., infant in the crib, infant lying down, etc.) to define behaviors and/or times when the system should enter the sleep mode.

Figure 10:
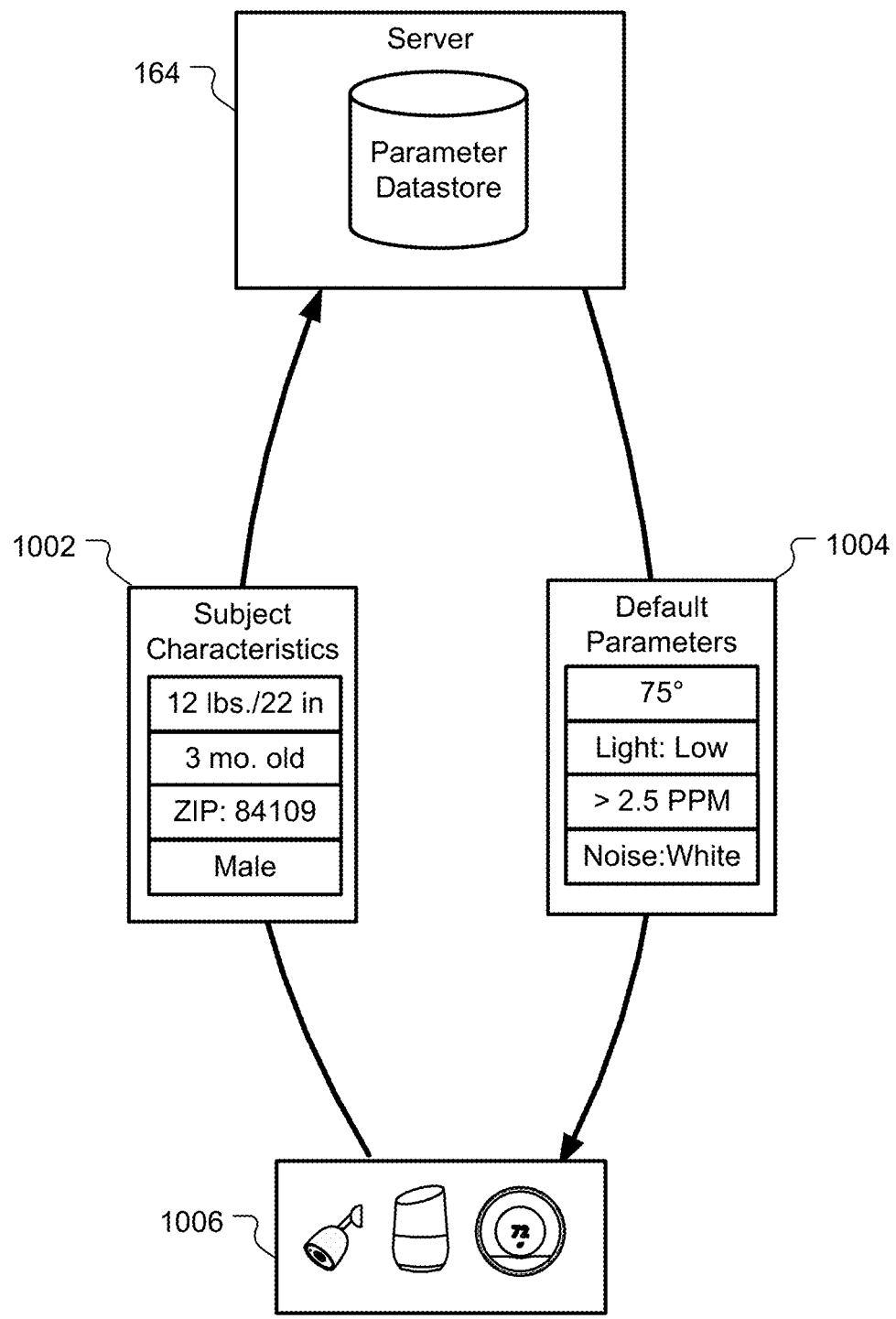
FIG. 10 illustrates a system for providing default parameters for smart-home devices, according to some embodiments.

FIG. 10 illustrates a system for providing default parameters for smart-home devices, according to some embodiments. The plurality of smart-home devices 1006 each may operate using one or more stored parameters. The thermostat 102 may use stored setpoints and/or setpoint schedules as parameters that control the operation of the HVAC system. The air purifier 608 may include an operating schedule and/or specified level of air purity that governs its operation. Various lighting systems in the sleep environment, including light provided by the hazard detector 104 and/or the home assistant 610, may include light levels and/or schedules defining how light should be provided. Any smart-home devices having speakers or noise generation capabilities may include parameters that define times, volume, and sound content for any sound output. Each of these parameters may be provided by user inputs, default parameters, and/or learning algorithms in the smart-home environment.

When transitioning to the sleep mode, new parameters may be provided to any of the smart-home devices in the home as described above. These new parameters may be configured to optimize the conditions of the sleep environment 604 to be conducive to the sleep of the infant 602 while preventing any external sleep interruptions that can be avoided. In some embodiments, these default parameters may be preprogrammed into each of the smart-home devices in the home in a manufacturing or post-manufacturing process. In some embodiments, these default parameters may be provided through inputs received from users during a setup process through, for example, a progression of interview-style user interfaces. In some embodiments, these default parameters may be learned through user inputs during operation of the various smart-home devices. For example, if users consistently increase the temperature in the sleep environment and cause the home assistant 610 to provide white noise between 2:00 PM and 4:00 PM, the smart-home system can use these user changes as parameters for the sleep mode rather than incorporating them as changes to the normal setpoint schedules for the smart-home devices during the normal operating mode.

In some embodiments, a server 164 that monitors one or more of the smart-home devices may provide the default parameters for the sleep mode. The server 164 may be configured to monitor smart-home devices in many different homes across a wide variety of geographic locations. The server 164 can generate profiles for different types of subjects in various sleep environments. For example, the server 164 can cluster different sleep environments based on characteristics of the subjects and/or the sleep environments themselves and generate default parameters 1004 for the population of subjects in each cluster. In some embodiments, populations of subjects can be clustered together based on subject characteristics, such as length, weight, age, gender, birth method, nursing status, teething status, and/or any other physical condition that contributes to a sleep pattern of the subject. Populations of subjects may also be clustered together based on characteristics of the sleep environment, such as room size, sleep-area (e.g., crib) size, home square footage, sound/temperature insulation, architectural layout, smart-home devices present, number of occupants in the home, external noise sources, geographic location, ZIP Code, altitude, weather, and so forth.

Before entering the sleep mode, the smart-home system can send a request to the server 164 requesting the default parameters 1004 that are specifically tailored for a population that is similar to the infant 602 and/or similar to the sleep environment 604. In order for the server 164 to select the corresponding default parameters 1004, users can elect to provide any subject characteristics 1002 to the server 164. When permission is granted to send the subject characteristics 1002 to the server 164, the server 164 can identify a population cluster into which the infant 602 and/or sleep environment 604 would be placed.

The default parameters 1004 for that cluster can then be sent back to the smart home devices 1006 for use during the sleep mode.

As will be described in greater detail below, the default parameters 1004 can act as an initial setting in the local smart-home environment. A closed feedback loop can be used locally to optimize those default parameters 1004 such that they are tailored for the specific situation of the infant 602 rather than just a population that is similar to the infant 602. By using the default parameters 1004 as a starting point, users are relieved of the need to determine their own initial settings for the sleep mode, which can be a very technical process. Users may also not be sure how to optimize each of the smart home devices in the sleep environment 604. Additionally, providing default parameters 1004 that are close to the optimal parameters for the particular sleep environment 604 may allow the system to optimize those parameters faster and converge towards the optimal sleep environment far more rapidly than it could if starting with parameters that were not derived from a substantially similar population and/or environment.

Figure 11:
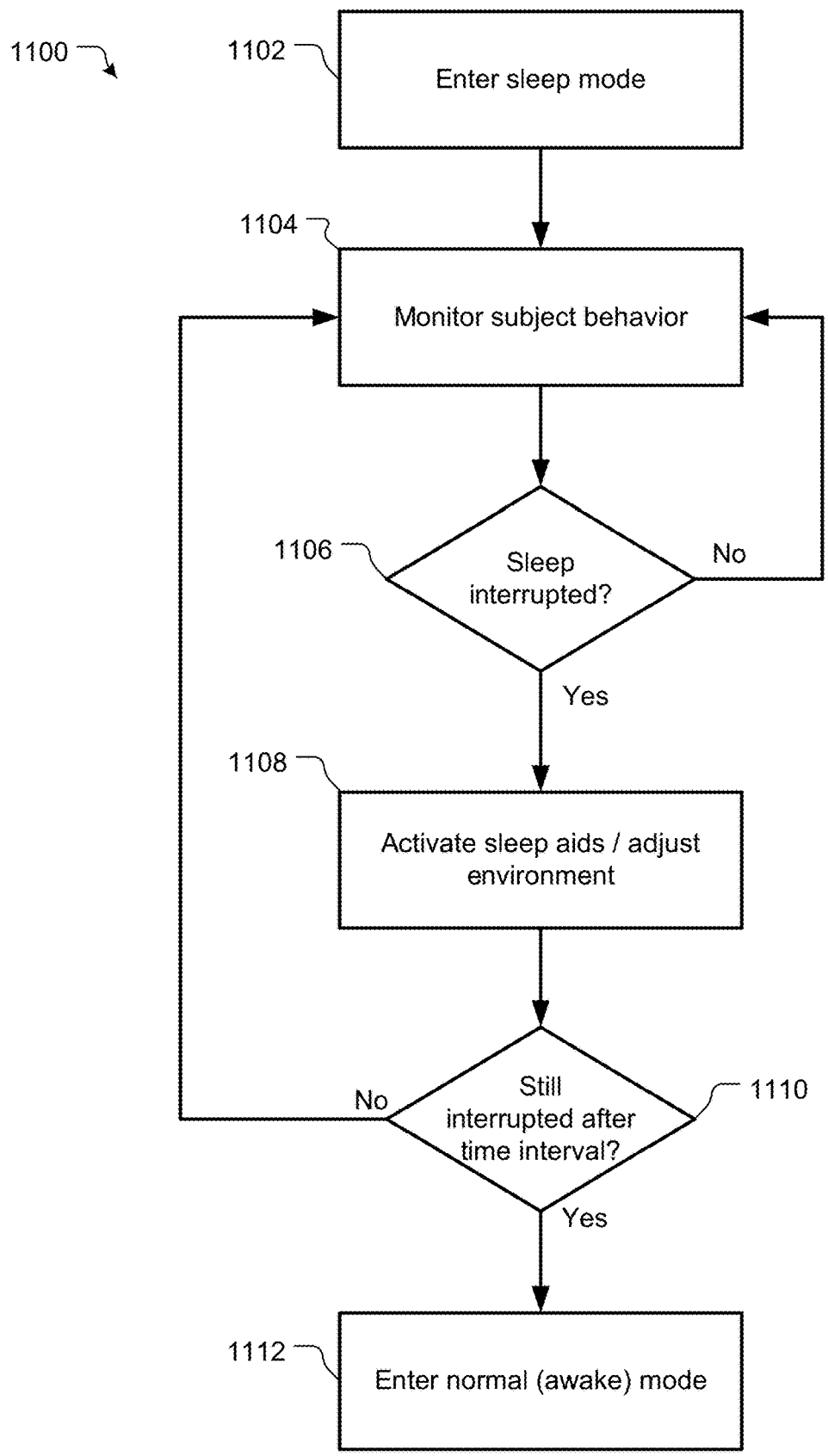
FIG. 11 illustrates a flowchart of a method for monitoring the sleep of the subject and adjusting environmental conditions to optimize the sleep environment, according to some embodiments.

FIG. 11 illustrates a flowchart 1100 of a method for monitoring the sleep of the subject and adjusting environmental conditions to optimize the sleep environment, according to some embodiments. The method may include entering the sleep mode (1102). The sleep mode may be entered using any of the methods described above. The method may also include monitoring the behavior of the subject (1104). Any of the smart-home devices in the sleep environment 604 can be used individually and/or in combination to monitor the behavior of the subject. In some embodiments, the subject may be specifically monitored to determine whether the subject is sleeping soundly or whether the sleep of the subject is being interrupted (1106).

In some embodiments, the motion of the subject can be monitored by the camera 118. A motion detection algorithm can be used to determine if the subject is moving more than a threshold amount while the subject is supposed to be asleep. The threshold can be set such that small and/or isolated motions that do not generally indicate interrupted or restless sleep can be ignored. Computer vision algorithms can identify individual body parts of the infant 602, and compare the motion of the infant to known motion patterns that indicate interrupted sleep. For example, an infant moving their arms up-and-down or kicking their legs repeatedly may indicate interrupted sleep. These motion patterns can be detected by the camera 118 to determine that the sleep of the infant is interrupted. In another example, an infant attempting to roll over or rolling over repeatedly may indicate interrupted sleep. Again, this motion pattern may be detected by the camera 118 to determine that the sleep of the infant is interrupted. In another example, relatively small, isolated movements of the arms/legs of the infant may simply indicate normal motions that are experienced by the infant 602 during sleep, and therefore need not indicate restless sleep. Because the duration of these motions and/or the magnitude of these motions would fall below the predetermined threshold, the system can determine that these motions do not necessarily indicate interrupted sleep unless they continue in time and/or increase in magnitude.

In addition to detecting motion, motion patterns, and/or motion signatures, the camera 118 can also be used to detect other behaviors or characteristics of the infant 602 in order to determine when sleep is being interrupted. For example, the camera 118 may include a thermal imaging camera that can provide a thermal image of the infant 602. As will be described in greater detail below. The thermal image of the infant 602 can be analyzed to detect characteristics of the infant, such as being too cold, being too hot, experiencing medical problems including fever, teething, and/or infection, and so forth. The camera 118 can also capture and analyze the skin color of the infant 602. A skin color that is too pale or blue can indicate poor circulation and/or a sleep environment 604 that is too cold. Skin that is red and/or flushed may indicate a sleep environment 604 that is too hot, as well as a medical conditions such as a fever. A baseline skin color for the infant 602 during normal sleep can be established during a training interval, and that baseline skin color can be compared to a current skin color by the camera 118 during future sleep intervals. Deviation from the baseline skin color can be used to determine that the sleep of the infant 602 is not optimal, and can cause the smart-home system to generate a response as described below.

The camera 118 can also detect additional situations where the sleep of the infant may be interrupted. In some embodiments, a facial expression of the infant 602 can be compared to a baseline facial expression that is learned by the smart-home system while the infant 602 is sleeping. The facial expression can be captured using the visible light imager of the camera 118 and/or the thermal imager of the camera 118. Facial recognition algorithms can be used to not only identify the infant 602, but can also be used to compare a baseline facial expression to a current facial expression captured by the camera 118. If changes in facial expression continue for more than a threshold amount of time or deviate from the baseline facial expression by more than a threshold amount, the smart-home system can determine that the sleep of the infant 602 is being interrupted.

In some embodiments, sensors on smart-home devices in the sleep environment 604 can monitor the ambient conditions in the sleep environment 604 and determine if a significant deviation from the default parameters occurs. For example, the thermostat can monitor the temperature in the sleep environment 604 and determine whether the ambient temperature in the room is staying near enough to a target temperature specified in the default parameters. If the room is not maintaining its temperature as it should, this can indicate poor insulation or even an open window. If the air purifier 608 is filtering an abnormal amount of particles from the air of the sleep environment 604, this can indicate that something is causing the air quality to be diminished. If the hazard detector 104 detects smoke, this can indicate a dangerous situation in the sleep environment 604. Each of these types of indications may typically coincide with the sleep of the infant 602 being interrupted. Therefore, these environmental abnormalities can also be used as indications that the sleep of the infant 602 is being interrupted or may soon be interrupted. Additionally, in cases where environmental abnormalities in the environment are detected, thresholds for the actual behavior of the infant 602 can be lowered. For example, if the temperature for the sleep environment 604 is below the setpoint temperature, then the thermal threshold for the thermal image of the face of the infant 602 can be lowered to determine that sleep is being interrupted sooner. In another example, if the air quality in the sleep environment 604 is below a threshold quality, then a sound threshold for duration of magnitude for detected coughing/sneezing can be lowered to determine that the sleep of the infant 602 is being interrupted sooner.

In some embodiments, the behavior of the subject can be monitored through sound using microphones on various smart-home devices. As with motion detection, small, isolated sounds that fall below a threshold in magnitude and/or duration can be ignored by some embodiments. Other embodiments may determine that any sound made by the infant is indicative of interrupted sleep. Different types of interrupted sleep can be determined based on an audio signature of any sound recorded from the infant. These audio signatures can be downloaded from a database from the server 164 in a manner similar to how the default parameters 1004 were downloaded such that these audio signatures can be fit to a population of subjects that are similar to the infant. These audio signatures may include signatures for crying, sneezing, coughing, gagging, sucking on a pacifier, wheezing, snoring, and/or any other noise that may indicate restless sleep in a subject. For subjects that are becoming verbal, the smart-home system can learn over time different audio sounds made by the particular subject and determine whether they indicate interrupted sleep or normal sounds made during normal sleep cycle. For example, some children may talk in their sleep or routinely make other noises that do not indicate that their sleep is restless or being interrupted. Similarly, some children may make specific sounds or say words/phrases when they are waking up. Over time, the smart-home system can record these different sound types and classify them as sounds that indicate interrupted sleep, normal sleep, or an awake state for the subject.

When the sleep of the infant 602 is determined to be interrupted, the smart-home system can activate one or more sleep aids and/or adjust the physical conditions of the sleep environment 604. The algorithm for determining which sleep aids to activate and/or which environmental conditions to adjust is described in detail below in relation to FIG. 12. Generally, behaviors of the infant 602 can be linked to specific environmental conditions. The smart-home devices can then adjust the default parameters governing these environmental conditions to specifically address the behaviors of the infant 602. A plurality of sleep aids (e.g., night-lighting, white noise, vibrations, etc.) that are not necessarily linked to aberrant environmental conditions can also be employed to help automatically soothe the infant 602 and put them back to sleep.

The system can continue employing sleep aids and/or adjusting environmental conditions to help soothe the infant 602 when their sleep is interrupted. However, at some point it may be determined that the infant 602 is fully awake and not going back to sleep. A determination can be made as to whether the interrupted sleep has continued long enough to assume that the infant 602 will not go back to sleep on their own (1110). For example, if the crying of the infant 602 exceeds a predetermined time interval or exceeds an intensity/volume threshold, a determination can be made that the infant 602 may not go back to sleep on their own. In another example, if the infant 602 rolls onto their stomach, the smart-home system can transition out of the sleep mode and alert a monitoring device accessible by a parent or guardian. In some embodiments, the smart-home system can continuously learn different behaviors of the subject to determine when the system should transition back to the normal operating mode (1112). For example, if the infant 602 gets too cold as detected by the camera 118, the thermostat 102 can adjust the temperature in the sleep environment 604 accordingly. However, once too cold, the infant 602 may not go back to sleep on their own. After this situation occurs multiple times, the smart home system can learn that when the temperature of the infant 602 gets too cold and the infant 602 cries for more than two minutes, the system should transition back to the normal operating mode and alert a parent. Thus, a closed-loop feedback system can continuously update a set of conditions and/or behaviors that indicate that the child is awake enough that the system should no longer operate in the sleep mode.

Figure 12:
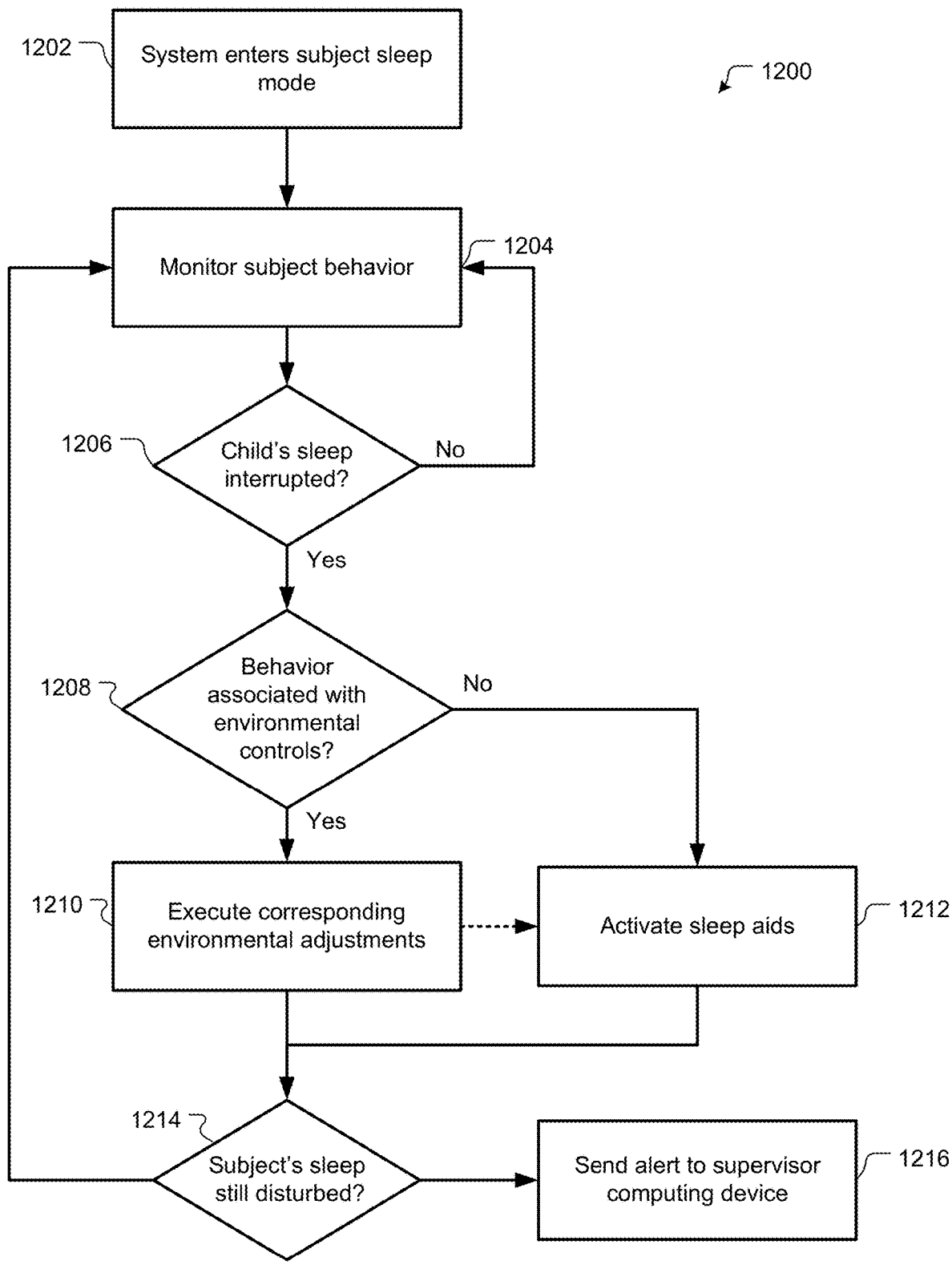
FIG. 12 illustrates a flowchart of a method for automatically soothing a subject whose sleep has been interrupted, according to some embodiments.

FIG. 12 illustrates a flowchart 1200 of a method for automatically soothing a subject whose sleep has been interrupted, according to some embodiments. As described above, the method may include causing the system to enter the sleep mode (1202) and monitoring the behavior of the subject (1204) to determine when the infant's sleep is interrupted (1206). When the child sleep is interrupted or may be interrupted, the behavior of the child indicating that the sleep is interrupted can often be associated directly with environmental condition that can be adjusted to suit that specific behavior (1208). Thus, the smart-home system attempts to identify a cause-and-effect relationship between specific behaviors of the infant 602 and specific environmental conditions that can be adjusted by the smart-home system.

For example, one such relationship between environmental conditions and behaviors can be associated with air quality. The air purifier 608 can use default parameters that are "baby safe" to help parents know that the air in the sleep environment 604 is safe to breathe. For example, the carbon monoxide threshold alert level can be based on infant age and level of exposure to make the room more safe for the infant 602. The air purifier 608 can also monitor air quality, mold, volatile organic compounds (VOCs) and dangerous ultrafine particulates. The smart-home system can track these levels over time, and alert parents when they rise to harmful levels. The smart-home system can also adjust the operation of the air purifier 608 to bring these levels back to a "baby safe" condition. The smart-home system can also provide alerts to parents and provide recommendations on actions that can be taken to bring these air quality levels into an acceptable range.

In some embodiments, when coughing, sneezing, wheezing, labored breathing, or breathing through a stuffy nose are detected as possibly interrupting the sleep of the infant 602, the condition of the air quality in the sleep environment 604 can be linked as a possible cause of this behavior. Accordingly, the smart-home system can cause the air purifier 608 to increase filtering operations to improve the air quality in the sleep environment 604. The operation of the air purifier 608 can also be influenced by the season and/or weather. During allergy season, the air purifier 608 can increase its operation to filter the air in the sleep environment 604 to remove pollutants and allergens, for example, a small as 0.3 microns. The system can monitor the reaction of the infant 602 in response to adjusting the operation of the air purifier 608 to determine whether adjusting the operation of the air purifier 608 improved the sleep conditions of the infant 602. Thus, the smart-home system can learn over time whether links between environmental conditions and specific subject behaviors are correct, and whether specific adjustments made to environmental conditions improved the subject behavior during sleep. This closed-loop feedback system can in effect learn the types of environmental adjustments that are most effective for a particular subject over time.

The same child behaviors can sometimes be linked to different environmental conditions. In the example above where coughing, sneezing, wheezing, labored breathing, etc., are detected, the smart-home system can attempt to adjust the air quality through the air purifier 608. Additionally or alternatively, these behaviors can also be linked to other environmental conditions, such as humidity. Therefore, detecting these behaviors can also cause the smart-home system to adjust the operation of a humidifier in the sleep environment 604 to increase the humidity level in the sleep environment 604. As different environmental adjustments are applied over time, the smart-home system can monitor the reactions in the behavior of the subject to determine which adjustments are most effective. For example, the smart-home system can, over time, determine whether a coughing infant 602 is most likely to be soothed by increasing air purification, adjusting a humidity level, and/or both.

In another example, the ambient noise level in the sleep environment 604 can be monitored. Particularly in a home with other children, noises from outside the sleep environment 604 may enter the sleep environment 604 and disturb the infant 602. The microphones on various smart-home devices in the sleep environment 604 can monitor the sleep environment 604 for loud noises that are permeating the sleep environment 604. If these loud noises cause the sleep of the infant 602 to be interrupted, the smart-home environment can determine that a link exists between the noise level and the behavior of the subject. In response, the smart-home environment can increase and/or activate soothing noises in the sleep environment 604 to counteract or cover up the noises originating from outside the sleep environment 604. For example, the smart-home environment can cause the home assistant 610 to play white noise, simulated rain, simulated running water, birds sounds, wind, lullabies, classical music, ocean sounds, and/or other noise that has been determined to help subjects go back to sleep. These noises can be played by any smart-home devices in the sleep environment 604 that are equipped with a speaker, such as the hazard detector 104. In some embodiments, these noises can be played by multiple smart-home devices simultaneously to provide a surround-sound effect in the room to better drown out external noise.

In some embodiments, smart-home devices outside of the sleep environment 604 can detect sounds or detect events that will cause sounds to be generated. This information can be communicated to the smart-home devices in the sleep environment 604 to preemptively create, for example, white noise to drown out these impending sounds from outside the sleep environment 604. For example, a smart home system can detect a visitor approaching the entrance of the home. Anticipating that this event will generate a doorbell sound, the home assistant 610 in the sleep environment 604 can generate white noise prior to the doorbell sounding to drown out the doorbell. In some embodiments, smart home systems can provide crowd-sourced information to the server 164 that can be used in nearby locations. For example, if a large truck is traveling down the residential street, the sound made by the truck can be detected by a doorbell system or security sensor in a home at one end of the street. This information can be transmitted through the server 164 to other homes on the street to generate white noise in the sleep environments in those homes to drown out the noise of the truck. Some embodiments may also use schedules of smart-home appliances to responsively schedule counteracting noise generation in the sleep environment 604. For example, the smart-home system may determine that an appliance just outside of the sleep environment 604 is about to turn on. Prior to turning on the appliance, the home assistant 610 can generate counteracting white noise in the sleep environment 604.

Figure 13:
FIG. 13 illustrates an image similar to that of FIG. 8 captured by the thermal imager function of the camera, according to some embodiments.

In some embodiments, the temperature of the infant 602 and/or the thermal signature of the infant can be used to control adjustments to the setpoint temperature in the sleep environment 604. FIG. 13 illustrates an image similar to that of FIG. 8 captured by the thermal imager function of the camera 118, according to some embodiments. The thermal image represents a view of the thermal heat energy emitted/reflected by the infant 602. The thermal image has the advantage of not being dependent upon absolute lighting or variations in lighting for image quality. Instead, the color bands in a facial image indicate different heat bands in the skin of the infant 602. Each individual emits different patterns of thermal energy according to their temperature and facial characteristics. The typical temperature range of the human face/body is often quite uniform on the surface of the skin, varying from 35.5° C. to 37.5° C. The thermal patterns of the infant's face 602 are derived primarily from a pattern of superficial blood vessels that reside under the skin of the infant 602. The vein and tissue structure of every face is unique for each individual, and therefore the thermal images generated of the face of each infant are also unique.

When presented in a thermal image, the slight variations in temperature on the skin of the infant 602 can be represented using different color bands. Colder portions of the skin can be represented with darker colors, such as colors closer to the blue/black end of the color spectrum. Warmer portions of the skin can conversely be represented with lighter colors, such as colors closer to the white/yellow side of the color spectrum. The full-color spectrum in the thermal image can be scaled such that it covers the expected range of temperatures visible on the skin of the infant 602. In FIG. 8, the darker/denser fill patterns of each color band are inversely proportional to the temperature measured by the thermal imager. For example, the cheeks of the infant 602 in FIG. 8 are colder than the area surrounding the eyes of the infant 602.

In some embodiments, the thermal image of the infant 602 can be used to identify the infant 602. As described above, a facial recognition technique using the thermal image can be compared to known images in a local memory and used to determine an identity for the infant 602. Some embodiments may allow users to register different infants or monitored subjects with the smart-home environment through a training process where the camera 118 automatically recognizes a subject that has not been seen before and alerts the user. The user can then provide an identifier (e.g., a name) for the new subject. This can be particularly advantageous in homes or environments with multiple children or subjects that will be monitored. Identities of subjects can be stored locally and securely at the smart-home system.

In some embodiments, a baseline thermal signature can be determined for the infant 602. Establishing a baseline thermal signature can be done in a number of different ways. In some embodiments, a baseline thermal signature can record an average thermal image of portions of the infant's exposed skin 602. First, the algorithm can identify exposed skin of the infant 602 by finding the warmer areas of the image. Exposed skin will generally emit more heat energy than clothed areas of the infant 602. The algorithm can then record an image of the exposed skin as a baseline image. During a learning interval, such as one week, two weeks, one month, etc., the baseline image can be combined/compared with subsequent images to generate an average thermal signature for the infant 602. As used herein, the term "thermal signature" can refer to any thermal characteristic of the infant 602 that may be recorded as a baseline and compared to future thermal images or characteristics. In this example, the thermal signature may be an average thermal image of the face of the infant 602, or a metric derived from the average facial image of the infant 602.

In some embodiments, a baseline thermal signature can include an estimated internal temperature of the infant 602. In some embodiments, the average thermal image of the infant 602 can be assumed to be within a normal, healthy range of internal infant temperatures. In some embodiments, an algorithm has been developed to estimate the internal temperature of the infant 602 based on the thermal image. This algorithm comprises a method that does not require contact and at a remote distance can estimate the internal body temperature of the infant 602 or any other object in the field-of-view of the camera 118. Because the surface temperature is not necessarily consistent with the internal temperature, this algorithm requires a new form of temperature analysis. Specifically, this algorithm derives a transfer function based on a distance of the camera 118 to the infant 602. The algorithm then determines an ambient temperature around the infant 602. For example, using the facial identification routine described above, the algorithm can identify an area around the perimeter of the infant 602, such as location 804. Next, the algorithm can use temperature values from the thermal imager to determine the hottest spot on the skin of the infant 602, such as location 802. Location 802 is most likely closest to the internal temperature of the infant 602. The transfer function can then be computed using this temperature differential to provide an estimate of the inter-ear temperature of the infant 602.

In some embodiments, the system can also filter out thermal signatures that are not of interest or associated with the monitored subject. For example, some embodiments may filter out other heat signatures in the room, such as space heaters, areas surrounding heat vents, while areas that include hot-water pipes, heat-generating electronics, and other heat sources that are not associated with the infant 602. Although these other heat sources may be visible in the live video feed itself, they can be filtered from the thermal image such that they do not interfere with the comparison algorithm described below for determining heat-related characteristics of the infant 602.

In some embodiments, the resolution of the captured video feed can be altered based on the bounding box 902 in FIG. 9. For example, the camera can record and transmit a lower resolution video image for portions of the image outside of the bounding box 902, while preserving a high-resolution digital image for portions of the video feed that are inside the bounding box 902. This can simplify the video processing of a thermal-signature-matching algorithm, decrease the bandwidth required to transmit the live video feed in real time, reduce the amount of processing power required to analyze temperature-related anomalies in the live video feed, and/or reduce the amount of memory required to store images and information associated with the live/thermal video feeds.

Figure 14:
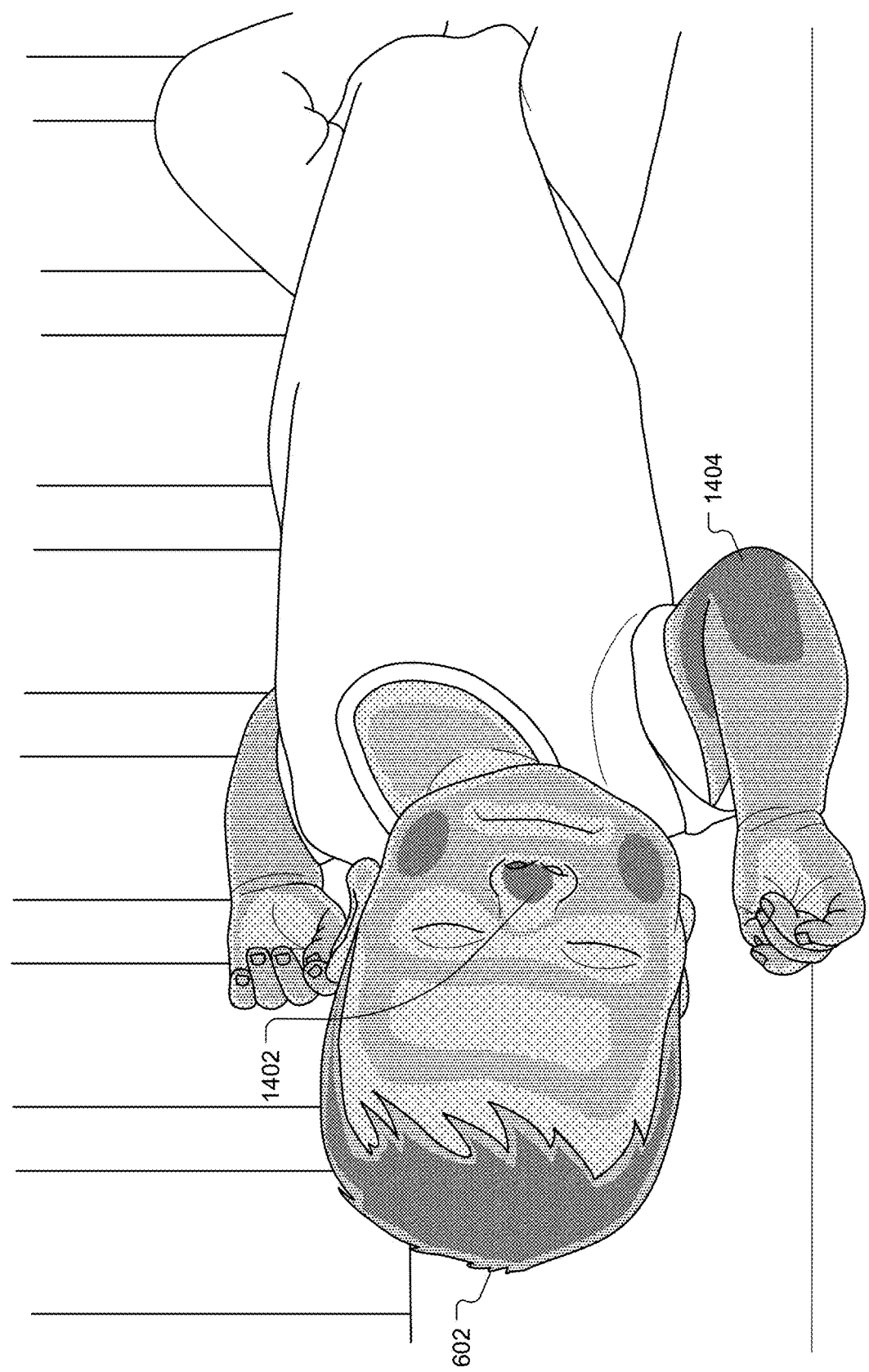
FIG. 14 illustrates a thermal image that can diagnose an infant that is to cold, according to some embodiments.

FIG. 14 illustrates a thermal image that can diagnose an infant 602 that is to cold, according to some embodiments. In this example, certain areas of the image may be colder than the recorded baseline thermal signature. For example, the nose 1402 of the infant 602 may appear to be a darker color in the thermal image than in the baseline image. Similarly, an exposed arm 1404 of the infant 602 may appear to be a darker color than in the baseline image. When certain areas of the infant 602 are colder than the baseline image, this can indicate that the infant 602 is not warm enough. As described below, this situation can generate an alert for a user indicating that the infant 602 may be cold. Additionally or alternatively, this can generate automatic control signals for the smart-home environment to change the environmental characteristics of the area surrounding the infant 602. For example, when the camera 118 detects areas of the infant 602 that are colder than normal, the smart-home environment can generate commands for a thermostat to increase the setpoint temperature of the room of the infant 602. Thus, the colder surface temperature of the skin of the infant 602 can be considered an infant behavior that can be linked to the temperature condition of the sleep environment 604. The thermostat 102 can responsively adjust the temperature in the sleep environment 604 to warm the infant 602. It should be noted that this operation can be done before the infant sleep is actually interrupted.

In some embodiments, a thermal image can be used to diagnose an infant 602 who is teething, suffering from an infection, suffering from a fever, and/or other medical conditions. When the infant 602 is teething, excessive heat may be generated around the mouth of the infant 602. This heat can be visible to the thermal imager around the mouth of the infant 602, appearing lighter in color than normal. As was the case above, the current thermal image of the infant 602 can be compared to a baseline image from a baseline thermal signature, and differences can be isolated and used to diagnose certain conditions. Generally, when a particular isolated area of the infant 602 is warmer than normal, this can indicate different medical conditions, such as infections, ear infections, teething, etc. The algorithm can compare the thermal image of a baseline thermal signature with a current thermal image and identify areas that are warmer by a predetermined threshold amount. As described below, this can generate an alert or informational indication that can be sent to the mobile device of a parent or other user.

Figure 15:
FIG. 15 illustrates a thermal image that can be used to diagnose an infant who is too warm, according to some embodiments.

FIG. 15 illustrates a thermal image that can be used to diagnose an infant 602 who is too warm, according to some embodiments. Generally, when an infant is too warm, the thermal pattern on the skin will be lighter in the thermal image as depicted in FIG. 15. The behavioral condition of being too warm can be linked to environmental condition of the setpoint temperature in the sleep environment 604 being set too high. In response, the smart-home system can cause the thermostat 102 to lower its setpoint temperature to help reduce the skin temperature of the infant 602. This adaptive temperature system can accommodate the different sleep styles that may be used by parents. For example, some parents tend to over-swaddle the infant 602 or place too many clothes on the infant 602 (e.g., beanie, sleep sack, onesie, etc.). The smart-home system can accommodate these different sleep conditions by adjusting the temperature accordingly. Over-swaddled infants can be made comfortable by lowering the temperature in the sleep environment 604. Alternatively, some parents may minimize the amount of clothing and/or blankets in the crib 606 out of caution. The smart-home system can accommodate these sleep conditions by increasing the temperature in the sleep environment 604 automatically. Some embodiments may use computer vision algorithms to identify blankets, hats, and/or other clothing items placed on the infant 602 to help diagnose that the temperature fluctuation on the skin of the infant 602 is due at least in part to such blankets, hats, clothing, etc. In some embodiments, the smart-home system can send an alert to the parents on a mobile device indicating how the temperature has been adjusted, and how such adjustments can be avoided by changing the clothing/bedding style of the infant 602 during sleep time.

In some embodiments, an elevated temperature in a relatively cool sleep environment for infant 602 that is not over-swaddled can indicate a fever condition. When the infant 602 has a fever, the exposed skin in the thermal image, particularly the skin of the face of the infant 602, will be lighter in color, indicating that the infant is warmer than normal. A fever condition can be diagnosed by comparing the current image to a thermal image of the baseline thermal signature for the infant 602. When a temperature differential is detected above a predetermined threshold amount (e.g., 2°, 3°, etc.) a fever diagnosis can be communicated to a parent or other user. In addition to calculating a temperature differential by comparing thermal images, an internal temperature can be estimated for the infant 602. The method described above using a transfer function that incorporates the distance from the camera to the infant 602, the ambient room temperature, and a warmest estimated skin temperature can be used to estimate a current internal temperature of the infant 602. This estimated temperature can be compared in some cases to the baseline temperature to ensure that the diagnosis is correct.

Turning back to FIG. 12, the method may include executing the corresponding environmental adjustments (1210). As described above, this may include changing setpoint temperatures, changing parameters that govern air filter operation, changing lighting conditions, changing sound generation patterns, and so forth. The change in the behavior of the subject in response to these changed environmental controls can be monitored, and determinations can be made as to whether or not they were effective responses to the observed behaviors. Even though default values may be used initially as downloaded from the server 164 or stored on the smart-home devices, these default values can be changed over time to be customized to the sleep habits of the particular infant 602 in the particular sleep environment 604.

In some situations, the observed behavior of the infant 602 might not be associated with any particular environmental condition or control. For example, a baby may become fussy during a sleep cycle due to bad dreams, digestive problems, growing pains, stomach discomfort, needing a diaper change, and/or other problems that are not directly linked to an environmental condition. In these situations, the system can activate additional sleep aids to help the infant 602 go back to sleep (1212). As described above, the sleep aids can be employed at the beginning of the sleep mode to help the infant 602 initially go to sleep. If the sleep of the infant 602 is interrupted or about to be interrupted during the sleep mode, the sleep aids can again be activated for a time interval. Note that in some embodiments, sleep aids can be activated in addition to making adjustments to control the environmental systems. For example, if the infant 602 is too warm, the smart-home system can adjust the setpoint temperature of the thermostat 102 and activate the sleep aids to help soothe and cool down the infant 602 at the same time.

Figure 16:
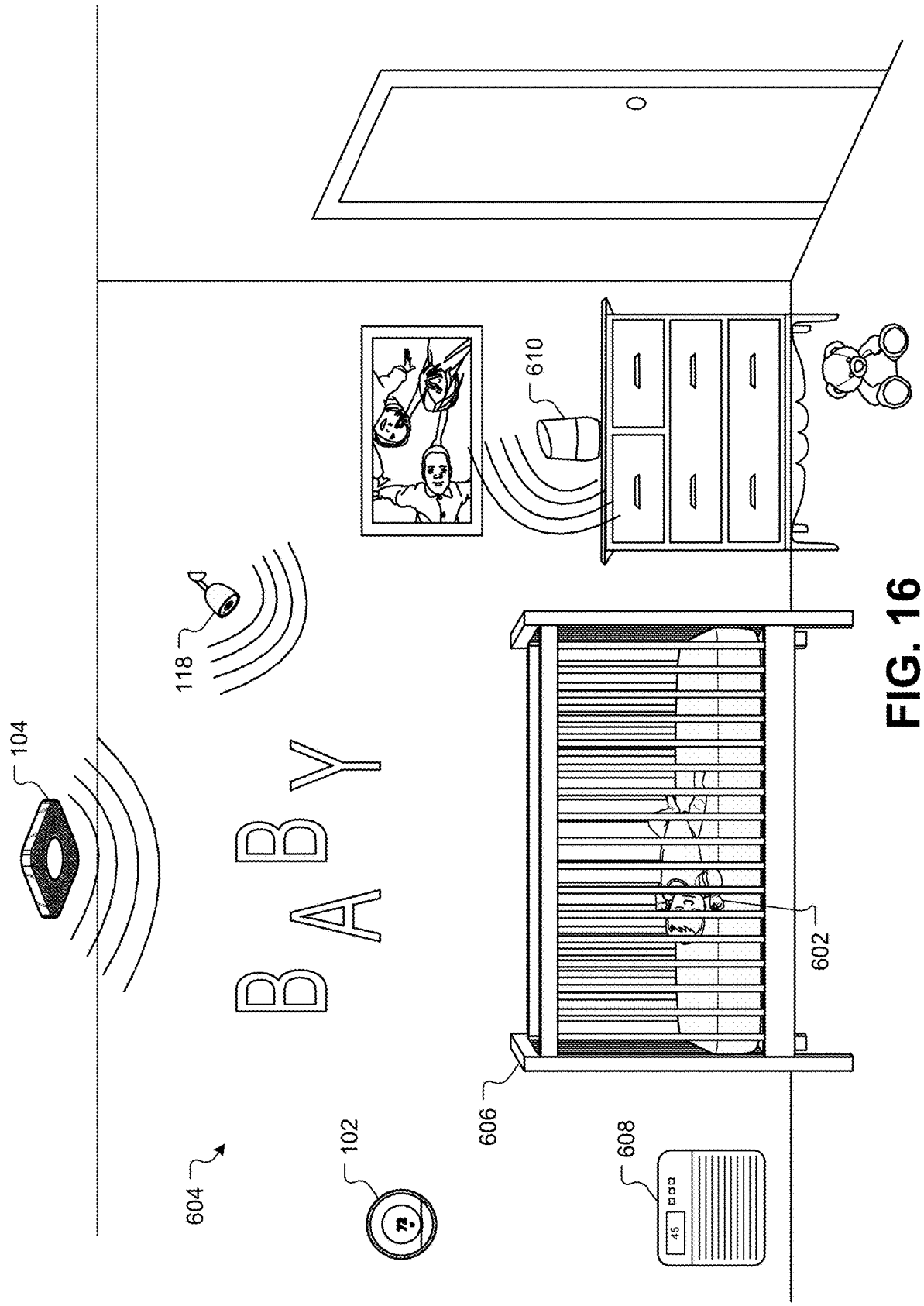
FIG. 16 illustrates how some of the sleep aids can be activated in the sleep environment, according to some embodiments.

FIG. 16 illustrates how some of the sleep aids can be activated in the sleep environment 604, according to some embodiments. One such sleep aid may include generating sleep-inducing noise as described above. The hazard detector 104, the camera 118, the home assistant 610, and/or any of the other smart-home devices equipped with a speaker can generate this sleep-inducing noise. The human brain is still able to perceive and processed sound in the auditory cortex while asleep. Sounds that are relaxing, repetitive, and/or low-level can stimulate the auditory cortex in a way that induces sleep. Such sleep noises may include white noise that approximates a combination of all noise frequencies and can be used to mask other sounds. Other sounds may include simulated appliance noises, such as compressors, refrigerators, vacuum cleaners, washing machines, dryers, dishwashers, and so forth. Other sounds may include nature sounds, such as ocean waves, rain forest animals, thunderstorms, rain, wind, bird sounds, and so forth. Other sounds may include music, such as classical music, lullabies, vibraphone or mellowphone music, or other songs with which the infant 602 might be familiar.

When turning on and/or off, the smart home devices generating the sleep-inducing noise can do so gradually. This can prevent abruptly adding new sounds to the sleep environment 604 or abruptly removing soothing sounds from the sleep environment 604. In some embodiments, multiple smart-home devices can generate different parts of the sleep-inducing sound. For example, bird sounds may be generated by the hazard detector 104, the camera 108, and the home assistant 610. Each of these smart-home devices can generate individual bird noises, giving the effect of an immersive outdoor environment in nature. This effect can also surround the infant 602 with sound in a way that is better calculated to drown out external noises from outside the sleep environment 604.

In some embodiments, the activation of sleep aids may send an alert to, for example, the smart phone of a parent. The parent may then be able to select specific noises to be played in the sleep environment 604. The selections can influence the future automatic operation of the smart-home system. Specifically, the smart-home system can learn from the selections made by the parent to automatically play specified sounds during different portions of the sleep cycle of the infant 602. For example, the smart-home system can learn that the parent prefers a lullaby to be played during the first 15 minutes of the sleep cycle, and prefers white noise to be generated during the remainder of the sleep cycle if sleep is interrupted.

Some embodiments may allow the smart-home devices to act as an intercom system between the sleep environment 604 and the mobile device of the parent or a home intercom system of the smart home. For example, when the infant 602 begins to wake up, an alert can be sent to the computing device of the parent giving the parent the opportunity to not only select noises to be played in the sleep environment 604, but to also talk to the infant 602. Through the computing device, the parent can talk to the infant 602, sing a lullaby to the infant 602, and/or provide any other comforting song or dialogue to help the infant 602 go back to sleep or sleep more soundly.

Figure 17:
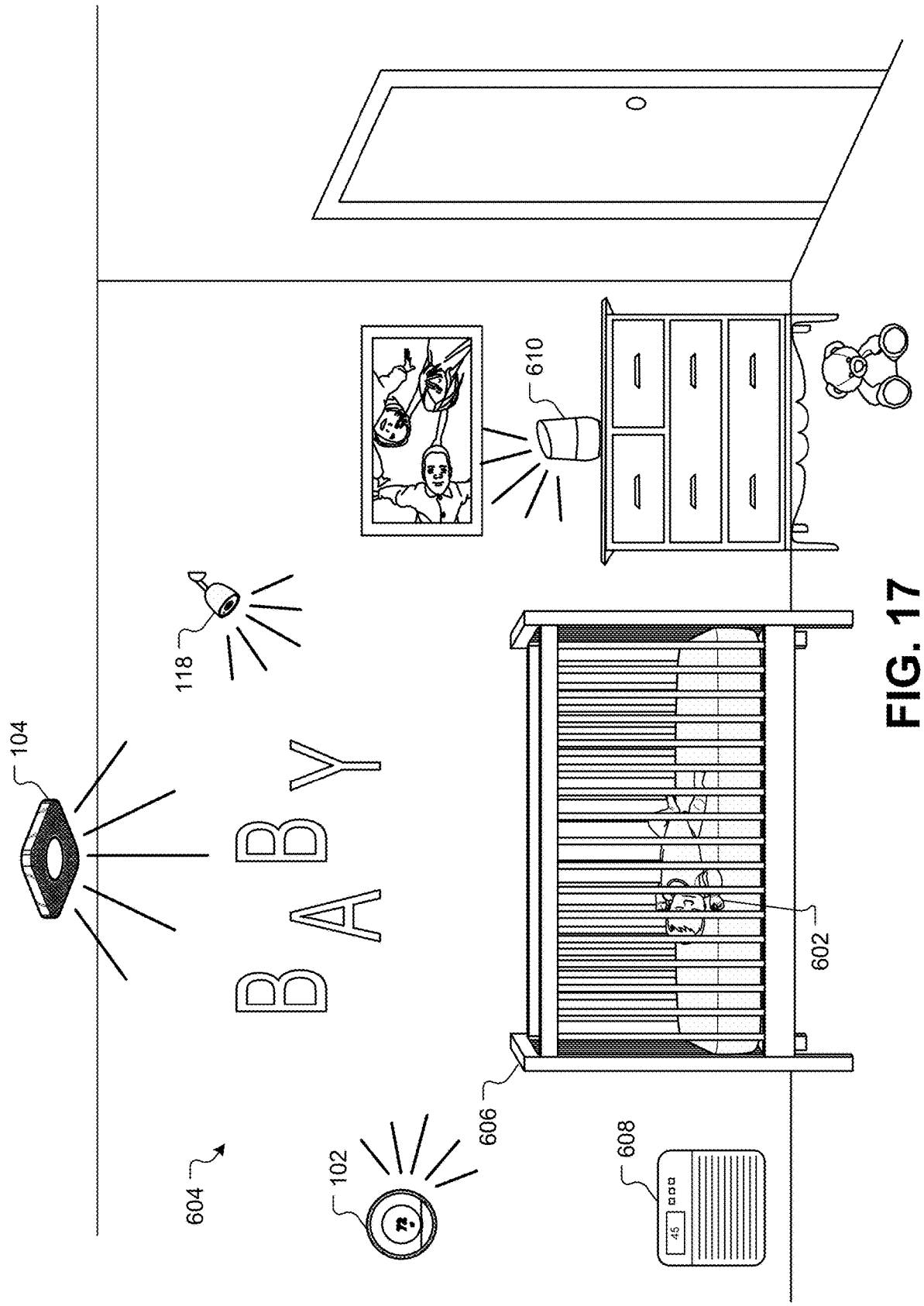
FIG. 17 illustrates how light can be used as a sleep aid to auto-soothe the infant, according to some embodiments.

FIG. 17 illustrates how light can be used as a sleep aid to auto-soothe the infant, according to some embodiments. In addition to providing sound, the hazard detector 104, the camera 118, and/or the home assistant 610 can provide lighting effects that can be used to help soothe the infant 602. In some embodiments, the thermostat 102 may also be equipped with an electronic display that can generate light and/or images in conjunction with the other smart-home devices. In addition to the smart-home devices depicted in FIG. 17, the sleep environment 604 may also include other lighting devices that are controlled by the smart-home system, such as smart lightbulbs or smart outlets that control other lighting appliances.

In some embodiments, when the infant 602 begins to stir in the crib 606, one or more of the smart-home devices equipped with lights can emit a low-level light to provide a nightlight. This can help soothe the infant 602 by allowing them to see just enough of their surroundings to become comfortable in the sleep environment 604. In some embodiments, animations or light patterns can be displayed by the one or more smart-home devices. For example, the display of the thermostat 102 can play animations that may be visible to the infant 602. The lights of any of the smart-home devices can activate in a coordinated fashion to activate in a sequenced pattern to provide an animation effect to the infant 602. In some embodiments, the lighting can be coordinated with the sound emitted from the smart-home devices. For example, lights can be activated when devices play their music in a surround-sound simulation. In another example, lights can be activated in sequence with the rhythm or beats of music being played by the smart-home devices.

In some embodiments, the smart-home devices can activate in situations other than the "auto-soothe" situation when acting as a sleep aid. For example, some lights on the smart-home devices can be active all the time to provide a nursery nightlight for the sleep environment 604. In another example, some lights can automatically and/or gradually turn on in a low-light mode when a parent wants to check on the infant 602. The smart-home system can detect when a parent opens the door through the camera 118, a security system device, and/or by monitoring a location of a smart-home device, such as a smart phone, that is carried by the parent. The parent may also provide inputs that turn on the nursery lighting so that they can check on the infant 602. Generally, the nursery lighting setting will be low enough that the sleep of the infant 602 is not disturbed, while also providing enough light for the parent to navigate the sleep environment 604 and see the infant 602 while sleeping. Additionally, motion sensors, such as the motion sensor in the hazard detector 104, can detect a parent moving across the sleep environment 604 and activate the nursery lighting setting.

This can be done while the system is in the sleep mode to avoid waking up the infant 602. The system can then determine when the parent has left the room and allow the light to persist for short time. Afterwards, the light in the room can gradually fade out to avoid disturbing the infant 602.

Although not depicted explicitly in FIG. 17, the sleep environment 604 may include additional smart-home devices that can provide a soothing function for the infant 602 while sleeping. In some embodiments, the sleep environment 604 may also include a motorized mobile or other infant toy that can be mounted to the crib 606 and activated to soothe the infant 602 when their sleep is disturbed. Such mobiles may include toys, designs, shapes, and/or the like, that rotate above the crib 606. In some embodiments, the sleep environment 604 may also include a vibration device that causes the mattress or crib 606 to vibrate gently to help soothe the infant 602 to sleep. Different sleep environments may include sleep areas other than the crib 606, such as chairs, electric swings, sleep pads, and so forth. Many of these sleep areas may include a vibrating or motion function that can be turned on by the smart-home system as part of a sleep aid or auto-soothing routine.

Turning back briefly to FIG. 12, if the sleep aids (1212) and/or the environmental adjustments (1210) are successful in helping the infant 602 go back to sleep (1214), then the method may continue monitoring the behavior of the infant 602 (1204) until the infant 602 wakes up and/or the sleep of the infant 602 is disturbed again. In some cases, despite the use of the sleep aids and/or environmental adjustments, the infant 602 may not go back to sleep on their own. In these cases, the smart-home system can send an alert to a computing device of a supervisor, parent, guardian, etc., informing them of the actions taken by the smart-home system and/or informing them that the infant 602 has not gone back to sleep on their own (1216).

Figure 18:
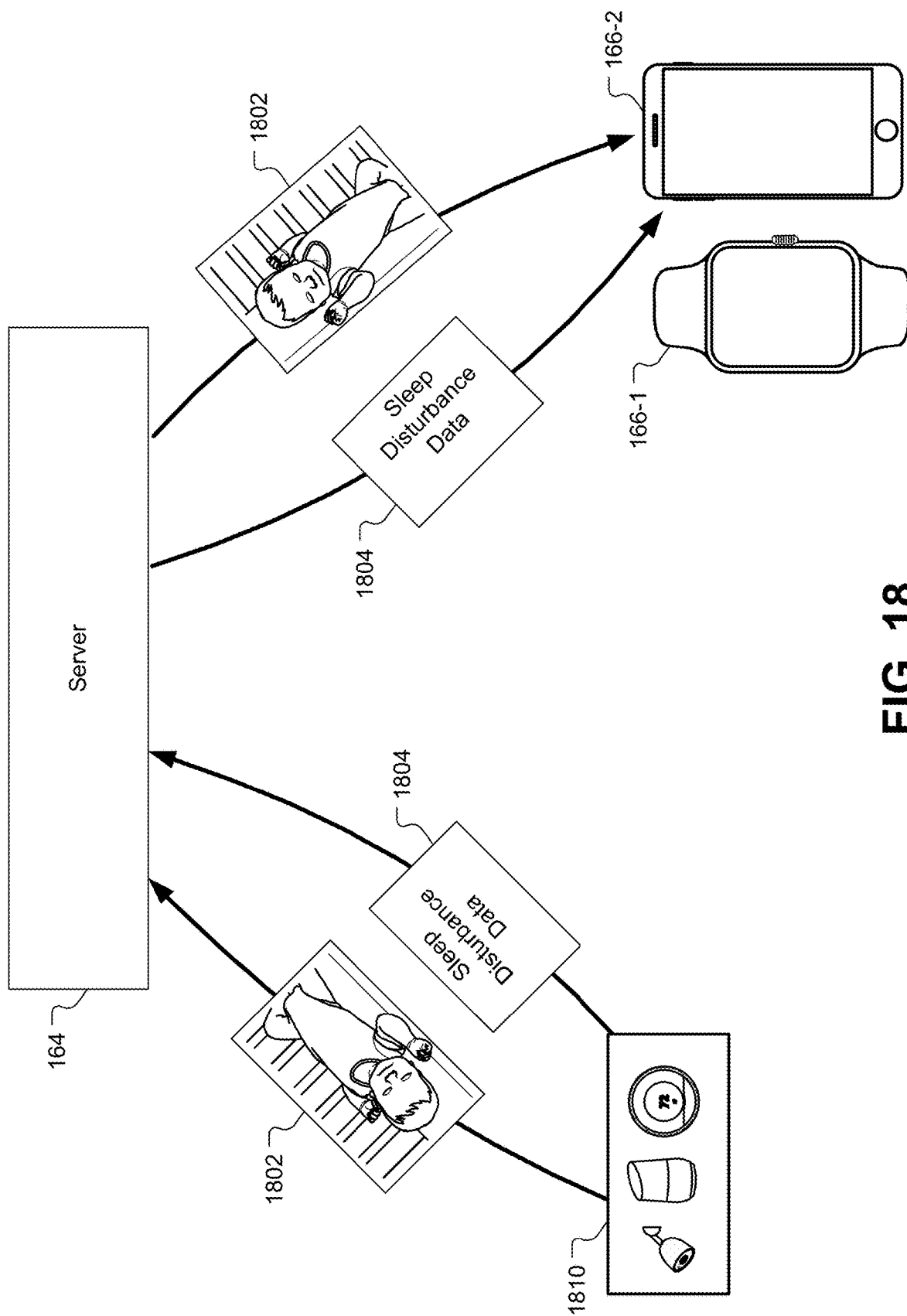
FIG. 18 illustrates a system diagram for processing and transmitting images and information between the smart-home devices in the sleep environment and a user's mobile device, according to some embodiments.

FIG. 18 illustrates a system diagram for processing and transmitting images and information between the smart-home devices 1810 in the sleep environment 604 and a user's mobile device 166, according to some embodiments. In this simplified diagram, some well-understood electronic components may be omitted, such as a power outlet, an ethernet cable, a Wi-Fi home router, and so forth. In some embodiments, the smart-home devices 1810 can capture information regarding the infant 602 and/or the sleep environment 604. For example, the camera 118 may capture a live video feed 1802 of a monitored subject and perform processing operations at the camera 118 itself. As described above, the camera 118 may include one or more processors and one or more memory devices that can be used for executing predefined algorithms on the individual frames of the live/thermal video feed. In the example described above, this may include analyzing a thermal image of the infant 602 to diagnose environmental problems or medical conditions. The camera 118 can send results of this diagnosis to the server 164. Additionally or alternatively, the camera 118 can also send the thermal image data along with the live video feed 1802 to the server 164.

Other smart-home devices 1810 can also send sleep disturbance data 1804 to the server 164. This sleep disturbance data 1804 may include any form of sensor reading, such as sound recordings, threshold violations, motion detection information, thermal signatures, facial expression information, and so forth. In some embodiments, the smart home devices 1810 may include processors like the camera 118, and may be configured to perform data analysis on the sleep disturbance data 1804 before providing it to the server 164. In other embodiments, the smart home devices 1810 can send the sleep disturbance data 1804 in its raw form to the server 164 for analysis.

In some embodiments, the live video feed 1802 and/or the sleep disturbance data 1804 may be captured and transmitted from the smart home devices 1810. A remote server 164 that is accessible over the Internet through a home Wi-Fi router can also perform the image processing algorithms on the live video feed 1802 and/or the thermal image data along with aggregating and analyzing the sleep disturbance data 1804 from the other smart home devices 1810. In these embodiments, the camera 118 can be a high-resolution camera that does not necessarily need to include processors and memories sufficient to execute the motion detection algorithms described above. The server 164 may include a smart-home device monitoring server that collects monitoring information from smart-home devices in the smart-home environment. The server 164 may also provide data synchronization and/or software upgrades to each of the smart-home devices, including the camera 118, in the smart-home environment. The server 164 can be owned and/or operated by a manufacturer of the smart-home devices, including the camera 118. The server 164 may include a dedicated user account for each smart-home environment (e.g., each home). The server 164 may be referred to herein as a smart-home device monitoring server. The server 164 may also be in communication with computer systems of other entities, such as a utility provider computer system (e.g., an energy utility), a law-enforcement computer system, an emergency-response computer system, and so forth. The server 164 may also include memory locations assigned to each particular user account where a historical record of the live video feed 1002 may be stored and/or archived for later retrieval by the user of the account.

The server 164 can transmit the live video feed 1802, the thermal image data, the sleep disturbance data 1804, and/or data analysis, along with any alerts, indications, and/or diagnoses calculated at the smart-home devices 1810 and/or the server 164 to a mobile device 166 of the user associated with the account on the server 164. The mobile device 166 may include a smart watch 166-1, a smartphone 166-2, a laptop computer, a tablet computer, a desktop computer, a personal digital assistant (PDA), an on-board car computer system, a digital home assistant (e.g., Google Home®), and/or any other computing device. In some embodiments, the live video feed 1802, the thermal image data, and/or the sleep disturbance data 1804 can be transmitted directly from the camera 118 to the mobile device 166 without passing through the server 164, but rather through a local wireless network, such as Bluetooth® network or a proprietary smart-home network (e.g., Thread®). Some embodiments may also transmit only the live video feed 1802 and/or the raw sleep disturbance data 1804 to the mobile device 166 and allow the mobile device 166 to process this information to diagnose environmental conditions, sleep disturbances, and/or medical conditions for the infant 602. Therefore, the operations described herein for analyzing the various data and generating indications, alerts, and/or diagnoses can be performed at any of the smart home devices 1810, the server 164, the mobile device 166, and/or any other processing system that is part of the smart-home environment.

Figure 19:
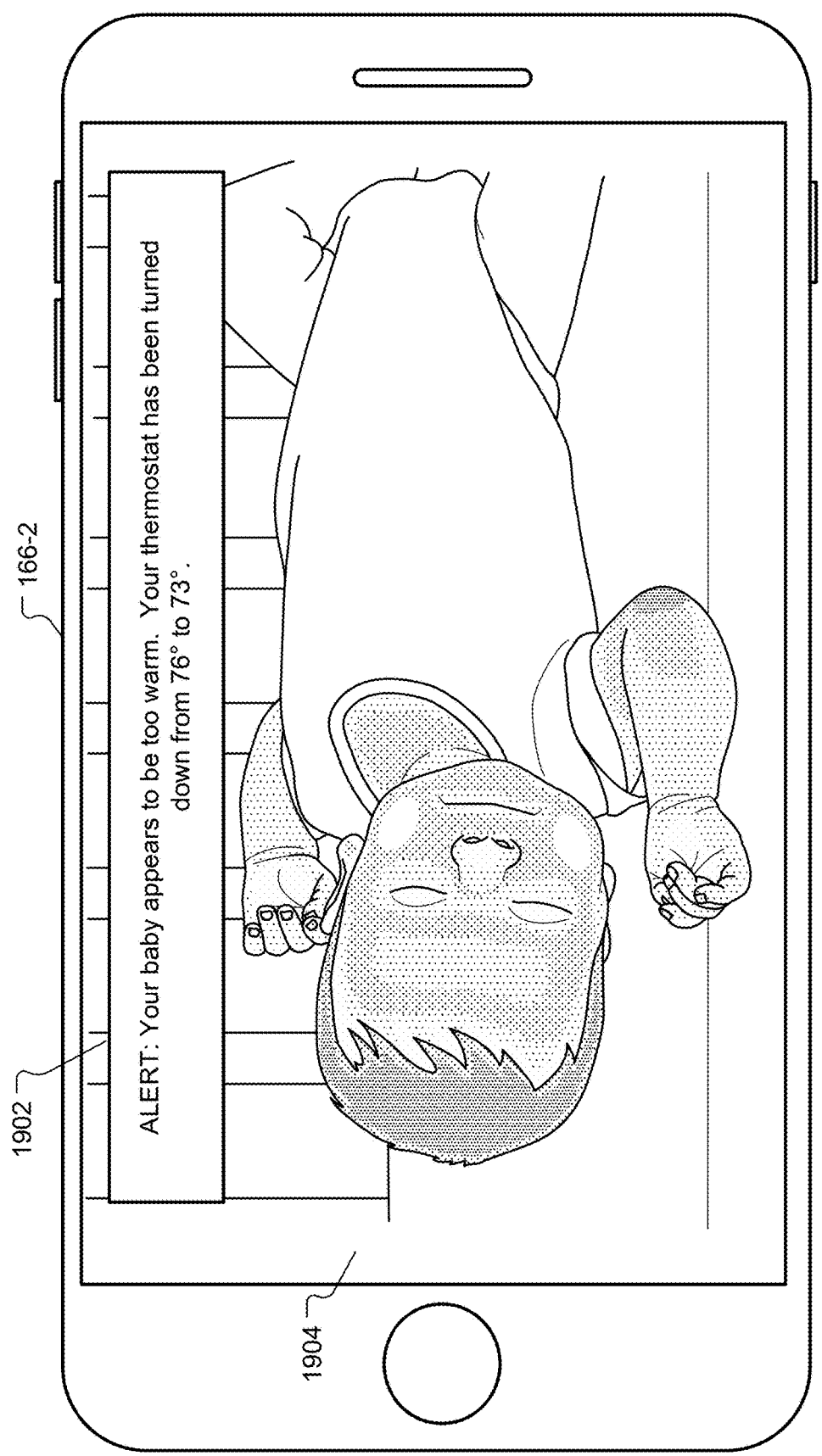
FIG. 19 illustrates a representation of the thermal video feed as it is displayed on a mobile device.

FIG. 19 illustrates a representation of the thermal video feed 1904 as it is displayed on a mobile device 166-2. Seeing the actual thermal video feed 1904 can be useful for providing additional information about the environmental condition or or condition of the infant 602 as determined by the smart-home system. For example, by seeing the thermal video feed 1904, a parent can immediately determine that the infant is swaddled too tightly, has too many blankets, or is not sufficiently covered. This can help the parent or user distinguish between situations where the temperature in the sleep environment 604 is too high in situations where the infant 602 is covered with too many clothes, blankets, etc.

The thermal video feed 1904 can also be used in conjunction with any links to additional information in the alert 1902. For example, some embodiments can transmit thermal images of monitored subjects to the server 164. When a particular condition is detected, the user can select a link provided in the alert 1402 to see other images stored at the server 164 such that they can visually compare these images to the current thermal image of their own infant. For example, by seeing baseline thermal images of their infant 602, the parent can have greater confidence in the abnormal environmental conditions or behavior detected by the smart-home system that are based on the thermal image that they see on their own mobile device 166-2. In another example, if the camera 118 or smart home device 166-2 indicates that the infant has a medical condition such as a fever, seeing additional thermal images may help the parent identify environmental differences that may account for the raised temperature of the infant rather than a fever.

In some embodiments, the smart-home system can store a library of historical thermal images of the infant that can be retrieved and compared over time. This can provide a library of thermal images and estimated temperatures to the parent. Thus, the parent can see how the sleep condition of the infant has progressed day-to-day and week-to-week. By comparing a history of images in the last hour, the alert 1902 can indicate to a user that the infant's temperature is beginning to decrease. Similarly, a history of images can reveal that an infection or teething situation is beginning to subside rather than increase. The alert 1902 can incorporate these findings and indicate that the infant's condition appears to be improving. For example, an alert can be provided not only when disturbed sleep is detected, but also when the child's sleep returns to normal, indicating that the temperature of the infant 602 is returning to normal, the air quality is improving, and so forth.

The alert 1902 can also include links to additional information or to a control panel to further control the smart-home system. For example, the alert 1902 may include a link to a website that describes optimal sleep conditions for the infant 602. In another example, the alert 1902 may include a link to medical information to help diagnose and treat a suspected medical condition. In another example, the alert 1902 may include a link to a control panel in an app/application provided by the smart-home system to control the smart-home devices in the sleep environment 604. The control panel may include different options that the parent can activate, such as any of the auto-soothing systems described above, including lighting, sound, moving devices, vibration, and so forth. The alert 1902 may also include a list of control operations that have already been executed by the smart-home system in the sleep environment 604. For example, the alert 1902 describes the condition of the infant 602 ("your baby appears to be too warm"). The alert 1902 also includes a list of actions that were taken by the smart-home system ("your thermostat has been turned down from 76° to 73°"). In some embodiments, the alert 1902 may include additional actions or control operations that may be taken by selecting those options in the alert 1902. For example, be alert 1902 may include an option to turn on additional sounds in the sleep environment 604 ("would you like to activate the white noise generator?"). By selecting this option, the parent can activate additional smart-home systems in the sleep environment 604 as described above. Thus, not only does the smart-home system automatically respond to the disrupted sleep of the infant 602, but parents or guardians are given full control over the system in real-time to tailor the response of the smart-home system as they see fit. When the parents or guardians provide these inputs, the smart-some system can tailor its responses in the future to correspond to the actions taken in the past by the parents or guardians.

Figure 20:
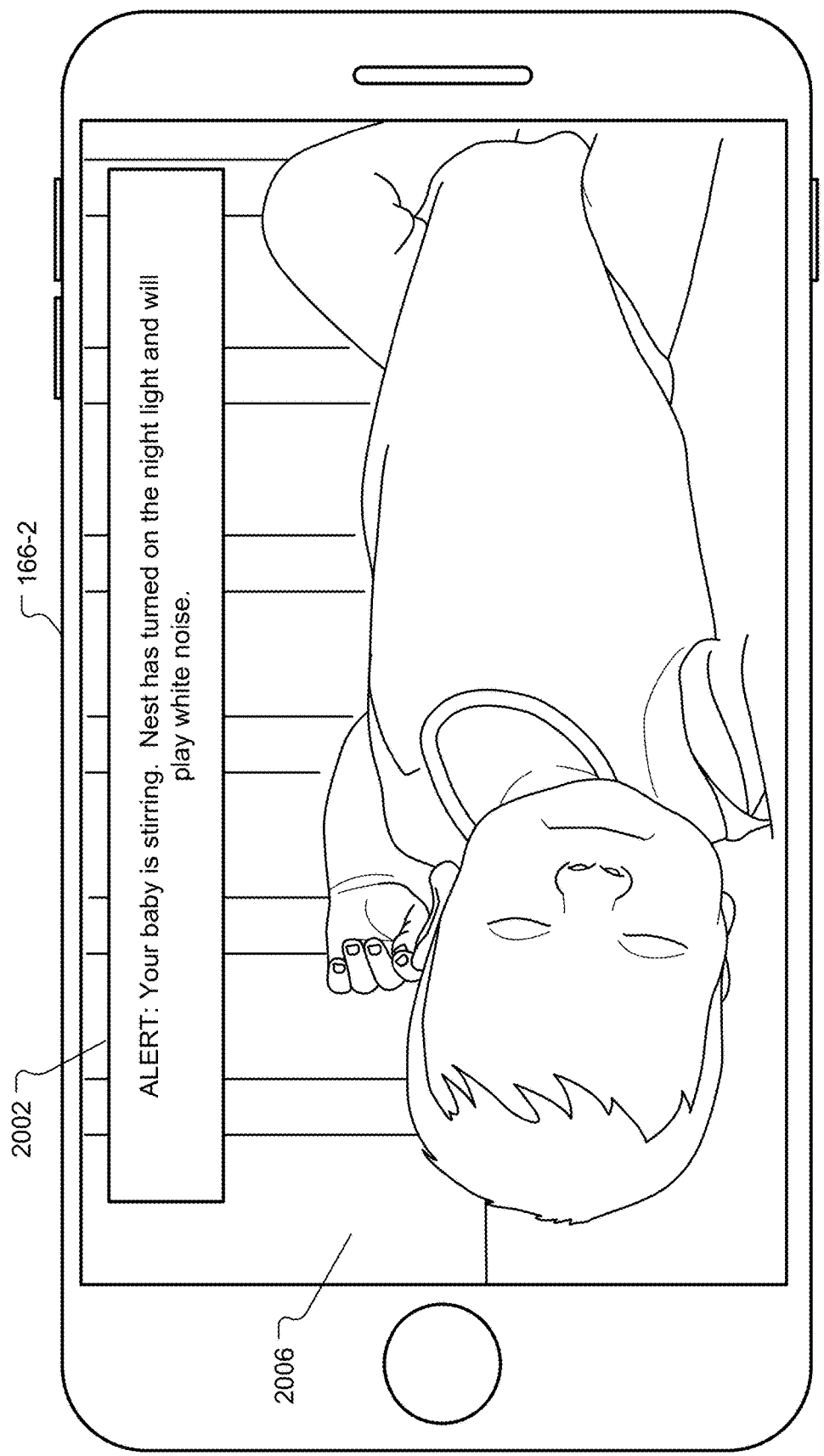
FIG. 20 illustrates a representation of the live video feed displayed on a mobile device, according to some embodiments.

FIG. 20 illustrates a representation of the live video feed 2006 displayed on a mobile device 166-2, according to some embodiments. The live video feed 1406 can be displayed on the screen of the mobile device 166-2 as the user monitors the infant 602. In some cases, the infant 602 may be monitored on the mobile device 166-2 for an extended period of time, where real-time video is displayed to the user. This can be done to enhance the emotional connection between the user and the infant through the mobile device 166-2. For example, a parent who needs to be away from the infant during the day can log into the server 164 using the mobile device 166-2 and watch real-time video of the infant.

In some cases, the user can monitor the infant to watch for sleep disturbances, and medical emergency conditions, and/or times when the infant 602 wakes up. While normal video streams of previous systems in the art would make it difficult or impossible to visually see or detect these medical conditions, the camera system and thermal imager described above can make these medical conditions readily apparent to an observer of the mobile device 166-2. In addition to simply displaying the real-time video feed 2006, the mobile device 166-2 can also display visual/audio warnings or status messages for any of the medical conditions detected above. In the example of FIG. 20, an alert 2002 is displayed on the screen indicating that the sleep of the infant 602 appears to be disturbed. The alert may include a vibration, a sound, and/or color encodings that indicate the severity of the alert. For example, a temperature elevated by more than 2° can generate an alert 1402 that is colored red and generates an audible alarm and/or vibration of the mobile device 166-2. Some embodiments may also generate indications that include additional information based on the behavior that is observed. For example, if the smart-home system indicates that the infant 602 is coughing, the alert 2002 can include a number of times that the infant has coughed, time intervals during which coughs have been detected, intensity of coughs, and so forth. As described above, the alert 2002 may include information regarding control actions that have already been executed or which are planned to be executed by the smart-home system. For example, the alert 2002 may indicate that the smart-home system has turned on one or more nightlights and will begin playing a white noise track. As described above, the alert 2002 may also include an option for the parent to personally check on the infant 602. By selecting this option, the smart-home system can automatically turn on one or more low-level lights in the sleep environment 604 to allow the parent to see the infant 602 when they enter the sleep environment 604.

Figure 21:
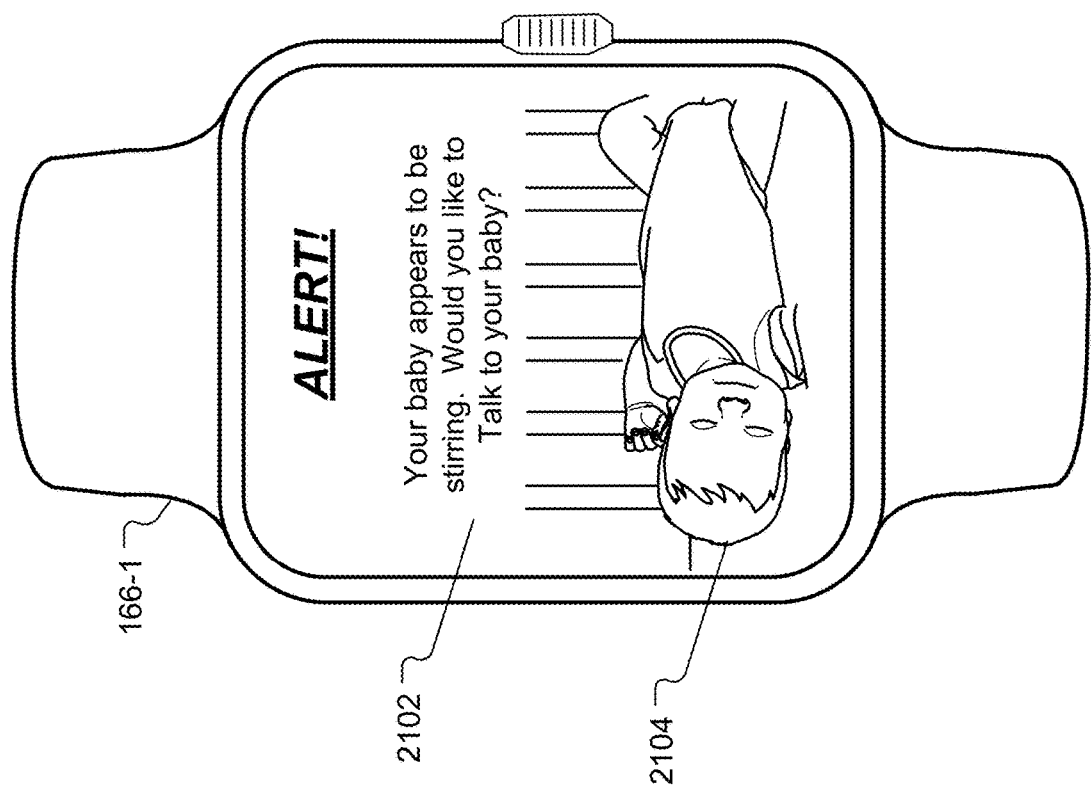
FIG. 21 illustrates an alternative visual representation of an alert on a mobile device 166-1, according to some embodiments.

FIG. 21 illustrates an alternative visual representation of an alert on a mobile device 166-1, according to some embodiments. In this embodiment, the mobile device 166-1 may include a smart watch or other piece of wearable technology. This alert 2102 is similar to the alert illustrated in FIG. 20 indicating that the infant appears to be stirring. The display may also include a thermal image of the monitored subject. Alternatively or additionally, the mobile device 166-1 may include the live video feed 2104 as depicted in FIG. 21. In any embodiment, mobile devices 166 may allow the user to toggle back and forth between the images from the thermal video feed and the images from the live video feed.

The alert 2102 may include the option to allow the user to talk to the infant 602 through the mobile device 166-1 and have their voice broadcast by a one or more of the smart home devices in the sleep environment 604. A microphone on the mobile device 166-1 can allow the parent to, for example, sing to the infant 602, play a song for the infant 602, tell a story to the infant 602, and so forth. Thus, the smart-home system can establish a video/audio link between the sleep environment 604 and the mobile device 166-1. In some embodiments, the sleep environment 604 may include a monitor that is visible from the crib 606 that displays video of the parent as captured by the mobile device 166-1, and may thereby provide a two-way video/audio feed for the infant 602 and the parent to communicate.

Figure 22:
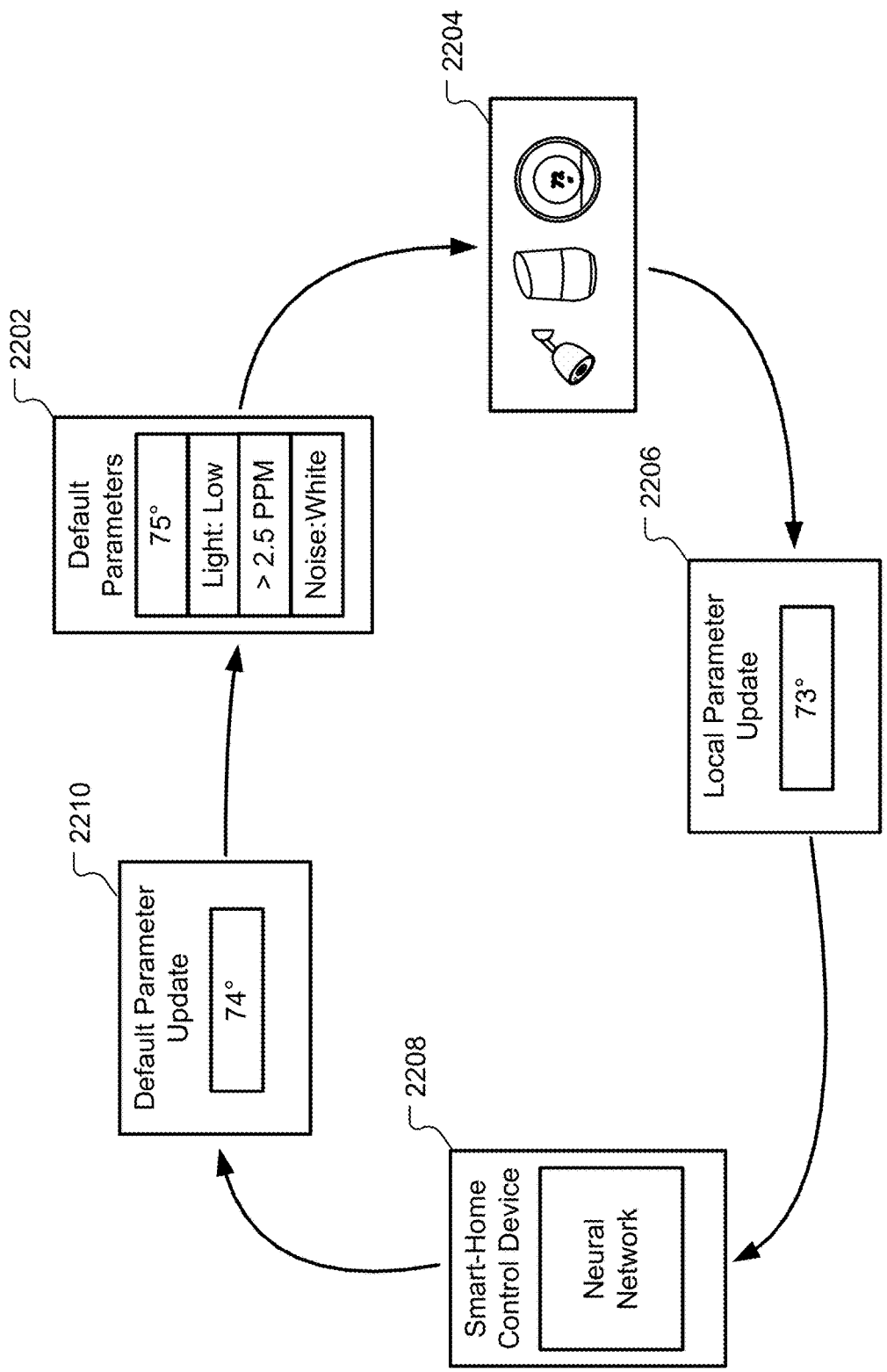
FIG. 22 illustrates a closed-loop local feedback system for updating default sleep-mode parameters, according to some embodiments.

FIG. 22 illustrates a closed-loop local feedback system for updating default sleep-mode parameters, according to some embodiments. As described briefly above, the smart-home system can constantly be learning behaviors of the infant 602 and/or the appropriate responses to take in different situations such that the sleep environment 604 can be optimized. The default parameters 2202 can be received from the server and/or stored on the smart home devices 2204 as described above. These default parameters may represent parameters that have been found to be optimal for controlling smart home devices for a population of infants that are similar to a particular infant 602. These default parameters 2202 can be used to control the operation of the smart home devices 2204 during the sleep mode.

As the system operates, it can monitor the effects of certain actions that are taken and the corresponding responses of the infant 602. For example, the default parameter for a temperature setpoint may be 75°. However, keeping the sleep environment 604 at 75° may cause the infant 602 to become too warm according to the thermal images captured by the thermal imager of the camera 118. By linking this elevated temperature to the control of the thermostat, the smart-home system can decrease the setpoint temperature of the thermostat 102 down to 73°. The camera 118 can then monitor that reaction of the infant 602 to the temperature change. The infant reaction can be represented by a Boolean value as being successful are not successful. Alternatively or additionally, the infant reaction can use a more complex representation, such as a scale between successful and unsuccessful. Both the reaction of the infant 602 and the local update to the parameter 2206 can be fed into a neural network or machine learning algorithm of a smart home controller device 2208. Any of the smart home devices with a processor can act as the smart-home control device 2208. Additionally, a data hub, a workstation, a laptop, and/or any other computing device can act as the smart-home control device.

The neural network or machine learning algorithm of the smart-home control device 2208 can monitor local parameter updates and corresponding infant responses over time and generate changes to the default parameters. For example, if the thermostat is repeatedly turned down from the default parameter value of 75°, and more often than not the infant responds positively to this temperature change by going back to sleep, the neural network or machine learning algorithm can determine that the default parameter representing the temperature setpoint of the thermostat 102 can be lowered incrementally. In the example of FIG. 22, the system can close the feedback loop by providing a default parameter update 2210 to the default parameters 2202. The updated default parameters 2202 can be used in the smart home devices 2204 the next time they enter the sleep mode.

The closed-loop feedback system of FIG. 22 can use control inputs that are automatically generated by the smart-home system. Additionally or alternatively, the feedback system can use the user inputs from parents received through mobile devices. In some embodiments, user inputs can be weighed more heavily than control inputs that are automatically generated by the system. As the system learns, automatic control actions that do not result in a successful outcome for the sleep behavior of the infant can be reduced such that they are less likely to take place in the future.

Figure 23:
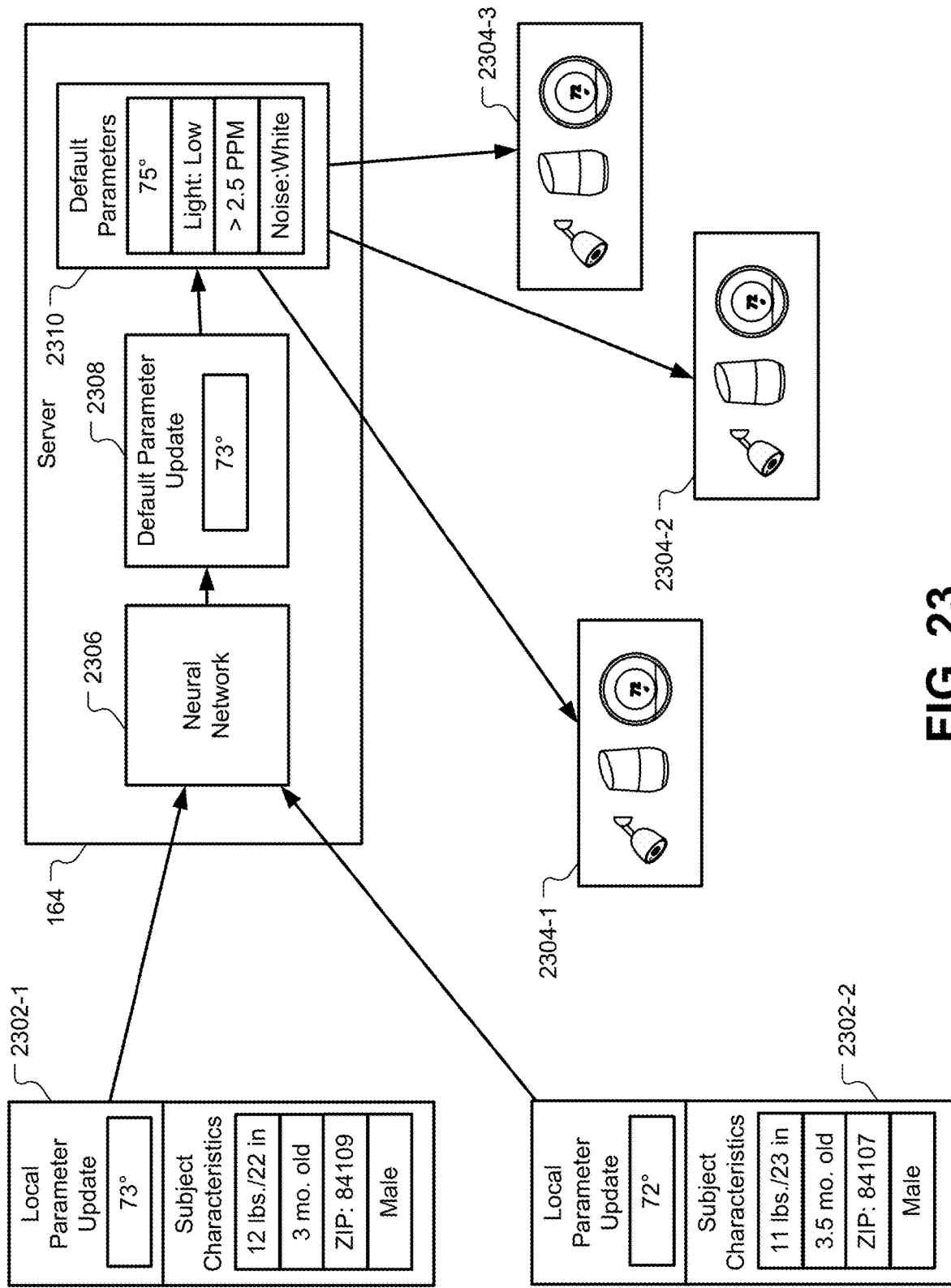
FIG. 23 illustrates a crowd-sourced feedback system for updating default sleep parameters for populations of similar subjects, according to some embodiments.

FIG. 23 illustrates a crowd-sourced feedback system for updating default sleep parameters for populations of similar subjects, according to some embodiments. The default parameters 2310 may originally be distributed to a plurality of smart home environments 2304 which may correspond to different homes, residences, buildings, enclosures, and so forth.

These default parameters 2310 can operate in the smart home environments 2304 using the closed loop feedback system described above in relation to FIG. 22. As described above, the default parameters 2310 can correspond to clustered populations of monitored subjects having similar characteristics.

As the closed loop feedback systems for each of the smart-home environments 2304 update the default parameter values, the smart home environments 2304 can send local parameter updates 2302 back to the server 164. A neural network 2306 can receive all the local parameter updates 2302 and determine when a sufficient number of similar updates have been received to generate a default parameter update 2308 for the default parameters 2310. For example, if the default parameters 2310 represent a population of approximately 500 subjects having similar characteristics, the neural network 2306 can generate the default parameter update 2308 when a threshold number (e.g., 50) of local parameter updates 2302 have been received for a particular parameter value.

When the local parameter updates 2302 are received, the neural network can cause the default parameters 2310 to change in magnitude in the direction of the average of the local parameter updates 2302. Alternatively or additionally, the neural network 2306 can generate a new cluster of similar individuals. For example, if the local parameter updates 2302 all come from very similar subjects and/or sleep environments, the neural network can split the existing cluster into two separate clusters. The cluster associated with the local parameter updates 2302 can use the same existing default parameters 2310 but incorporate the default parameter update 2308. The remainder of the previous cluster can continue to use the default parameters 2310 without the default parameter update 2308.

The local parameter updates 2302 may include characteristics of the subject and/or the sleep environment when permission to share such information is granted by the parents or other monitor of the subject. Information such as the subject name, address, etc. need not be shared with the server 164. Alternatively or in conjunction therewith, any of a variety of known data anonymization methods can be used to protect user privacy, while at the same time providing statistically useful data for purposes of achieving the features and advantages of the embodiments described herein.

It should be appreciated that the specific steps illustrated in FIG. 15 provide particular methods of monitoring physical characteristics of subjects in sleep environments according to various embodiments of the present invention. Other sequences of steps may also be performed according to alternative embodiments. For example, alternative embodiments of the present invention may perform the steps outlined above in a different order. Moreover, the individual steps illustrated in FIG. 15 may include multiple sub-steps that may be performed in various sequences as appropriate to the individual step. Furthermore, additional steps may be added or removed depending on the particular applications. One of ordinary skill in the art would recognize many variations, modifications, and alternatives.

In the foregoing description, for the purposes of explanation, numerous specific details were set forth in order to provide a thorough understanding of various embodiments of the present invention. It will be apparent, however, to one skilled in the art that embodiments of the present invention may be practiced without some of these specific details. In other instances, well-known structures and devices are shown in block diagram form.

The foregoing description provides exemplary embodiments only, and is not intended to limit the scope, applicability, or configuration of the disclosure. Rather, the foregoing description of the exemplary embodiments will provide those skilled in the art with an enabling description for implementing an exemplary embodiment. It should be understood that various changes may be made in the function and arrangement of elements without departing from the spirit and scope of the invention as set forth in the appended claims.

Specific details are given in the foregoing description to provide a thorough understanding of the embodiments. However, it will be understood by one of ordinary skill in the art that the embodiments may be practiced without these specific details. For example, circuits, systems, networks, processes, and other components may have been shown as components in block diagram form in order not to obscure the embodiments in unnecessary detail. In other instances, well-known circuits, processes, algorithms, structures, and techniques may have been shown without unnecessary detail in order to avoid obscuring the embodiments.

Also, it is noted that individual embodiments may have been described as a process which is depicted as a flowchart, a flow diagram, a data flow diagram, a structure diagram, or a block diagram. Although a flowchart may have described the operations as a sequential process, many of the operations can be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination can correspond to a return of the function to the calling function or the main function.

The term "computer-readable medium" includes, but is not limited to portable or fixed storage devices, optical storage devices, wireless channels and various other mediums capable of storing, containing, or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc., may be passed, forwarded, or transmitted via any suitable means including memory sharing, message passing, token passing, network transmission, etc.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

In the foregoing specification, aspects of the invention are described with reference to specific embodiments thereof, but those skilled in the art will recognize that the invention is not limited thereto. Various features and aspects of the above-described invention may be used individually or jointly. Further, embodiments can be utilized in any number of environments and applications beyond those described herein without departing from the broader spirit and scope of the specification. The specification and drawings are, accordingly, to be regarded as illustrative rather than restrictive.

Additionally, for the purposes of illustration, methods were described in a particular order. It should be appreciated that in alternate embodiments, the methods may be performed in a different order than that described. It should also be appreciated that the methods described above may be performed by hardware components or may be embodied in sequences of machine-executable instructions, which may be used to cause a machine, such as a general-purpose or special-purpose processor or logic circuits programmed with the instructions to perform the methods. These machine-executable instructions may be stored on one or more machine readable mediums, such as CD-ROMs or other type of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

What is claimed is:

1. A method of monitoring and optimizing sleep of a subject using a plurality of smart-home devices, the method comprising:
    operating a smart-home system comprising the plurality of smart-home devices, wherein the smart-home system is configured to operate in a plurality of modes comprising:
        a normal operating mode; and
        a sleep mode;
    determining that the smart-home system should transition into the sleep mode from the normal operating mode, wherein:
        the plurality of smart-home devices use a set of default parameters when operating in the sleep mode; and
        noise-generating smart-home devices in the plurality of smart-home devices have their sound outputs lowered or disabled when the smart-home system is in the sleep mode;
    monitoring, while in the sleep mode, a sleep cycle of the subject using the plurality of smart-home devices;
    receiving an indication of a noise outside of a home in which the smart-home system is installed, wherein the indication is crowd-sourced from of the plurality of smart-home systems in different homes;
    adjusting an environmental control using the plurality of smart-home devices to counteract the noise and prevent or stop the sleep cycle of the subject from being interrupted;
    determining whether adjusting the environmental control using the plurality of smart-home devices prevented or stopped the sleep cycle of the subject from being interrupted; and
    adjusting the set of default parameters for use in subsequent instances where the sleep cycle of the subject is being interrupted, wherein the set of default parameters are adjusted based on a determination of whether adjusting the environmental control using the plurality of smart-home devices prevented or stopped the sleep cycle of the subject from being interrupted.

2. The method of claim 1, wherein the plurality of smart-home devices comprises a camera with a thermal imager.

3. The method of claim 2, further comprising:
    detecting behavior of the subject that indicates that the sleep cycle of the subject is being interrupted determining, using the thermal imager, that a temperature of the subject is above or below a target temperature.

4. The method of claim 3, wherein the thermal imager captures a thermal image of a face of the subject and compares the thermal image of the face of the subject to a baseline thermal image of the face of the subject.

5. The method of claim 3, wherein the plurality of smart-home devices comprises a thermostat, and the method further comprises:
    adjusting a temperature setpoint of the thermostat to bring the temperature of the subject closer to the target temperature.

6. The method of claim 1, wherein determining that the smart-home system should transition into the sleep mode comprises determining, using a camera in the plurality of smart-home devices, that the subject is in a sleep environment that is monitored by the plurality of smart-home devices.

7. The method of claim 1, wherein determining that the smart-home system should transition into the sleep mode comprises receiving an input from a user indicating that the sleep cycle of the subject is beginning.

8. The method of claim 1, wherein determining that the smart-home system should transition into the sleep mode comprises learning, by the smart-home system, a schedule of the sleep cycle of the subject over time.

9. The method of claim 1, wherein the set of default parameters comprises parameters that are associated with a population of subjects that are similar to the subject.

10. A smart-home system for monitoring and optimizing sleep of a subject using a plurality of smart-home devices, the smart-home system comprising:
   a plurality of smart-home devices that are configured to operate in a plurality of modes comprising:
      a normal operating mode; and
      a sleep mode;
   one or more processors; and
   one or more memory devices comprising instructions that, when executed by the one or more processors, cause the one or more processors to perform operations comprising:
      determining that the smart-home system should transition into the sleep mode from the normal operating mode, wherein:
         the plurality of smart-home devices use a set of default parameters when operating in the sleep mode; and
         noise-generating smart-home devices in the plurality of smart-home devices have their sound outputs lowered or disabled when the smart-home system is in the sleep mode;
      monitoring, while in the sleep mode, a sleep cycle of the subject using the plurality of smart-home devices;
      receiving an indication of a noise outside of a home in which the smart-home system is installed, wherein the indication is crowd-sourced from of the plurality of smart-home systems in different homes;
      adjusting an environmental control using the plurality of smart-home devices to counteract the noise and prevent or stop the sleep cycle of the subject from being interrupted;
      determining whether adjusting the environmental control using the plurality of smart-home devices prevented or stopped the sleep cycle of the subject from being interrupted; and
      adjusting the set of default parameters for use in subsequent instances where the sleep cycle of the subject is being interrupted, wherein the set of default parameters are adjusted based on a determination of whether adjusting the environmental control using the plurality of smart-home devices prevented or stopped the sleep cycle of the subject from being interrupted.

11. The smart-home system of claim 10, wherein the set of default parameters are downloaded from a monitoring server that communicates and processes data from a plurality of smart-home systems.

12. The smart-home system of claim 10, wherein the set of default parameters cause the plurality of smart-home devices to be configured to minimize external noise in a sleep environment for the subject.

13. The smart-home system of claim 10, further comprising:
   detecting behavior of the subject that indicates that the sleep cycle of the subject is being interrupted, wherein the behavior of the subject that indicates that the sleep cycle of the subject is being interrupted comprises coughing or sneezing by the subject; and
   adjusting an operation of an air purifier or humidifier.

14. The smart-home system of claim 10, wherein the plurality of smart-home devices comprises a thermostat, a camera, and a hazard detector.

15. The smart-home system of claim 10, wherein the smart-home system further comprises a monitoring server, wherein the one or more processors are distributed between the plurality of smart-home devices and the monitoring server.

16. The smart-home system of claim 10, wherein the operations further comprise:
   determining that a user is entering a sleep environment of the subject;
   causing one or more of the plurality of smart-home devices to generate a low-level night light.

17. The smart-home system of claim 10, wherein the operations further comprise, after transitioning into the sleep mode, causing one or more sleep aids to be activated until it is determined that the subject is asleep.

18. The smart-home system of claim 17, wherein the one or more sleep aids comprise one or more of the following: white noise generation, low-level lighting, music, vibrations, and mobile activation.

19. The smart-home system of claim 10, wherein the operations further comprise adjusting the set of default parameters based on adjusting the environmental control.

* * * * *